(12) United States Patent
Lawrence et al.

(10) Patent No.: US 8,574,900 B2
(45) Date of Patent: *Nov. 5, 2013

(54) NUCLEIC ACID SILENCING SEQUENCES

(75) Inventors: Jeanne B. Lawrence, Mapleville, RI (US); Lisa L. Hall, Sudbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/483,240

(22) Filed: May 30, 2012

(65) Prior Publication Data

US 2012/0252123 A1 Oct. 4, 2012

Related U.S. Application Data

(63) Continuation of application No. 12/512,964, filed on Jul. 30, 2009, now Pat. No. 8,212,019.

(60) Provisional application No. 61/084,918, filed on Jul. 30, 2008.

(51) Int. Cl.
| | |
|---|---|
| *C12N 15/85* | (2006.01) |
| *A61K 48/00* | (2006.01) |
| *A61K 35/00* | (2006.01) |
| *C07H 21/04* | (2006.01) |

(52) U.S. Cl.
USPC .... 435/325; 536/23.1; 536/24.31; 536/24.33; 536/24.5; 514/44; 424/93.1

(58) Field of Classification Search
None
See application file for complete search history.

(56) References Cited

PUBLICATIONS

Brockdorff and Duthie, "X Chromosome Inactivation and the Xist Gene," Cell. Mol. Life Sci. 54:104-112, 1998.
Brown et al., "The Human Xist Gene: Analysis of a 17kb Inactive X-specific RNA That Contains Conserved Repeats and is Highly Localized Within the Nucleus," Cell 71:527-542, 1992.
Cathomen and Joung, "Zinc-finger Nucleases: The Next Generation Emerges," Molecular Therapy 16(7):1200-1207, 2008.
Chow et al., "Inducible XIST-dependent X-chromosome Inactivation in Human Somatic Cells is Reversible," Proc Natl Acad Sci USA 104:10104-10109, 2007.
Greene and Lowrey, "The Human Xist Gene Promoter Prevents Silencing o fan Integrated Reporter Gene," Blood, 2004, vol. 104 (11), Abstract #2114.
Hall et al., "An Ectopic Human XIST Gene can induce chromosome inactivation in post differentiation human HT-1080 cells," Proc Natl Acad Sci USA 99:8677-8682, 2002.
International Search Report and Written Opinion for PCT/US2009/052318, mailed Apr. 30, 2010.
Lau et al., "Skewed X-Chromosome Inactivation is Common in Fetuses or Newborns Associated with Confined Placental Mosaicism," Am. J. Hum. Genet. 61:1353-1361, 1997.
Migeon et al., "X Inactivation in Triploidy and Trisomy: The Search for Autosomal Transfactors that Choose the Active X," European Journal of Human Genetics 16:153-162, 2008, published on-line Oct. 31, 2007.
Moehle et al., "Targeted gene addition into a specified location in the human genome using designed zinc finger nucleases," Proc Natl Acad Sci USA 104:3055-3060, 2007.
Porteus, "Mammalian Gene Targeting with Designed Zinc Finger Nucleases," Molecular Therapy 13(2):438-446, 2006.
Savarese et al., "Hematopoietic Precursor Cells Transiently Reestablish Permissiveness for X Inactivation," Molecular and Cellular Biology 26(19):7167-7177, 2006.
U.S. Patent and Trademark Office, Restriction Requirement in U.S. Appl. No. 12/512,964, mailed Apr. 6, 2011 (9 pages).
Fish & Richardson P.C., Response to Restriction Requirement in U.S. Appl. No. 12/512,964, filed Jul. 6, 2011 (8 pages).
U.S. Patent and Trademark Office, Non Final Office Action in U.S. Appl. No. 12/512,964, mailed Sep. 21, 2011 (12 pages).
Fish & Richardson P.C., Response to Office Action in U.S. Appl. No. 12/512,964, filed Jan. 23, 2012 (10 pages).
U.S. Patent and Trademark Office Notice of Allowance in U.S. Appl. No. 12/512,964, mailed Mar. 5, 2012 (9 pages).
U.S. Patent and Trademark Office Notice of Allowability in U.S. Appl. No. 12/512,964, mailed Apr. 24, 2012 (5 pages).

*Primary Examiner* — Amy Bowman
(74) *Attorney, Agent, or Firm* — Fish & Richardson P.C.

(57) ABSTRACT

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features, inter alia, nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker.

16 Claims, 20 Drawing Sheets

FIG. 6A

```
3301 cttgtgtact gtgttggcca cctaaaactc tttgcattga gtaaaattct aattgccaat
3361 aatcctaccc attggattag acagcactct gaaccccatt tgcattcagc aggggggtcgc
3421 agacaaccog tctttgttg gacagttaaa atgctcagtc ccaattgtca tagctttgcc
3481 tattaaacaa aggcaccgta ctgcgctttt tgctgtgctt ctggagaatc ctgctgttct
3541 tggacaatta aagaacaaag tagtaattgc taattgtctc accattaat catgaagct
3601 accagtcgcc cttgcatttg ccttgaggca gcgctgacta cctgagattt aagagtttct
3661 taaattattg agtaaaatcc caattatcca tagttctgtt agttacacta tgccttttgc
3721 aaacatcttt gcataacagc agtgggactg actcattctt agagccoctt cccttggaat
3781 attaatggat acaatagtaa ttattcatgg ttctgcgtaa cagagaagac ccacttatgt
3841 gtatgcattt atcattgctc ctagatagtg tgaactacct accaccttgc attaatatgt
3901 aaaacactaa ttgcccatag tcccactcat tagtctagga tgtcctcttt gccattgctg
3961 ctgagttctg actacccaag tttccttctc ttaaacagtt gatatgcata attgcatata
4021 ttcatggttc tgtgcaataa aaatggattc tcaccccatc ccacttctg tgggatgttg
4081 ctaacgagtg cagattattc aataacagct ctgaacagt taatttgcac agttgcaatt
4141 gtccagagtc ctgtccatta gaaagggact ctgtatccta tttgcacgct acaatgtggg
4201 ctgatcaccc aaggactctt ctgtgcatt gatgttcata attgtatttg tccacgatct
4261 tgtgcactaa cccttccact ccctttgtat tccagcaggg gaccttact actcaagacc
4321 tctgtactag gacagtttat gtgcacaatc ctaattgatt agaactgagt cttttatatc
4381 aagtccctg catcatcttt gctttacatc aagagggtgc tggttaccta atgcccctcc
4441 tccagaaatt attgatgtgc aaaatgcaat ttccctatcc gctgttagtc tggggtctca
4501 tccctcata ttcctttgt cttacagcag gggtacttg ggactgttaa tgcgcataat
4561 tgcaattatg gtcttttcca ttaaattaag atcccactg ctcacaccct cttagcatta
4621 cagtagaggg tgctaatcac aaggacattt cttttgtact gttaatgtgc tacttgcatt
4681 tgtccctctt cctgtgcact aaagacccca ctcacttccc tagtgttcag cagtggatga
4741 cctctagtca agaccttgc actaggatag ttaatgtgaa ccatggcaac tgatcacaac
4801 aatgtctttc agatcagatc catttatcc tccttgtttt acagcaaggg atattaatta
4861 cctatgttac ctttcctgg gactatgaat gtgcaaaatt ccaatgttca tggtctctcc
4921 ctttaaacct atattctacc ccttttacat tatagaaagg gatgctggaa acccagagtc
4981 ctttctctgg gactcttaat gtgtatttct aattatccat gactcttaat gtgcatattt
5041 tcaattgcct aatgatttc aatgtctaa gacatttcaa atgtctaatt gattagaact
5101 gagtctttta tatcaagcta atatctagct tttatatcaa gctaatatct tgactttctca
5161 gcatcataga aggggtact gattcctaa agtctttctt gaattctat tatgcaaaat
5221 tgcoctgagg ccggtgtgg tgctcacac ctgtaatccc agcactttgg gaggctgagg
5281 tggaagatc cttactgcc aggagtttga gaccagcctg gcaacatta aaaaaaaaaa
5341 aaaaagtaag acaattgccc tggaatccca tcccctcac acctccttgg caaagcagca
5401 ggagtgctaa ctagctagtg cttcttctct tataccgctt aaatgcgcat aattagcagt
5461 agtgatgtg ccctatgtt agagtagaat cccgcttcct tgctccattt gcattactgc
5521 aggagcttat aactagcctg aattcactct cttggactgt taatgtgcat acttatattt
5581 gctgctgtac tttttaccca tgtaaggacc ccaccactg tatttacatc ccagctggaa
5641 gtacctacta cttaagaccc ttagactagt aaagttagcg tgcataatct taggtgttat
5701 atacacattt tcagttgcat acagttgtgc cttttatcag gactcctgta cttatcaaag
5761 cagagagtgc taatcaatat taagccttc tcttcgaact gtagatggca tgtaattgca
5821 gttgtcaatg gtccttcaat tagactaggg tttctgacct atcacaccct ctttgcttta
5881 ttgcatgggg tactattcac ttaaggccca tttctcaaac tgttaatgtg cctaatgaca
5941 attacatcag tatccttcct tttgaaggac agcatggttg gtgacaccta aggcccatt
6001 tcttggcctc ccaatatgtg tgattgtatt tgtcgaggtt gctatgcact agagaaggaa
6061 agtgctcccc tcatcccac tttctccttc cagcaggaag tgcccaccca ataagaccct
6121 tttatttgga gagtctaggt gcacaattgt aagtgaccac aagcatgcat cttggacatt
6181 tatgtgcgta atgcacact gctcattcca tgtgaataag gtcctactct ccgacccctt
6243 ttgcaataca gaagggttgc tgataacgca gtccccttt cttggcatgt tgtgtgtgat
6301 tataatcgtc tgggatccta tgcactagaa aaggagggtc ctctccacat acctcagtct
6361 caccttccc ttccagcagg gagtgcccac tccataagac tctcacattt ggacagtcaa
6421 ggtgcgtaat tgttaagtga acacaaccat gcaccttaga catggatttg cataactaca
6481 cacagtcaa cctatctgaa taaaatccta ctctcagacc cctttgcag tacagcaggg
6541 gtgctgatca ccaaggccct tttcctggc ctggatgcg tgtgattatg tttgtccggg
```

FIG. 6B

```
6601 ttcctgtgta ttagacatgg aagcctccc tgccacactc caccccaat cttcctttcc
6661 cttccggcag gagtgccctc tccataagac gcttacgttt ggacaatcaa ggtgcacagt
6721 tgtaagtgac cacaggcata caccttggac attaatgtgc ataaccactt tgcccattcc
6781 atctgaataa ggtcctactc tcagaccct tttgcagtac agcaggggtg ctgatcacca
6841 aggcccttt tcttggcctg ttatgtgcgt gattatattt gtctggttc ctgtgtatta
6901 gacaaggaag ccttcccccc gccccacc ccactcccag tcttccttc ccttccagca
6961 gggagtgccc cctccataag atcattacat tggacaatc aaggtgcaca attataagtg
7021 accacagcca tgcaccttgg acattattgg acattaatgt ggtaactgc acatggccca
7081 tccatctga ataaggacct actctcagat gccttgcag tacagcaggg gtactgaatc
7141 accaggccc tttctggg cctgttatgt gtgtgattat atttatccca gtttctgtgt
7201 aatagacatg aaagcctccc ctgccacacc ccactccaa tcttcctttc ccttccacca
7261 gggagtgtcc actccatata cccttacatt tggacaatca aggtgcacaa ttgtaagtga
7321 gcataggcac tcaccttgga catgaatgtg cataactgca catggcccat ccatctgaa
7381 taaggtccta ctctcagacc cttttgcag tacagcaggg gtgctgatca ccaaggcccc
7441 tttcctggc ctgttatgtg tgtgattata tttgttccag ttcctgtgta atagacatgg
7501 aagcctccc tgccacactc caccccaat cttcctttcc ttctggcagg aagtacccgc
7561 tccataagac ccttacattt ggacagtcaa ggtgcacaat tgtatgtgac cacaaccatg
7621 caccttggac ataaatgtgt gtaactgcac atggcccatc ccatctgaat aaggtcctac
7681 tctcagaccc cttttgcagt acagtaggtg tgctgataac caaggcccct cttcctggcc
7741 tgttaagta tgtgattata tttgtctggg ttccagtgta taagacatgg aagcctccc
7801 tgccccacc cacctcaat cttcctttcc cttctggcag ggagtgcaag ctccataaga
7861 accttacatt tggacagtca aggtgcacaa ttctaagtga ccgcagccat gcaccttggt
7921 caataatgtg tgtaactgca cacggcctat ctcatctgaa taaggcctta ctctcagacc
7981 cttttgcag tacagcaggg gtgctgataa ccaaggccca ttttcctggc ctgttatgtg
8041 tgtgattata tttgtccagg tttctgtgta ctagacaagg aagcctcctc tgccccatcc
8101 catctacgca taatctttct ttcctccca gcagggagtg ctcactccat aagacccta
8161 catttggaca atcaaggtgc acaattgtaa gtgaccacaa ccatgcatct tggaaattta
8221 tgtgcataac tgcacatggc ctatcctatt tgaataaagt cctactctca gacccccttt
8281 gcagtatagc tggggtgctg atcactgagg cctctttgct tggcttgtct atattcttgt
8341 gtactagata agggcacctt ctcatggact ccctttgctt tcagcaagg agtacccact
8401 acttttaag attcttatat ttgtccaag tacatggttt taattgacca caccaatgtc
8461 cctggacat taatgtatgt aatcaccaca tggttcatcc taattaaca aagttctacc
8521 ttctcaccct ccatttgcag tataccaggg ttgctgaccc cctaagtccc ctttttcttgg
8581 cttgttgaca tgcataattg cattatgtt ggttcttgtg ccctagacaa ggatgcccca
8641 cctcttttca atagtgggtg cccactcctt atgatcttta cattgaaca gttaatgtga
8701 ataattgcag ttgtccacaa ccctatcact tctaggacca ttatacctct tttgcattac
8761 tgtgggtat actgtttccc tccaaggccc cttctggtgg actatcaaca tataattgaa
8821 atttctttt gtctttgtca gtagattaag gtcatacccc atcacctttc ctttgtagta
8881 caacagggtg tcctgatcaa ccaaagtcct gttgtttgg actgttaata tgtgcaatta
8941 cattgctcc tgatctgtgc actagataag gatcctacct acttcttag tgttttagc
9001 aggtagtgcc cactactcaa gactgtcact tggaatgttc atgtgcacaa actcaattct
9061 ctaagcatgt tcctgtacca ccttgctt agagcagggg gatgatattc actaagtgcc
9121 cctcttttg gacttaatat gcattaatgc aattgtccac ctctctttt agactaagag
9181 ttgatctcca catattcccc ttgcatcagg ggcatgttaa ttatgaatga acccttttct
9241 tttaatatta atgtcataat tgtattgtg gacctgtgta ggagaaaag acccatgtt
9301 cctcccatta ccctttggat tgctgctgag aagtgttaac tactcataat ctcagctctt
9361 ggacaattaa tagcattaat aacaattatc aagggcactg atcattagat aagctcctg
9421 cttcctgtt gctacatcg gggtactga cccactaagg cccttgtac tgttaatgtg
9481 aatatttgca attatatg tctccttctg gtagagtggg atattatgcc ctagtatccc
9541 ctttgcatta ctgcagggc tgctgactac tcaaaacttc tcctgggact gttaataggc
9601 acaatggcag ttatcaatgg ttttctcct cctgacctt gttaagcaag cgccccaccc
9661 cacccttagt ttcccatggc ataataaagt ataagcattg gagtattcca tgcacttgtc
9721 tataaaacag tggtccatac tccaaccct tttgcattgc gccagtgtgt aaaatcacag
9781 gtagccatgg tgtcatgctt tatataggaa gtcttccctc tctctgccc ttgtgtgccc
9841 ttggcccctt ttacagact attgctcaca atctcaggtg tccatatttg cagctattag
```

FIG. 6C

```
 9901 gtaagattgt gctgtctccc tcttccctct cctctgcct gccctttg cctctttgct
 9961 gggtaatgtt gaccagacaa ggcccttct cttggactta aacaattctc agttgcactt
10021 tccttgtcc accattata catgaaccca tctacttcct ttcgcattgc ttctgagtat
10081 gctgactacc caaagcccct tctgtgttat taataaacac agtactgatt gtcccatttt
10141 tcagcccatc agtccaagat ctccctacca cttggtgtg ttggtgcagt gttgactatg
10201 aaaagcaggc ctgaactagg tggataagcc ttcactcatt ttctttcatt tattaatgat
10261 cctagtttca attattgtca gattctgggg acaagaacca ttcttgccca cctgtgttac
10321 tgctttactg tgcaaaatac tgaaggcaag tcagcccag ggagctggat tgccatcctt
10381 tatttgtgt ttccagtgta cactataaaa ttgtctccc aggaaggaag gttggcactt
10441 tctctgcatt cttctttcca gagcagattg cctggtaag aatctcttgt tgtcccttct
10501 gtatattgtt atgtaaagt gccaaatgcc aggatacagc cagaaaaatt gcttattatt
10561 attaaaaaaa tttttttaag aaagacatct ggattgtagg gtggactcga taacctggtc
10621 attattttt tgaagccaaa atatccattt atactatgta cctggtgacc agtgtctctc
10681 atttttaactg agggtggtgg gtctgtggat agaacactga ctcttgctat tttaatatca
10741 aagatattct agagtggaac tcttaagacc agtatctttg tgtgggcttt accagcattc
10801 acttttagaa aaactaccta aattttataa tccttttaatt tcttcatctg gagcacctgc
10861 ccctacttat ttcaagaaga ttgcagtaaa acgattaaat gagggaacat atgcagaggt
10921 gcttttaaaa agcatatgcc accttttta ttaattatta tataaaatga agcatttaat
10981 tatagtaata atttgaagta gtttgaagta ccacactgag gtgaggactt aaaaatgata
11041 agacgagttc cctattttat aagaaaaata agccaaaatt aaatattctt ttggatataa
11101 atttcaacag tgagatagct gcctagtgga aatgaataat atcccagcca ctagtgtaca
11161 gggtgttttg tggcacagga ttatgtaata tggaactgct caagcaaata actagtcatc
11221 acaacagcag ttcttgtaa taactgaaaa agaatattgt ttctcgaga aggatgtcaa
11281 aagatcggcc cagctcaggg agcagtttgc cctactagct cctggacag ctgtaaagaa
11341 gagtctctgg ctctttagaa tactgatccc attgaagata ccagctgca tgtgtcctta
11401 gtagtcatgt ctccttaggc tcctcttgga cattctgagc atgtgagacc tgaggactgc
11461 aaacagctat aagaggctcc aaattaatca tatctttccc tttgagaatc tggccaagct
11521 ccagctaatc tacttggatg ggttgccagc tatctggaga aaagatctt cctcagaaga
11581 ataggcttgt tgttttacag tgttagtgat ccattccctt tgacgatccc taggtggaga
11641 tggggcatga ggatcctcca ggggaaaagc tcactaccac tgggcaacaa ccctaggtca
11701 ggaggttctg tcaagataet ttcctggtcc cagataggaa gataaagtct caaaaacaac
11761 caccacacgt caagctcttc attgttccta tctgccaaat cattatactt cctacaagca
11821 gtgcagagag ctgagtcttc agcaggtcca agaaatttga acacactgaa ggaagtcagc
11881 cttcccaact gaagatcaac atgcctggca ctagacct tgaggatagc tgaatgaatg
11941 tgtatttctt tgtctcttc ttttttgtct ttgctctttg ttctctatct aaagtgtgtc
12001 ttacccattt ccatgtttct cttgctaatt tctttcgtgt gtgccttgc ctcatttct
12061 cttttgttc acaagagtgg tctgtgtctt gtcttagaca tatctctcat ttttcatttt
12121 gttgctattt ctctttgctc tcctagatgt ggctcttctt tcacgcttta tttcatgtct
12181 cctttttggg tcacatgctg tgtgctttt gtccttttct tgttctgtct acctctcctt
12241 tctctgccta cctctcttt ctctttgtga actgtgatta tttgttaccc cttcccttc
12301 tcgttcgttt taaattccac cttttttctg agtctggcct cctttctgct gtttctactt
12361 tttatctcac atttctcatt tctgcatttc cttctgcct ctcttgggct attctctctc
12421 tcctccactg cgtgcctcag catctcttgc tgtttgtgat tttctattc agtattaatc
12481 tctgttggct tgtattgtt ctctgcttct tcctttcta ctcacctttg agtatttcag
12541 cctcttcatg aatctatctc cctctctttg atttcatgta atctctcctt aaatattct
12601 ttgcatatgt gggcaagtgt acgtgtgt gtgtcatgtg tggcagaggg gcttcctaac
12661 ccctgactga taggtgcaga acgtggcta tcagagcaag cattgtggag cggttcctta
12721 tgccaggctg ccatgtgaga tgatccaaga ccaaacaag gcctagact gcagtaaaac
12781 ccagaactca agtagggcag aaggtggaag gctcatatgg atagaaggcc caagtataa
12841 gacagatggt ttgagacttg agacccgagg actaagatgg aaagccatg ttccaagata
12901 gatagaagcc tcaggcctga aacaacaaa agcctcaaga gccaagaaaa cagagggtgg
12961 cctgaattgg accgaaggcc tgagttggat ggaagtctca aggcttgagt tagaagtctt
13021 aagacctggg acaggacaca tggaaggcct aagaactgag acttgtgaca caaggccaaac
13081 gacctaagat tagcccaggg ttgtagctgg aagacctaca acccaaggat ggaaggccc
13141 tgtcacaaag cctacctaga tggatagagg acccaagcga aaaggtatc tcaagactaa
```

FIG. 6D

```
13201 cggcggaat ctggaggcc atgaccaga accaggaag gatagaagct tgaagacctg
13261 gggaatccc aagatgagaa ccctaaaccc tacctctttt ctatgtttta cacttcttac
13321 tcttagatat ttccagttct cctgtttatc tttaagcctg attcttttga gatgtacttt
13381 ttgatgttgc cggttacctt tagattgaca gtattatgcc tgggccagtc ttgagccagc
13441 tttaaatcac agcttttacc tattgttag gctatagtgt tttgtaaact tctgtttcta
13501 ttcacatctt ctccacttga gagagacacc aaaatccagt cagtatctaa tctggctttt
13561 gttaacttcc ctcaggagca gacattcata taggtgatac tgtatttcag tcctttctt
13621 tgacccaga gccctagac tgagaagata aaatggtcag gttgttgggg aaaaaaaag
13681 tgccaggctc tctagagaaa aatgtgaaga gatgctccag gccaatgaga agaattagac
13741 aagaaataca cagatgtgcc agacttctga gaagcacctg ccagcaacag cttccttctt
13801 tgagcttagg tgagcaggat tctggggttt gggatttcta gtgatggtta tggaaagggt
13861 gactgtgcct gggacaaagc gaggtcccaa gggacagcc tgaactccct gctcatagta
13921 gtggccaaat aatttggtgg actgtgccaa cgctactcct gggttaata cccatctcta
13981 ggcttaaaga tgagagaacc tgggactgtt gagcatgttt aatactttcc ttgatttttt
14041 tcttcctgtt tatgtgggaa gttgatttaa atgactgata atgtgatga aagcactgta
14101 aaacataaga gaaaaaccaa ttagtgtatt ggcaatcatg cagttaacat ttgaaagtgc
14161 agtgtaaatt gtgaagcatt atgtaaatca gggtccaca gttttctgt aagggtcaa
14221 atcataaata ctttagactg tgggccatat ggtttctgtt acatattgt tttttaaaca
14281 acgtttttat aaggtcaaaa tcattcttag ttttgagcc aattggattt ggctgctgt
14341 tcatagctta ccaccctg atgtattatt tgttattcag agaaaattc tgaatactac
14401 tagtttcctt ttctgtgcct gtccctgtgc taggcactaa aaatgcaatg attattgata
14461 tctaggtgac ctgaaaaaaa atagtgaatg tgctttgtaa actgtaaagc acttgtattc
14521 tactgtgata agcgttgtgg atacaaagaa aggagcaagc ataaaaaagt gctctttcaa
14581 aaggatatag tactatgcag acacaaggaa ttgtttgata aatgaataaa ttatatgtat
14641 atttgaggcc aatttgtgtt tgctgctctg gtaattttga gtaaaaatgc agtattccag
14701 gtatcagaaa cgaaaacaca tggaaactgc tttttaaactt taaaatatac tgaaaacata
14761 agggactaag cttgttgtgg tcacctataa tgtgccagat accatgctgg gtgctagagc
14821 taccaaaggg ggaaaagtat tctcatagca acaaaaaatt tcagaaaggt gcatattaaa
14881 gtgcttgta aactaaagca tgatacaaat gtcaatgggc tacatattta tgaatgaatg
14941 aatggatgaa tgaatattaa gtgcctctta cataccagct attttgggta ctgtaaaata
15001 caagattaat tctcctatgt aataagagga aagtttatcc tctatactat tcagatgtaa
15061 ggaatgatat attgcttaat tttaaacaat caagactta ctggtgaggt taagttaaat
15121 tattactgat acatttttcc aggtaaccag gaaagagcta gtatgaggaa atgaagtaat
15181 agatgtgaga tccagaccga aagtcacta attcagcttg cgaatgtgct ttctaaatta
15241 taaagcactt gtaaatgaaa aatttgatgc tttctgtatg aataaaactt tctgtaagct
15301 aggtatttgtc tctacaaaat tctcattgta tagttaaacc acagtgagaa gggttctata
15361 agtagttata caaaccaagg gttaaatac ctgttaaata gatcaatttt gattgcctac
15421 tatgtgaact cactgttaaa ggcactgaaa attatcata tttcatttag ccacagccaa
15481 aaataaggca atacctatgt tagcattttg tgaactctaa ggcaccatat aaatgtaact
15541 gttgatttc tcacttggtg ctgggtacta ggtttataaa attgtatgat agttattata
15601 ttgtgcaaat aaagtaggaa aatttgaata acaatgatta tctttgaat acgcatacgc
15661 aagggattgg ttgtctgaag aatgccacta tagtagttat ctattgtgtg ccaatctcat
15721 tgctaggcat tggggatgca aagataaacc atcttattg tgtctgggt agcagaagaa
15781 aatatgtgta aaatcaattt ataatttgta aactgccacc catatataag ctatatctgc
15841 tgaatgatca ttgattactc ttatccttag agataacaac tggggcaca aacattatt
15901 atcattattg aacctacaac agagatctat gtgtagattt acgaagccta cagttctata
15961 cagataggaa tgaactattg gttactgaa tgtgattac tttctgtggg gctcggaact
16021 acatgccta ggatataaaa atgatgttat cattatagag tgctcacaga aggaaatgaa
16081 gtaatatagg tgtgagatcc agaccaaaag ttatttaaca gtttattca gtgatgaaaa
16141 catggacaa atggactata taaggcagtg tactaagctg agtagagaga taaagtcctg
16201 tccagaagat acatgctttc ctggcctgat tgaggagatg gaaattttt gcaaaaaca
16261 aggtgttgt ggtcttccat ccagttctt aagtgctgat gataaaagtg aattagaccc
16321 accttgacct ggcctacaga agtaaggag taaaaataaa tgctcaggc gtgcttttg
16381 attcattga taaacaaagc atctttatg tggaatatac cattctgggt cctgaggata
16441 agagagatga gggcattaga tcactgacag ctgaagatag a   (SEQ ID NO:1)
```

FIG. 6E

```
   1 cttcagttct taaagcgctg caattcgctg ctgcagccat atttcttact ctctggggc
  61 tggaagcttc ctgactgaag atctctctgc actggggtt ctttctagaa cattttctag
 121 tccccaaca ccctttatgg cgtatttctt taaaaaatc acctaaattc cataaaatat
 181 ttttttaaat tctatacttt ctcctagtgt cttcttgaca cgtcctccat attttttaa
 241 agaaagtatt tggaatattt tgaggcaatt tttaatattt aaggaatttt tctttggaat
 301 cattttggt tgacatctct gttttttgtg gatcagtttt ttactcttcc actctcttt
 361 ctatatttg cccatcgggg ctgcggatac ctggttttat tattttttct ttgcccaacg
 421 gggccgtgga tacctgcctt taattcttt tttattcgcc catcggggcc cgggatacct
 481 gctttttatt ttttttcct tagcccatcg gggtatcgga tacctgctga ttcccttccc
 541 ctctgaaccc ccaacactct ggcccatcgg ggtgacggat atctgctttt taaaaatttt
 601 cttttttgg cccatcgggg cttggatac ctgcttttt tttttttatt tttccttgcc
 661 catcggggcc tggatacct gctttaattt ttgtttttct ggcccatcgg ggccgcggat
 721 acctgctttg attttttttt ttcatcgccc atcggtgctt tttatggatg aaaaaatgtt
 781 ggtttgtgg gttgttgcac tctctggaat atctacactt tttttgctg ctgatcattt
 841 ggtggtgtgt gagtgtacct accgctttgg cagagaatga ctctgcagtt aagctaaggg
 901 cgtgtcaga ttgtggagga aaagtggccg ccatttaga cttgccgcat aactcggctt
 961 agggctagtc gtttgtgcta agttaaacta gggaggcaag atggatgata gcaggtcagg
1021 cagaggaagt catgtgcatt gcatgagcta aacctatctg aatgaattga tttggggctt
1081 gttaggagct tgcgtgatt gttgtatcgg gaggcagtaa gaatcatctt ttatcagtac
1141 aagggactag ttaaaaatgg aaggttagga aagactaagg tgcagggctt aaaatggcga
1201 ttttgacatt gcggcattgc tcagcatggc gggctgtgct ttgttaggtt gtccaaaatg
1261 gcggatccag ttctgtcgca gtgttcaagt ggcgggaagg ccacatcatg atgggcgagg
1321 ctttgttaag tggttagcat ggtggtggac atgtgcggtc acacaggaaa agatggcggc
1381 tgaaggtctt gccgcagtgt aaaacatggc gggcctcttt gtctttgctg tgtgctttc
1441 gtgttgggtt ttgccgcagg acaatatgg caggcgttgt catatgtata tcatggcttt
1501 tgtcacgtgg acatcatggc gggcttgccg cattgttaaa gatggcgggt tttgccgcct
1561 agtgccacgc agagcgggag aaaaggtggg atggacagtg ctggattgct gcataaccca
1621 accaattaga aatggggtg gaattgatca cagccaatta gagcagaaga tggaattaga
1681 ctgatgacac actgtccagc tactcagcga agacctgggt gaattagcat ggcacttcgc
1741 agctgtcttt agccagtcag gagaaagaag tggagggcc acgtgtatgt ctccagtgg
1801 gcggtacacc aggtgttttc aaggtctttt caaggacatt tagcctttcc acctctgtcc
1861 cctcttattt gtccctcct gtccagtgct gctcttgca gtgctggata tctggctgtg
1921 tggtcgaac ctccctccat tcctctgtat tggtgcctca cctaaggcta agtataccct
1981 ccccccacc cccaaccc ccaactccc caccccacc cccacccccc cacctcccca
2041 cccccctacc cccctaccc cctacccccc tctggtctgc cctgcactgc actgttgcca
3101 tggcagtgc tccaggctg ctggtgtgg acatggtggt gagccgtggc aaggaccaga
2161 atggatcaca gatgatcgtt ggccaacagg tgcagaaga ggaattcctg cctcctcaa
2221 gaggaacacc tacccttgg ctaatgctgg ggtcggattt tgatttatat ttatcttttg
2281 gatgtcagtc atacagtctg attttgtggt ttgctagtgt ttgaatttaa gtcttaagtg
2341 actattatag aaatgtatta agaggcttta tttgtagaat tcactttaat tacatttaat
2401 gagttttgt tttgagttcc ttaaaattcc ttaaagtttt tagcttctca ttacaaattc
2461 cttaaccttt ttttggcagt agatagtcaa agtcaaatca tttctaatgt tttaaaaatg
2521 tgctggtcat tttctttgaa attgacttaa ctatttcct ttgaagagtc tgtagcacag
2581 aaacagtaaa aaatttaact tcatgaccta atgtaaaaaa gagtgtttga aggtttacac
2641 aggtccaggc ctgcttgt tccatcctt gatgctgcac taattgacta atcacctact
2701 tatcagacag gaaacttgaa ttgctgtggt ctggtgtcct ctattcagac ttattatatt
2761 ggagtattc aatttcgt tgtatcctgc ctgcctagca tccagttcct cccagcctt
2821 gctcccagca aacccctagt ctagccccag ccctactccc accccgccc agccctgccc
2881 cagcccagt ccctaaccc ccagccccta gcccagtcc cagtcctagt tctccagtcc
2941 cgccagctt ctctcgaaag tcactctaat tttcattgat tcagtgctca aaataagttg
3001 tccattgctt atcctattat actgggatat tccgttaccc cttggcattg ctgatcttca
3061 gtactgactc cttgaccatt ttcagttaat gcatacaatc ccattgtct gtgatctcag
3121 gacaaagaat ttcctactc ggtacgttga agttagggaa tgtcaattga gagctttcta
3181 tcagagcatt attgccaca atttgagtta cttatcattt tctcgatccc ctgcccttaa
3241 aggagaaacc attttctctgt cattgcttct gtagtcacag tcccaatttt gagtagtgat
```

FIG. 7A

```
3301 cttttcttgt gtactgtgtt ggccacctaa aactctttgc attgagtaaa attctaattg
3361 ccaataatcc tacccattgg attagacagc actctgaacc ccattgcat tcagcagggg
3421 gtcgcagaca acccgtcttt tgttggacag ttaaaatgct cagtcccaat tgtcatagct
3481 ttgcctatta aacaaggca ccctactgcg cttttgctg tgcttctgga gaatcctgct
3541 gttcttggac aattaaagaa caagtagta attgctaatt gtctcaccca ttaatcatga
3601 agactaccag tcgccettgc attttgccttg aggcagcgct gactacctga gattaagag
3661 tttcttaaat tattgagtaa aatcccaatt atccatagtt ctgttagtta cactatgcc
3721 tttgcaaaca tctttgcata acagcagtgg gactgactca ttcttagagc ccttcccctt
3781 ggaatattaa tggatacaat agtaattatt catggttctg cgtaacagag aagaccccact
3841 tatgtgtatg ccttttatcat tgctcctaga tagtgtgaac tacctaccac cttgcattaa
3901 tatgtaaaac actaattgcc catagtccca ctcattagtc taggatgtcc tctttgccat
3961 tgctgctgag ttctgactac ccaagtttcc ttctcttaaa cagttgatat gcataattgc
4021 atatattcat ggttctgtgc aataaaaatg gattctcacc ccatcccacc ttctgtggga
4081 tgttgctaac gagtgcagat tattcaataa cagctcttga acagttaatt tgcacagttg
4141 caattgtcca gagtcctgtc cattagaaag ggactctgta tcctatttgc acgctacaat
4201 gtgggctgat cacccaagga ctcttcttgt gcattgatgt tcataattgt atttgtccac
4261 gatcttgtgc actaacctt ccactccctt tgtattccag cagggaccc ttactactca
4321 agacctctgt actaggacag tttatgtgca caatcctaat tgattagaac tgagtcttttt
4381 atatcaaggt ccctgcatca tcttttgcttt acatcaagag ggtgctggtt acctaatgcc
4441 cctcctccag aaattattga tgtgcaaaat gcaatttccc tatctgctgt tagtctgggg
4501 tctcatcccc tcatattcct tttgtcttac agcaggggt actgggact gttaatgcgc
4561 ataattgcaa ttatggtctt ttccattaaa ttaagatccc aactgctcac ccctcttag
4621 cattacagta gagggtgcta atcacaagga catttctttt gtactgttaa tgtgctactt
4681 gcattgtcc ctcttcctgt gcactaaaga ccccactcac ttccctagtg ttcagcagtg
4741 gatgaccctct agtcaagacc tttgcactag gatagttaat gtgaaccatg gcaactgatc
4801 acaacaatgt ctttcagatc agatccattt tatcctcctt gttttacagc aagggatatt
4861 aattacctat gttaccttttc cctgggacta tgaatgtgca aaattccaat gttcatggtc
4921 tctccccttta aacctatatt ctacccctttt tacattatag aaagggatgc tggaaaccca
4981 gagtccttct ctgggactc ttaatgtgta tttctaatta tccatgactc ttaatgtgca
5041 tatttcaat tgcctaattg atttcaattg tctaagacat ttcaaatgtc taattgatta
5101 gaactgagtc ttttatatca agctaatatc tagcttttat atcaagctaa tatcttgact
5161 tctcagcatc atagaagggg gtactgattt cctaaagtct ttcttgaatt tctattatgc
5221 aaaattgccc tgaggccggg tgtggtggct cacacctgta atcccagcac ttgggaggc
5281 tgaggtggga agatcccttta ctgccaggag ttgagacca gcctggccaa cattaaaaaa
5341 aaaaaaaagt aagacaattg ccctggaatc ccatccccct cacacctcct tggcaaagca
5401 gcaggagtgc taactagcta gtgcttcttc tcttatactg cttaaatgcg cataattagc
5461 agtagttgat gtgccccctat gttagagtag aatcccgctt ccttgctcca tttgcattac
5521 tgcaggagct tctaactagc ctgaattcac tctcttggac tgttaatgtg catacttata
5581 tttgctgctg tactttttta ccatgtaagg accccaccca ctgtatttac atcccagctg
5641 gaagtaccta ctacttaaga cccttagact agtaaagtta gcgtgtcataa tcttaggtgt
5701 tatatacaca ttttcagttg catacagttg tgcctttat caggactcct gtacttatca
5761 aagcagagag tgctaatcaa tattaagccc ttctcttcga actgtagatg gcatgtaatt
5821 gcagttgtca atggtccttc aattagactt gggtttctga cctatcacac cctctttgct
5881 ttattgcatg gggtactatt cacttaaggc cccttttctca aactgttaat gtgcctaatg
5941 acaattacat cagtatcctt cctttttgaag gacagcatgg ttggtgacac ctaaggcccc
6001 attcttggc ctcccaatat gtgtgattgt atttgtcgag gttgctatgc actagagaag
6061 gaaagtgctc ccctcatccc cactttccc ttccagcagg aagtgccac cccataagac
6121 cctttattt ggagagtcta ggtgcacaat tgtaagtgac cacaagcatg catcttggac
6181 atttatgtgc gtaatcgcac actgctcatt ccatgtgaat aaggtcctac tctccgaccc
6241 cttttgcaat acagaagggt tgctgataac gcagtccct ttctttggca tgttgtgtgt
6301 gattataatc gtctgggatc ctatgcacta gaaaaggag gtcctctcca catcctcag
6361 tctcaccttt ccctttccagc agggagtgcc cactccataa gactctcaca tttggacagt
6421 caaggtgcgt aattgttaag tgaacacaac catgcacctt agacatggat ttgcataact
6481 acacacagct caacctatct gaataaaatc ctactctcag accccttttg cagtacagca
6541 ggggtgctga tcaccaaggc cctttttcct ggcctggtat gcgtgtgatt atgtttgtcc
```

FIG. 7B

```
6601 cggttcctgt gtattagaca tggaagcctc ccctgcaca ctccacccc aatcttcctt
6661 tccttccgg cagggagtgc cctctccata agacgcttac gtttggacaa tcaaggtgca
6721 cagttgtaag tgaccacagg catcacctt ggacattaat gtgcataac actttgccca
6781 ttccatctga ataaggtcct actctcagac cccttttgca gtacagcagg ggtgctgatc
6841 accaaggcc cttttcttgg cctgttatgt ggtgattat atttgtctgg gttcctgtgt
6901 attagcaag gaagccttcc cccgcccc accccactc ccagtcttcc tttccttcc
6961 agcagggagt gccccctcca taagatcatt acatttggac aatcaaggtg cacaattata
7021 agtgaccaca gccatgcacc ttggacatta ttggacatta atgtgcgtaa ctgcacatgg
7081 cccatcccat ctgaataagg tcctactctc agatgcctt tgcagtacag cagggtact
7141 gaatcaccaa ggccctttt cttggcctgt tatgtgtgtg attatattta tccagttc
7201 tgtgtaatag acatgaaagc ctccctgcc acacccacc tccaatcttc ctttccttc
7261 caccagggag tgtccactcc atatccctt acatttggac aatcaaggtg cacaattgta
7321 agtgagcata ggcactcacc ttggacatga atgtgcataa ctgcacatgg cccatcccat
7381 ctgaataagg tcctactctc agacccttt tgcagtacag cagggtgct gatcaccaag
7441 gcccttttc ctggcctgtt atgtgtgtga ttatatttgt tccagttcct gtgtaataga
7501 catggaagcc tccctgcca cactccaccc ccaatcttcc tttccttct ggcaggaagt
7561 acccgtcca taagacccttt acatttggac agtcaaggtg cacaattgta tgtgaccaca
7621 accatgcacc ttggacataa atgtgtgtaa ctgcacatgg cccatcccat ctgaataagg
7681 tcctactctc agacccttt tgcagtacag taggtgtgct gataaccaag gcccctcttc
7741 ctggcctgtt aacgtatgtg atatatttg tctgggttcc agtgtataag acatggaagc
7801 ctccctgcc ccacccacc ctcaatcttc ctttccttc tggcaggag tgccagctcc
7861 ataagaacct tacatttgga cagtcaaggt gcacaattct aagtgaccgc agccatgcac
7921 cttggtcaat aatgtgtgta actgcacacg gctatctca tctgaataag gccttactct
7981 cagacccctt ttgcagtaca gcaggggtgc tgataaccaa ggcccatttt cctggcctgt
8041 tatgtgtgtg attatatttg tccaggtttc tgtgtactag acaaggaagc ctcctctgcc
8101 ccatccatc tacgcataat ctttcttttc ctcccagcag ggagtgctca ctccataaga
8161 ccttacatt tggacaatca aggtgcacaa ttgtaagtga ccacaaccat gcatcttgga
8221 aatttatgtg cataactgca catggcttat cctatttgaa taaagtccta ctctcagacc
8281 cccttttgcag tatagctggg gtgctgatca ctgaggcctc tttgcttggc ttgtctatat
8341 tcttgtgtac tagataaggg cacctcctca tggacctcct ttgcttttca acaaggagta
8401 cccactactt tttaagattc ttatattgt ccaagtaca tggttttaat tgaccacaac
8461 aatgtccctt ggcattaat gtatgtaatc accacatggt tcatcctaat taaacaaagt
8521 tctacttct cacctccat ttgcagtata ccagggttgc tgaccccta agtccccttt
8581 tcttggcttg ttgacatgca taattgcatt tatgttggtt cttgtgccct agacaaggat
8641 gccccactc ttttcaatag tgggtgccca ctcctatga tctttacatt tgaacagtta
8701 atgtgaataa ttgcagttgt ccacaaccct atcacttcta ggaccattat acctcttttg
8761 cattactgtg gggtatactg ttttcctcca aggcccttc tggtggacta tcaacatata
8821 attgaaattt tctttttgtct ttgtcagtag attaaggtca tacccccatca ccttcctt
8881 gtagtacaac agggtgtcct gatcaaccaa agtcctgttg tttggactg ttaatatgtg
8941 caattacatt tgctcctgat ctgtgcacta gataaggatc ctacctactt tcttagtgtt
9001 tttagcaggt agtgcccact actcaagact gtcacttgga atgttcatgt gcacaaactc
9061 aattctctaa gcatgttcct gtaccaccttt tgctttagag caggggatg atattcacta
9121 agtgcccctt cttttggact taatatgcat taatgcaatt gtccacctct tcttttagac
9181 taagagttga tctccacata ttccccttgc atcagggca tgttaattat gaatgaaccc
9241 ttttcttta atattaatgt cataattgta tttgtggacc tgtgtaggag aaaaagaccc
9301 tatgttcctc ccattacct tggattgct gtgagaagt gttaactact cataatctca
9361 gctcttggac aattaatagc attaataaca attatcaagg gcactgatca ttagataaga
9421 ctcctgcttc ctcgttgctt acatcggggg tactgaccca ctaaggccc tgtactgtt
9481 aatgtgaata ttgcaatta tatgtctc ctttctggtag agtgggatat tatgccctag
9541 tatccctttt gcattactgc aggggctgct gactactcaa aacttctcct gggactgtta
9601 ataggcacaa tggcagttat caatggtttt ctccctcct gacctttgtta agcaagcgcc
9661 ccacccacc cttagtttcc catggcataa taaagtataa gcattggagt attccatgca
9721 cttgtctatc aaacagtggt ccatactccc aacccttttg cattgcgcca gtgtgtaaaa
9781 tcacaggtag ccatggtgtc atgcttata tacgaagtct tccctctctc tgccccttgt
9841 gtgcccttgg cccctttta cagactattg ctcacaatct caggtgtcca tatttgcaga
```

FIG. 7C

```
 9901 tattaggtaa gattgtgctg tctccctctt ccctteccte tgccctgccc cttttgcctc
 9961 tttgctgggt aatgttgacc agacaaggcc ctttctcttg gacttaaaca attctcagtt
10021 gcactttcct tggtcccacc cattatacat gaaccectct acttcctttc gcattgcttc
10081 tgagtatgct gactacccaa agcccttct gtgttattaa taaacacagt actgattgtc
10141 ccattttca gcccatcagt ccaagatctc cctaccactt tggtgtgttg gtgcagtgtt
10201 gactatgaaa agcaggctg aactaggtgg ataagcctc actcatttc tttcatttat
10261 taatgatcct agtttcaatt attgtcagat tctggggaca agaaccattc ttgcccacct
10321 gtgttactgc tttactgtgc aaaatactga aggcaagtca gacccaggga gctggattgc
10381 catcctttat tttgtgtttc cagtgtacac tataaaattg tctccccagg aaggaaggtt
10441 ggcactttct ctgcattctt ctttccagag cagattgcct ggttaagaat ctcttgttgt
10501 cccctttgta tattgttatt gtaaagtgcc aaatgccagg atacagccag aaaaattgct
10561 tattattatt aaaaaaattt ttttaagaaa gacatctgga ttgtagggtg gactcgataa
10621 cctggtcatt attttttga agccaaaata tccatttata ctatgtacct ggtgaccagt
10681 gtctctcatt ttaactgagg gtggtgggtc tgtggataga acactgactc ttgctatttt
10741 aatatcaaag atattctaga gtggaactct taagaccagt atctttgtgt gggctttacc
10801 agcattcact tttagaaaaa ctacctaaat tttataatcc tttaatttct tcatctggag
10861 cacctgcccc tacttattc aagaagattg cagtaaaacg attaaatgag ggaacatatg
10921 cagaggtgct tttaaaaagc atatgccacc tttttatta attattatat aaaatgaagc
10981 attaattat agtaataatt tgaagtagtt tgaagtacca cactgaggtg aggacttaaa
11041 aatgataaga cgagttccct attttataag aaaaataagc caaaattaaa tattcttttg
11101 gatataaatt tcaacagtga gatagctgcc tagtggaaat gaataatatc ccagccacta
11161 gtgtacaggg tgtttgtgg cacaggatta tgtaatatgg aactgctcaa gcaaataact
11221 agtcatcaca acagcagttc tttgtaataa ctgaaaaaga atattgtttc tggagaagg
11281 atgtcaaaag atcggcccag ctcagggagc agtttgccct actagctcct cggacagctg
11341 taaagaagag tctctggctc tttagaatac tgtaagtact acttcgtagc tattaagtaa
11401 tcttttttct attctatttt ctttctctta gatgccacct atagaaaagt cagagggtcc
11461 agtaagtttc tttccttctt cccacctcat ctgcaatata tatatataga gagagaaata
11521 gatacataca tacatgcata aatacacata tgtgagttaa ccagcagaac tgtagaatta
11581 atattgtgga cccagatcta tgctaggtta cactgataac ctgggtagga atgatatcat
11641 cctatataat ttcattcctg agatgatttt atcgttgagg agctaatgtg agcacatttg
11701 aaataacttt agaaaataat aagtgctgtt ttgtgtgaat cataagtagt agttttagga
11761 agggaaccca caaggatttg aagttgatag aataaactta aggaagtggg ttgcttttt
11821 ctctttaagc caagatagga ttaatattgc agccatctgg atagtccagt tggttttattt
11881 taattcatt tgtttttac ctcttttgga gccatggaaa gagatgaaag ggatagagca
11941 tagccattgt gtttggctat ttgcgaaggt tggcaaatta gtgattgcta aatctcataa
12001 gcttgagtat tttaaagttc agagattgag ggcataaatc taatacttcg gctccttcca
12061 caattttact acatttctgc ccaagaacag atgaccatgg ataatgcata tgtagatac
12121 tttttaagtt tggaaccttt ttgccaagag ggtagtggag aagtgaagtc aaaaccttga
12181 ccttccttgc ctactttatg ctgtagttta tataccttct ttcctcccac ctttcgtaaa
12241 gctaaagaa gcttagcctc cttaatgttt tccagctgac aaaatattgt ttaacataac
12301 attcgaaact ttttttctgg tgcacattca tgcatcacag caggagcaac aagaaccata
12361 taagtgaact ggcttcactt atagcccgtt ttaattcata tccatatttc ctcaggcttt
12421 gtttccatgc ctcccagccc cactccatat gcttaacaac attgtctggc tgactgaggg
12481 ttatatacat catggtcttg aaccttcttg gaaacatggt ctgtgccatt gtttctcaaa
12541 cccagtaat gcttcatgat gaaacacctt ctaaaggaac aaaatttct gagatcctaa
12601 aaaaatgtgt tttgaggaac actgacttaa caaagatatt tgaaatgtaa atatgtttc
12661 caattcacg ttgtctttgt caaagatgtg ttttatataa cttatgtaga acttggggat
12721 ccattagaat atattcacaa atcccaggg ttatcacccc aatttgagaa accctggtct
12781 atgcttatga aatcttctat tggtaattaa attgtcattc attgtcaaca tacaattata
12841 attattattg gaatttgttt taatgaatg aatttggagg tgattctgta ccttaagtca
12901 agaggaagga tggcttgatt ttaggtggat tgattatact agatagcatc caaagtgaa
12961 tcttgaagct gtatttaaat tcattgcttg aaataatttc cacccttaag aaaaatctct
13021 agcattgta aaaagggatg ctctgaaat gtgggcatct tcaaaataga gataattctt
13081 gtgttagttc aacaaatatt attgtaccag gtgctggaat aaatagcaaa accaaagaca
13141 ggatttatat caaggaattt gctttcttat ggaggatgca gaaggaaatc attatggttt
```

FIG. 7D

```
13201 tgggcagaaa tgcttagact ttagtcctgg ctctgagttt ggttcagatc accatcaatc
13261 tgaccatctc gagactgcta gtgaataaag atagggctt atatcaaata cctaaatccc
13321 tgaaaatgac attttgtgat ttggaaaatt ttcaaaagtc taatgaagga aactttttg
13381 gcatttcttt aaatgattat tgtcatttct tttctgactt ttcccttat aaaaccttaa
13441 catgtaggat tggaggaagt tttctgacca ttttctcata tcctcttca gtttatctt
13501 tctgtaactt ccattctct agccacctcc ctaaattaca gagactgtg agaccaggg
13561 ctgctgtgat taggcattca taatttcttt tcagggtgtt tgtgcctga ttatcaaatg
13621 tacagcttga agggagttca tgtcttaaag taatgaatta agagttgacc tttgtgact
13681 gctaaaatat tcttatatgt gaaagcatcc tggaaaaata cgttaccagc ttaaagagaa
13741 agaaactaat gattatatct gaactgagct aatgctctt ctcttcccc aaaccttatc
13801 agtttggatg gcaaagagta atgatgtgtc agttaaacag agctaatgcc ttcctctgcc
13861 ttgtcttaaa gactggattg ggagaaaatt gatattctca ctaccatatt tgggctgta
13921 ggcaagtagc attttacaca ggtttccttc aaaaatccaa ctcaagttgg agctcatgta
13981 ttaagcat agctggctg ctgaatttaa caagttaaac ttcagtggcc atgtacagtt
14041 atatatcact atatatatgt gtattaggct gtcgagttgg tcatgttttt gttggtgact
14101 taggctttac ttgatagctc ttccttgacc tttccaaatt gagtactgat acatggagct
14161 tgggcttctt ctgcatctta tacaaatgag tttggtaaag aagcctctcc tttactgttt
14221 tgatgtttat attagaaata actttgatt attttttttc atgttaggat gagaaactga
14281 aacaaaatgt aaattgacc ggtgctagac ttcttaaatt atgggtagac ttaaagtatt
14341 attttcctta accaattaga atgctagtct tctagtgttc ccggaaacat gagaggttat
14401 gcagtagacc caagcaatac cctcttatta catantcaag tgcgtataag aatttaaaaa
14461 tagggatatg actggaacat cactgtactt taccaggtcc cattataaaa ttatctatgt
14521 tactttaccc atagctttga aaactagtgg catagtatat tttatagtat gctgttagtg
14581 tgatttggcat tgaacagtga tgggatataa tcactctaca atctatatgt tattaaagtt
14641 ttccagcctt atagatctcc cttgactgaa aattagctac taacttacga cttatttttt
14701 acagcagatt gactaggtct ttccaggaaa tctgttgatg tacaaaaaca aagttaatt
14761 gctaatgttt ttttaaaaaa taacttttg atattacgga tacctggtta tttgggcctt
14821 gtatatttta acatcaaaat tacctattat aaatccatat aaacagaaaa gaaagagagt
14881 aagtctttag atcagatctg caaacaatga tggtacgtac tgtagaaaaa tctggaacat
14941 agacttacca gttcttaggt tccattttgc ttgcttttta aaaactgtgt cttataagtc
15001 ttcagcaact ggttgggaga ttttagaaa aaataacctt ttaatgttag aacagtgtag
15061 agatttacag aatgattctg aagatagagt ttctgtgtac ttcacaccca gtttttccca
15121 gtgttaacat tttacattag tttggtacat tgtcaaaac aaaccaatat tgatacatta
15181 ttattaacta gagtccatat tttattcaga tttccttagt ttttccttaa tgttctttt
15241 gtgttccagg atcccattga agataccacg ctgcatgtgt cctagtagt catgtctcct
15301 taggctctc ttggtaatga cagttctca gactctttgt tttgatgaa cttcacagtt
15361 ttgaggacta atggtccagt attctataga atgtctctct attggaattt gtctgatgtt
15421 cttctcatga ctagattggg tttatgagtg tttaggagga agaccacaaa ggtagagtgc
15481 cattcttatc acttatcaag agtacatact atcaacatga cttatcactg tttatgttat
15541 cattaatcac ctgtctgagg tacatttgt caggtttctc cagggtaaaa ttagtcttta
15601 tttctccatt tcctactat actgttcaca taggaagtca ctatgtcag ccagcactta
15661 aggaatggga aattaccttc cacctcattg agggcagagt attacataa attatttgga
15721 attcttttgc acaggatgtc ttttctccac aatgtattgt gtttattcag tcatttatat
15781 cagtatgatc tcaggatat tttatactct gggttataat acagtattac tttattctgt
15841 tgttcaaatt gttccagctt tggccattgg gagtgtttc atttggcttt gatataccc
15901 catgaatgtg ggttttttgt ttgagcactt tcttattttt ggaactacaa catgcttcag
15961 actcatttgc atatctctg cctggaccta aaatgatgta tttctgcaag gagccttgat
16021 acttttatt ggagagtaat attagaaatc aagaagtgaa tgctaggtgc gctcattact
16081 actggagtgt cattccttca agacctttc agttgacaag agcaaggaga tatatatttg
16141 cattctaacg tgtgtatatg cacatagcta taaatatata taaccatctg tatctatatt
16201 aaactaaatg tgtttatacc tacgtctcca actctaatca ttgccacatg gatcattata
16261 gtctcaacctc cttgcttatc tgttaacttcc cattcctaca gtgagaaacc tggcttggtt
16321 gggaaatttt tctgttaata ttacggtagt gagtgtttga catttgcttc tatggttaag
16381 tttagggaga gttagctgt agggtattct tgaaactaga aatgaccctt ctgccctaaa
16441 tgtttctgcc agttttgaaa cgtaaaatag gttgcagaaa caaactttat cttaagaacc
```

FIG. 7E

```
16501 agatttact tcaatcaca tttgacatt gattttcaga ttaaattatt ctgatatcgc
16561 caggtaagct gttccttggg tatgcattc ttcttccgt ttttttctaa gagctaagg
16621 accctgagaa cactggaggt gggaaaggaa gggaaaggca tgttcacacg tggatagga
16681 aaggtcatt tactgaccc cagctagcct tcaaagtgc ctatttaaga cccaaggagt
16741 agatgtcttc cttggcaatt gtaacccaa tataattttt aacctttcaa tttagtcaa
16801 gaaagttggt gtgctgttac aaaagtgcc ctgattaaca gcattgtcat gtgcattgca
16861 tattaatcag caattaaaa taacatgaaa ttatgttgag tataattta atatttata
16921 ttagatatta gttgagaca gtgttctca agtctgtata ataagtttga tagtagggag
16981 gttttctctc aagaaaagaa ttattcagtg tgcactaca taatcactgc ttagattca
17041 caattaatat ttgctatat ttgatttaac gttttctgta aaagaaaaat attattatgt
17101 actattagg tttatggaa taattgttaa gttaaagtgt atgaacaaac ctgaattgaa
17161 atctgtttgc ctacatctat aatcacacta taaacatag cagatgtaca aattagtagt
17221 taatagataa ctaaatgca aatatggcac tactattata gtattatagt ttcttttgag
17281 tggcgtgtct gtaatatcac atgctgtgtt gatgcacttc accaaactgc tgttttcaaa
17341 ctgctttaaa tcctgccatt atagcacata gcaatgctat ttcacttttca tttggacaa
17401 aacacattta tatattgttt gcttctcttc tttctgtaa tcccaaggca acaaactag
17461 aacatttgcc actaatctgg caacgtggtc ctatactatg aagtagtcat atagctgatc
17521 tcaactattc ttacagtgaa atgagagtat tgtgaagtt ttgtagaaag ctcccctat
17581 gtcctgagaa tctatgcaca gacccacag ttaaaagcc tttgaattgt gggaagacat
17641 gggtttaagt atcacttggt taccttctat ttgtgtaaca ttgaggtagt ttcatcttct
17701 gggttccaag ttccttaga gaatgaaaat gttgaattat gttgattttt tttttttg
17761 agacggagtc ttgctcttc gcccaggctg gagtgaagta gcacgatctc gactcactgc
17821 aacctcttc cccatgatc aagcaattct cctgcctcag cctcccaagt agctgggatt
17881 acaggcacc gcccccacc cccgcccc agctaatgtt tgtatttta gtacagatgg
17941 agtttgcg tgttggccag gctggtctcg aacttctgac ctcaggtgat ccactgcct
18001 tggctccca aagtgctagg attacaggca tgagccactg cgctggcct atgtgattat
18061 taatatcacg tctagctgtg acaattctgt ctgatgctgg agtatttgaa ccagatggct
18121 ggctgtgcca ctcagttatt ctctcctaa gacttttgata ttttgttggt ctgcaagatg
18181 acggattctc aaatttcttg tcagtgaata ttgaaccta gtgaaatgta tggttctgta
18241 tcagttccaa aatgtaacca cttttctctag ccttagattc ccagttccaa aatgtaacca
18301 ttttctctag ccttagattc ccgttaaggg aaagggaatg ctcttgagt atgtcatcac
18361 catgaaaacta gccaaaacta gaggcttg atgctaaagc aagtactcc ataaatatgc
18421 ttagtgaagac tggggggac tggaatagtt gttcccttt agatgccagt gtataagtga
18481 attgagcta ggatccgttt attaaatatt tctttaggtg tatttgcttg catatggagt
18541 gcacatttac tctcattaat ggagttttag gaagcagtag agtaaatgca taaacatgta
18601 tgaccgcca tgtttaactg gaagcctgca tttggaagtc aagtatctca tcttagacta
18661 aattaggatg gggaaggatg ttggcaagag acttgaagc tgtctgct tatactgaga
18721 acatcataga acagttggc cttttaaag ctagagaata gtgtgaata agtgatgttc
18781 catatactcc tgtttgacat tgacataaag gttcctcat gatacagtaa tccctgatca
18841 gggatctgga agcctgtatt catttaaggt actcaggttt aacatactgg gtgcttttca
18901 caccatacta tacagtacca tgcaagtgc tttcaagact gcaaatttgg cttagatcc
18961 cttagtgag ctcctatgct atagtaaagg tagatagcca attattaaaa acagtcaaga
19021 caatccaac tctaaagcagt agtagcagtt gccaacaccac ctgaatctt gaagtatttt
19081 cagcaacagg atgaccatta gcacaaatt tagtgtcagc ccttaagtc ggtaattggtt
19141 tgacccatat tctcatgtag tctcttttct tcacttgtct aatcttccg tgtactgca
19201 gggcttgtca ttagaggact ttagggagac caagcaggct agaaagtaga gacaggagat
19261 acctatgtct aatgcttcag tttatactc ctaggtttt tcattgggg tttttgtaac
19321 tcttttggta tcctaccggt gcttggtag cctactgaac cctgtcttc ttcttaagga
19381 cattctgagc atgtgagatc tgaggactgc aaacagctat aagaggctcc aaattaatca
19441 tatcttccc tttgagaatc tgccaagct ccagctaatc tactggatg ggttgccagc
19501 tatctggaga aaaagtagt tggggaatt tattgttgta gtgcttcgt cttggatttg
19561 aacttccac aactctctt tttaaagcag aacacagctg ggcatggtgg ctcctgcttg
19621 taattccagg gctttggag gttgaggtgg gggatcact tgagccagg agttgaagac
19681 ccatgtctct acaataaaat aaaattagtt gggcatggtg gtacgtgcct gtagtcctac
19741 ctactctgga ggctgaggca gcaggattgc ttgagccag gagttcaagg ctgcagtgag
```

FIG. 7F

```
19801  ccatcattag  ccactgcact  ccagcctagg  tggcagagcg  ggacccagtc  tcttaaaaag
19861  aaagaaaagc  agaacgtgag  ccagtttttca  tcaattccta  tactttttct  tttgcatgta
19921  cacatacatt  ttaactttac  ataatgagtt  cggcctgttt  catttatccc  tcagagctgg
19981  gctccagtga  ggtctgtaag  ggcaagcata  cttgatcccc  aatgaagaat  gagagatgca
20041  aagcactaaa  ttattctctt  tctcaccaca  cagcaagata  gattaatga  acttaacacc
20101  tttgattag  tggcttttta  aattattccc  acttttcttt  ggcagatggg  tattaagttc
20161  tcaggatttg  tttacaaata  agactaactt  catctgtatt  agctcagttt  tggtaggcct
20221  aattccatta  tcactgccat  ttccttgttt  taagaatca  aaatttctta  gcttgaaaaa
20281  caattgaaat  tgttaaaaag  tggaatagga  gagcccggg  ggcctgtata  aggaatttac
20341  tgaatccctg  gtttttctgta  ccttgtttt  ccttctgcat  agatttgctt  aactgttttt
20401  gtggcgtgta  tttttttttt  ttgcagttt  cgctcttgtt  gcccaggctg  gagtgcaatg
20461  gcgcaatctc  agctcactgc  aacctctgtc  tcctgggttc  aagtattct  cctgcctcag
20521  cctctcgagt  agctgagatt  acaggcatgc  gcgaccacgc  caggctaatt  ttgtatttt
20581  agtagagacg  gggtttctcc  atgttggtca  ggctggtctc  aaactcctga  cctcaggtga
20641  ttcacccgcc  tcgacctccc  aaactgctgg  gattacaggc  gtgagccacc  acgcctggcc
20701  agctgttgtt  ataactggag  ttctatgtgc  ttgtgaccat  tcttggtttc  tccgaatatc
20761  ctagaacttt  ggtggcgccc  tattatacag  gttgttgaag  aaatgttacc  atgtggattg
20821  agtaggaaac  aattctcttt  atcttggcaa  tattatggca  tggcactact  taaagtacaa
20881  attaaaagag  ggggatgcta  cagaactagc  tgacaggcac  tttgatagag  gtggatttct
20941  cagttcttaa  aatagctctt  tataaaggaa  gccagaggca  ttgtggagga  gaattcttac
21001  ataactcata  gggttagacc  acatccgacc  ttttctgtgt  ggcttcatgg  ctctcttggt
21061  tgagaaagca  ttagtttctc  cttccattag  tttcaacctc  ttgattctt  gacccccta
21121  ctatattttg  tgctgagaac  acaagggtat  taacaaccca  cattgtagag  gatcgctcag
21181  taataaagac  tggagaataa  aatgcagcat  gggaatattg  gcaattactc  agttctaaat
21241  ttctcttgga  aatgaggaa  agcatacaga  atagagctgg  aatgaatagg  ataattttt
21301  tttttttgc  taagttggta  gccagaatat  aacagctccg  cacaactgta  aatgtccact
21361  cttcaatcca  catgaagaaa  agggtaaaaa  tatggttgaa  ctcaaccact  agttgcccat
21421  tagaacagac  tttcccagtg  tactgcattt  caatactttt  tctttatct  ctttcagat
21481  cttcctcaga  agaataggct  tgttgtttta  cagtgttagt  gatccattcc  ctttgacgat
21541  ccctaggtgg  agatgggca  tgaggatcct  ccaggggaaa  agctcactac  cactgggcaa
21601  caacctagg  tcaggaggtt  ctgtcaagat  actttcctgg  tcccagatag  gaagataaag
21661  tctcaaaaac  aaccaccaca  cgtcaaggtg  cgtaagctgt  cctaaaagc  ataataagta
21721  gtcttaattt  tgattttgtt  ttccagtata  cattgcactt  agtgtttcac  tgaggtcgta
21781  ttcatcatta  ttctgcatat  gattggtaa  aaacagcttc  ctaactaacc  tgggaagcaa
21841  ctgggtgtga  gattaactgg  ttaaagtgat  gatgtaaaga  gggtagcggg  ttgcatgtgt
21901  tcgggtgttt  ggagtggac  tatagcacgt  ggcagaggct  tacagctaag  ttgttcttt
21961  aggagaacat  ggacaactgt  cacatcagtg  acattgatca  catgggcaaa  tcattctgtt
22021  ccatgtggtc  cccaaagtct  ctcttaaagc  cttacagaag  aactttgcca  atcatttaca
22081  tacttcagga  tggcttggga  tgccatggtg  tataatacaa  caagtgagag  gtgtgtcttt
22141  ttatgctatg  gttgctgatt  gatggaagcc  gcataaatac  aaatggaaac  ctgactaaaa
22201  atggcacaaa  gttatctgtc  atcaggcagg  agctaaagaa  ccaggaccct  acattctcta
22261  ggtcagtgtt  gggagaggct  gattagcgag  tgagaattgg  cagataaagg  tgaccattcg
22321  gtgcaataaa  tcctgaacgt  ataggcttg  cccagcattc  ttcgtaaata  gtgggtagct
22381  ataaatttca  tgaaatattt  tcatgggtaa  gaacctctga  aatgttataa  ttgactagaa
22441  atctctgtag  atttagaaat  agagagttac  taacaaattg  ttagaaagtc  taggaactag
22501  aaagctaagt  tgagagttat  ctaggaagat  ctatctattg  tactcataat  ctttagataa
22561  attctcctag  ggccagtagt  ctatgtgaat  tttctttttc  ttcttcttct  tcttctttt
22621  ttttgtattt  tagctgcaat  gttaaacaac  ctatgtgaat  tttcttattg  tgagaatatt
22681  tgccttccag  agtgactcac  ctttatctca  aagagcaata  ttgtgagttt  tgaaaatgct
22741  gctctaaggc  tgtgttttgt  tagtcctgag  ccaggagact  taaagcaaac  ttgagggtc
22801  ttaaacatc  gaagtgagcc  ttaaacattg  ggaagacctt  atgtttttcc  ctctcatatc
22861  tattatttt  gtgatctcag  ttattaatca  tttaaaggga  ctcttttccta  gctgattggc
22921  acttaaaaca  ggatggaagt  cttttttttt  tttttttttt  ttgagatgga  gttttgctct
22981  tgttgcccag  gctggagtgc  aatggtgcaa  tctcagctca  ctgcaacctc  tgcatcccgg
23041  gttcaagcga  ttctcctgcc  tcagcctccc  aagtagctgg  gattacagtc  atgcaccacc
```

FIG. 7G

```
23101 aagcccggct aattttgtat tttaatagaa gacggtgttt ctccatgttg gtcaggctgg
23161 tctcaaactc ctgacctcag gtgatccgcc cacctcaacc tccaaagttg ctgggattat
23221 gggcgtgagc cactgcgccc ggcagttctg gtcttaact aaggtataag gctatgactg
23281 gtagtggtgt ctctagtgac tcatcaagtg atatttggca agacattttc ccatttatgc
23341 cagttcccta ttctgttgaa tgaggaaatt ttctctctaa agacctaaaa gttttgactt
23401 tataggtttc aaagttctgt ggaaacattt tctattgctt attaatttga atcttatgta
23461 actctagcac agtactcaat atttatggca tttacatggt ttatctcatg tttttttata
23521 gctcttcatt gttcctatct gccaaatcat tatacttcct acaagcagtg cagagagctg
23581 agtcttcagc aggtccaaga aatttgaaca cactgaagga agtcagcctt cccacctgaa
23641 gatcaacatg cctgcaactc tagcacttga ggatagctga atgaagtaag ttgttgatgt
23701 tgcagtcctg tgaggatcac ttcagaactg ttatacagc tgtttttttgg gagctggtgt
23761 tggatgggt gtgttgatct aatgtgaagt gggctaaat gtgagatgga aagatgacca
23821 gtcttccata ttactgactg ggttcactga agcaactcaa agacattatg gtcttcttac
23881 cagttgtatc acagaagaat ttagccttg ctgtgtgtt ctatgtcttc actgtatagg
23941 cctctgtca ttcttagagc cttaaacgtt gagaagctta aacaccatt tctgctttct
24001 gctgaaaggg taacccttc tcatctcgt ttgtgagaga ctctgtcgtc agttaagatt
24061 agtgtaaaaa gaaaactaaa ctctgaagta gccattataa agtgtgaga atgaagtcag
24121 tttctaaag agttggggaa aggtgatgct aaggagggg attgagcaag tcctatcaaa
24181 gagcttttc tgaaataact tagtcatctg tgacatccca tttggtcttt ccagaaatcc
24241 tagtaaatag ttgtaacagg atgttaagag gcatacattg tgtgttttaa atcctctgct
24301 actcattagg tatatgacct ttgacaactt aaagtctcta gactttctg ttgtgaggg
24361 ttaaatgaaa tcatgtatgt aaagtgctca cctattgcag tgcctggcac atgtcaagta
24421 aaggtaacc caagaagact catcagttca ttttcaacaa tataagtgac cactagcact
24481 atcaggtagc aggcagagtt ggcatgcttt ggttctatgt aagaaatccc taagtaaaa
24541 gtttataaat agagagcat ctgtgttggt attggtggtt gttattattg tagtactata
24601 agtagtatcc gtagtaacaa tagtttatta taattactaa tgacactttt tgattttttt
24661 tatctttctg tgatgctttt cctgcctctt gtgccctca ctgtatcttg cctcttctac
24721 tacttactc ctctgaatgt ctgccttgc ttatctcttg cactcaagtg tgtatttctc
24781 tgtctcttc tttcttgtct ttgctctttg ttctctatct aaagtgtgtc ttacccattt
24841 ccagttct cttgctaatt tcttttcgtgt gtgccttgc ctcattttct cttttgttc
24901 acaagagtgg tctgtgtctt gtcttagaca tatctctat tttcatttt gttgctattt
24961 ctcttgctc tcctcgatgt ggctctctt tcacgcttta tttcatgtct tctttttggg
25021 tcactgctg tgtgctttt gtctttct tgtttctgtct tcctctcctt tctctgccta
25081 cctctcttt ctcttgtgaa actgtgatta tttgttaccc cttccccttc tcgttcgttt
25141 taaatttcac cttttttctg agtctggcct cctttctgct gtttctactt ttatctcac
25201 atttctcatt tctgcattcc cttctgcct ctcttgggct attctctctc tcctcccctg
25261 cgtgcctcag catctcttgc tgtttgtgat tttctatttc agtattaatc tctgttggct
25321 tgtatttgtt ctctgcttct tccctttcta ctcacctttg agtatttcag cctcttcatg
25381 aatctatctc cctctctttg atttcatgta atctctcctt aaatatttcc ttgcatatgt
25441 gggcaagtgt acgtgtgtgt gtgtcatgtg tggcagaggg gcttcctaac ccctgcctga
25501 taggtgcaga acgtggctga tcagacaag cattgtggag cggttcctta tgccaggctg
25561 ccatgtgaga tgatccaaga ccaaacaag gcctagact gagtaaaac ccagaactca
25621 agtagggcag aagtgtgaag gctcatatgg atagaagcc caagtataa gacagatggt
25681 ttgagacttg agaccgagg actaagatgg aagccatg ttccaagata gatagaagcc
25741 tcaggcctga aaccatcaaa agcctcaaga gccagaaaa cagaggtgg cctgaattgg
25801 acccgaaggcc tgagttggat ggaagtctca aggcttgagt taaagtctt aagcctggg
25861 acaggacaca tggaaggctt aagaactgag acttgtgaca caaggccaac gacctaagat
25921 tagccaggg ttgtagctgg aagacctaca acccaaggat ggaaggccc tgtcacaaag
25981 cctacctaga tggatagagg acccaagcga aaaggtatc tcagactaa cggccggat
26041 ctggaggccc atgaccaga acccaggaag gatagaagct tgaaccctg gggaaatccc
26101 aagatgaaa ccctaaacc tacctctttc ctattgttta cacttcttac tcttagatat
26161 ttccagtcct cctgttatc tttaagcctg atctttatga gatgtacttt tgatgtgc
26221 cggttacctt tagattgaca gtattatgcc tgggccagtc ttgagccagc tttaaatcac
26281 agcttttacc tattttgtag gctatagtgt tttgtaaact tctgtttcta ttcacatctt
26341 ctccacttga gagagacacc aaaatccagt cagtatctaa tctggcttt gttaacttcc
```

FIG. 7H

```
26401 ctcaggagca gacattcata taggtgatac tgtatttcag tcctttcttt tgacoccaga
26461 agcootagac tgaaagata aaatggtcag gttgttgggg aaaaaaagt gocaggctct
26521 ctagagaaaa atgtgaagag atgctccagg ccaatgagaa gaattagaca agaaatacac
26581 agatgtgcca gacttctgag aagcacctgc cagcaacagc ttccttcttt gagcttaggt
26641 gagcaggatt ctgggttttg ggatttctag tgatggttat ggaaagggtg actgtgcctg
26701 ggacaaagcg aggtccaag gggacagcct gaactcctg ctcatgtag tgccaaata
26761 atttggtgga ctgtgccaac gctactcctg ggttaatac ccatctctag gcttaagat
26821 gagagaacct gggactgttg agcatgttta atactttcct tgattttttt cttcctgttt
26881 atgtgggaag ttgatttaaa tgactgataa tgtgtatgaa agcactgtaa aacataagag
26941 aaaaaccaat tagtgtattg gcaatcatgc agttaacatt tgaaagtgca gtgtaaattg
27001 tgaagcatta tgtaaatcag gggtccacag ttttctgta agggtcaaa tcataaatac
27061 tttagactgt gggccatatg gtttctgtta catattgtt tttaaacaa cgttttata
27121 aggtcaaaat cattcttagt tttgagcca attggattg gctgctgtt catagcttac
27181 caccccctga tgtattattt gttattcaga gaaaattct gaatactact agtttcctt
27241 tctgtgcctg tccctgtgct aggcactaaa aatgcaatga ttattgatat ctaggtgacc
27301 tgaaaaaaaa tagtgaatgt gctttgtaaa ctgaaagca cttgtattct actgtgataa
27361 gcgttgtgga tacaaagaaa ggagcaagca taaaaagtg ctcttcaaa aggatatagt
27421 actatgcaga cacaaggaat tgtttgataa atgaataaat tatatgtata tttgaggcca
27481 atttgtgttt gctgctctgg taattttgag taaaaatgca gtattccagg tatcagaaac
27541 gaaaacacat ggaaactgct tttaaacttt aaatatact gaaacataa gggactaagc
27601 ttgttgtgt cacctataat gtgccagata ccatgctggg tgctagagct accaaagggg
27661 gaaagtatt ctcatagaaa aaaaatttc agaaagtgc atattaaagt gctttgtaaa
27721 ctaaagcatg atacaaatgt caatgggcta catatttatg aatgaatgaa tggatgaatg
27781 aatattaagt gcctcttaca taccagctat tttgggtact gtaaatacaa agattaattc
27841 tcctatgtaa taagaggaaa gtttatcctc tatactattc agatgtaagg aatgatatat
27901 tgcttaattt taaacaatca agctttact ggtgaggtta agttaaatta ttactgatac
27961 attttccag gtaaccagga aagagctagt atgaggaaat gaagtaatag atgtgagatc
28021 cagaccgaaa gtcacttaat tcagcttgcg aatgtgcttt ctaaattata aagcacttgt
28081 aaatgaaaaa ttgatgctt tctgtatgaa taaactttc tgtaagctag gtattgtctc
28141 tacaaaattc tcattgtata gttaaaccac agtgagaagg gttctataag tagttataca
28201 aaccaagggt ttaaatacct gttaaataga tcaatttga ttgcctacta tgtgaactca
28261 ctgttaaagg cactgaaaat ttatcatatt tcatttagcc acagccaaaa ataaggcaat
28321 acctatgtta gcatttgtg aactctaagg caccatataa atgtaactgt tgatttctc
28381 acttggtgct gggtactagg tttataaaaat tgtatgatag ttattatatt gtgcaaataa
28441 agtaggaaaa tttgaataac aatgattatc tttgaatac gcatacgcaa gggattggtt
28501 gtctgaagaa tgccactata gtagttatct attgtgtgcc aatctcattg ctaggcattg
28561 gggatgcaaa gataaaccat ctttattgtg tcttgggtag cagaagaaaa tatgtgtaaa
28621 atcaatttat aatttgtaaa ctgccaccca tatataagct atatctgctg aatgatcctt
28681 gattactctt atcctagag ataacaactg gggcacaaa cattattat cattattgaa
28741 cctacaacag agatctatgt gtagatttac aaagcctaca gttctataca gataggaatg
28801 aactactggc ttactgaatg gtgattactt tctgtggggc tcggaactac atgcctagg
28861 atataaaaat gatgttatca ttatagagtg ctcacagaag gaaatgaagt aatataggtg
28921 tgagatccag accaaaagtc atttaacaag tttattcagt gatgaaaaca tgggacaaat
28981 ggactaatat aaggcagtgt actaagctga gtagagagat aaagtcctgt ccagaagata
29041 catgcttcct ggcctgattg aggagatgga aaatttttgc aaaaaacaag gtgttgtggt
29101 cttccatcca gttcttaag tgctgatgat aaaagtgaat tagacccacc ttgactggc
29161 ctacagaagt aaaggagtaa aaataaatgc ctcaggcgtg cttcttgatc cattgataa
29221 acaagcatc tttatgtgg aatataccat tctgggtcct gaggataaga gagatgaggg
29281 cattagatca ctgcagctg aagatagaag aacatctttg gtttgattgt ttaaataata
29341 tttcaatgcc tattctctgc aaggtactat gttcgtaaa ttaaataggt ctggccaga
29401 agaccactc aatgccttt gagattaaaa aaaaaaaaa aagaaagaa aaatgcaagt
29461 ttcttcaaa ataagagac attttccta gttcaggaa tcccccaaat cactcctca
29521 ttggcttagt ttaaagccag gagactgata aaaggctca gggtttgttc tttaattcat
29581 taactaaaca ttctgcttt attacagtta aatggttcaa gatgtaacaa ctagttttaa
29641 aggtatttgc tcattggtct ggcttagaga caggaagaca tatgagcaat aaaaaaaaga
```

FIG. 7I

```
29701 ttcttttgca tttaccaatt tagtaaaaat ttattaaaac tgaataaagt gctgttctta
29761 agtgcttgaa agacgtaaac caaagtgcac tttatctcat ttatcttatg gtggaaacac
29821 aggaacaaat tctctaagag actgtgtttc tttagttgag aagaaacttc attgagtagc
29881 tgtgatatgt tcgatactaa ggaaaaacta aacagatcac ctttgacatg cgttgtagag
29941 tgggaataag agagggcttt ttattttttc gttcatacga gtattgatga agatgatact
30001 aaatgctaaa tgaaatatat ctgctccaaa aggcatttat tctgacttgg agatgcaaca
30061 aaaacacaaa aatggaatga agtgatactc ttcatcaaac agaagtgact gttatctcaa
30121 ccattttgtt aaatcctaaa cagaaaacaa aaaaaatcat gacgaaaaga cacttgctta
30181 ttaattggct tggaaagtag aatataggag aaaggttact gtttattttt tttcatgtat
30241 tcattcattc tacaaatata ttcgggtgcc aataggtact tggtataagg ttttggccc
30301 cagagacatg gaaaaaaat gcatgccttc ccagagaatg cctaatactt tcctttggc
30361 ttgttttctt gttagggca tggcttagtc cctaaataac attgtgtggt ttaattccta
30421 ctccgtatct cttctaccac tctggccact acgataagca ggtagctggg ttttgtagtg
30481 agcttgctcc ttaagttaca ggaactctcc ttataatga cacttcattt tcctagtcca
30541 tccctcatga aaaatgactg accactgctg ggcagcagga gggatgatga ccaactaatt
30601 cccaaacccc agtctcattg gtaccagcct tggggaacca cctacacttg agccacaatt
30661 ggtttgaag tgcattaca aggttgtct attttcagtt ctttactttt tacatgctga
30721 cacatacata cactgcctaa atagatctct ttcagaaaca atcctcagat aacgcatagc
30781 aaaatggaga tggagacatg atttctcatg caacagcttc tctaattata ccttagaaat
30841 gttctccttt ttatcatcaa atctgctcaa gaagggcttt ttatagtaga ataatatcag
30901 tggatgaaaa cagcttaaca ttttaccatg cttaagtttt aagaataaaa taaaaattgg
30961 aaataattgg ccaaaattga aaggaaaaat tttttaaaa tttctctaaa tgtaggcctg
31021 gctggctttt gacctttcc gttttaaat cactcacaga gggtgggaca ggaggaagag
31081 tgaaggaaaa ggtcaaacct gttttaaggg caacctgcct ttgttctgaa ttggtcttaa
31141 gaacattacc agctccaggt ttaaattgtt cagtttcatg cagttccaat agctgatcat
31201 tgttgagatg aggacaaaat cctttgtcct cactagtttg ctttacattt ttgaaaagta
31261 ttattttgt ccaagtgctt atcaactaaa ccttgtgtta ggtaagaatg gaatttatta
31321 agtgaatcag tgtgaccctt ctgtcataa gattatctta aagctgaagc caaaatatgc
31381 ttcaaaagaa gaggacttta ttgttcattg tagttcatac attcaaagca tctgaactgt
31441 agtttctata gcaagccaat tacatccata agtggagaag gaaatagata aatgtcaaag
31501 tatgattggt ggaggagca aggttgaaga taatctgggg ttgaaatttt ctagttttca
31561 ttctgtacat ttttagttag acatcagatt tgaaatatta atgtttacct ttcaatgtgt
31621 ggtatcagct ggactcagta acacccttt cttcagctgg ggatggggaa tggattattg
31681 gaaaatggaa agaagaaagt aactaaaagc cttccttttca cagtttctgg catcactacc
31741 actactgatt aaacaagaat aagagaacat tttatcatca tctgctttat tcacataaat
31801 gaagttgtga tgaataaatc tgcttttatg cagacacaag gaattaagtg gttcgtcat
31861 tgtccttcta cctcaaagat aatttattcc aaaagctaag ataaatggaa gactcttgaa
31921 cctgtgaact gatgtgaaat gcagaatctc ttttgagtct ttgctgtttg gaagattgaa
31981 aaatattgtt cagcatgggt gaccaccaga aagtaatctt aagccatcta gatgtcacaa
32041 ttgaaacaaa ctggggagtt ggttgctatt gtaaaataaa atatactgtt ttga
       (SEQ ID NO:2)
```

FIG. 7J

SEQUENCE LISTING

<160> NUMBER OF SEQ ID NOS: 2

<210> SEQ ID NO 1
<211> LENGTH: 16481
<212> TYPE: DNA
<213> ORGANISM: Homo sapiens

<400> SEQUENCE: 1

```
ccttcagttc ttaaagcgct gcaattcgct gctgcagcca tatttcttac tctctcgggg      60
ctggaagctt cctgactgaa gatctctctg cacttggggt tctttctaga acatttcta     120 gtcccccaac acccttatg gcgtatttct ttaaaaaaat cacctaaatt ccataaaata     180 ttttttaaa ttctatactt tctcctagtg tcttcttgac acgtcctcca tattttttta     240
aagaaagtat ttggaatatt ttgaggcaat ttttaatatt taaggaattt ttctttggaa     300
```

```
tcattttttgg tgacatctct gttttttgtg gatcagtttt ttactcttcc actctctttt       360
ctatattttg cccatcgggg ctgcggatac ctggttttat tattttttct ttgcccaacg       420
gggccgtgga tacctgcctt ttaattcttt tttattcgcc catcggggcc gcggatacct       480
gcttttattt tttttttcct tagcccatcg gggtatcgga tacctgctga ttcccttccc       540
ctctgaaccc ccaacactct ggcccatcgg ggtgacggat atctgctttt taaaaatttt       600 cttttttttgg cccatcgggg cttcggatac ctgcttttt tttttttatt ttccttgccc       660
atcggggcct cggatacctg ctttaatttt tgttttttctg cccatcgggg ccgcggatac       720
ctgctttgat tttttttttt catcgcccat cggtgctttt tatggatgaa aaatgttgg        780 ttttgtgggt tgttgcactc tctggaatat ctacactttt ttttgctgct gatcatttgg       840
tggtgtgtga gtgtacctac cgctttggca gagaatgact ctgcagttaa gctaagggcg       900
tgttcagatt gtggaggaaa agtggccgcc attttagact tgccgcataa ctcggcttag       960
ggctagtcgt ttgtgctaag ttaaactagg aggcaagat ggatgatagc aggtcaggca      1020
gaggaagtca tgtgcattgc atgagctaaa cctatctgaa tgaattgatt tggggcttgt      1080
taggagcttt gcgtgattgt tgtatcggga ggcagtaaga atcatctttt atcagtacaa      1140
gggactagtt aaaaatggaa ggttaggaaa gactaaggtg cagggcttaa aatggcgatt      1200
ttgacattgc ggcattgctc agcatggcgg gctgtgcttt gttaggttgt ccaaaatggc      1260
ggatccagtt ctgtcgcagt gttcaagtgg cgggaaggcc acatcatgat gggcgaggct      1320
ttgttaagtg gttagcatgg tggtggacat gtgcggtcac acaggaaaag atggcggctg      1380
aaggtcttgc cgcagtgtaa acatggcgg gcctctttgt ctttgctgtg tgcttttcgt       1440
gttgggtttt gccgcaggga caatatggca ggcgttgtca tatgtatatc atggcttttg      1500
tcacgtggac atcatggcgg gcttgccgca ttgttaaaga tggcgggttt tgccgcctag      1560
tgccacgcag agcgggagaa aaggtgggat ggacagtgct ggattgctgc ataacccaac      1620
caattagaaa tgggggtgga attgatcaca gccaattaga gcagaagatg gaattagact      1680
gatgacacac tgtccagcta ctcagcgaag acctgggtga attagcatgg cacttcgcag      1740
ctgtctttag ccagtcagga gaaagaagtg gaggggccac gtgtatgtct cccagtgggc      1800
ggtacaccag gtgttttcaa ggtcttttca aggacattta gcctttccac ctctgtcccc      1860
tcttatttgt cccctcctgt ccagtgctgc ctcttgcagt gctggatatc tggctgtgtg      1920
gtctgaacct ccctccattc ctctgtattg gtgcctcacc taaggctaag tatacctccc      1980
cccccacccc caacccccc caactcccca ccccacccc ccaccccca cctcccacc         2040 cccctacccc cctacccccc tacccccctc tggtctgccc tgcactgcac tgttgccatg      2100
ggcagtgctc caggcctgct tggtgtggac atggtggtga gccgtggcaa ggaccagaat      2160
ggatcacaga tgatcgttgg ccaacaggtg gcagaagagg aattcctgcc ttcctcaaga      2220
ggaacaccta ccccttggct aatgctgggg tcggattttg atttatattt atcttttgga      2280
tgtcagtcat acagtctgat tttgtggttt gctagtgttt gaatttaagt cttaagtgac      2340
tattatagaa atgtattaag aggctttatt tgtagaattc actttaatta catttaatga      2400 gttttttgttt tgagttcctt aaaattcctt aaagttttta gcttctcatt acaaattcct      2460 taacctttt ttggcagtag atagtcaaag tcaaatcatt tctaatgttt taaaaatgtg       2520
ctggtcattt tctttgaaat tgacttaact attttccttt gaagagtctg tagcacagaa      2580
acagtaaaaa atttaacttc atgacctaat gtaaaaagaa gtgtttgaag gtttacacag      2640
gtccaggcct tgctttgttc ccatccttga tgctgcacta attgactaat cacctactta      2700
```

```
tcagacagga aacttgaatt gctgtggtct ggtgtcctct attcagactt attatattgg      2760
agtatttcaa ttttttcgttg tatcctgcct gccagcatc cagttcctcc ccagccctgc      2820
tcccagcaaa ccctagtct agccccagcc ctactcccac ccggcccag ccctgcccca       2880 ggcccagtcc cctaacccc cagccctagg cccagtccca gtcctagttc ctcagtctgt        2940
ccagcttctc tcgaaagtca ctctaatttt cattgattca gtgctcaaaa taagttgtcc      3000
attggtatcc tattatactg ggatattccg tttacccttg gcattgctga tcttcagtac      3060
tgactccttg accatttttca gttaagcata caatcccatt tgtctgtgat ctcaggacaa     3120
agaatttcct tactcggtac gttgaagtta gggaatgtca attgagagct ttctatcaga     3180
gcattattgc ccacaatttg agttacttat cattttctcg atccctgcc cttaaaggag       3240 aaaccatttc tctgtcattg cttctgtagt cacagtccca attttgagta gtgatctttt      3300
cttgtgtact gtgttggcca cctaaaactc tttgcattga gtaaaattct aattgccaat     3360
aatcctaccc attggattag acagcactct gaacccatt tgcattcagc agggggtcgc      3420
agacaacccg tcttttgttg gacagttaaa atgctcagtc ccaattgtca tagctttgcc      3480
tattaaacaa aggcaccta ctgcgctttt tgctgtgctt ctggagaatc ctgctgttct      3540
tggacaatta agaacaaag tagtaattgc taattgtctc acccattaat catgaagact      3600
accagtcgcc cttgcatttg ccttgaggca gcgctgacta cctgagattt aagagtttct     3660
taaattattg agtaaaatcc caattatcca tagttctgtt agttacacta tggcctttgc     3720
aaacatcttt gcataacagc agtgggactg actcattctt agagccccctt cccttggaat   3780 attaatggat acaatagtaa ttattcatgg ttctgcgtaa cagagaagac ccacttatgt    3840
gtatgccttt atcattgctc ctagatagtg tgaactacct accaccttgc attaatatgt     3900
aaaacactaa ttgcccatag tcccactcat tagtctagga tgtcctcttt gccattgctg   3960
ctgagttctg actacccaag tttccttctc ttaaacagtt gatatgcata attgcatata     4020
ttcatggttc tgtgcaataa aaatggattc tcacccatc ccaccttctg tgggatgttg    4080
ctaacgagtg cagattattc aataacagct cttgaacagt taatttgcac agttgcaatt    4140
gtccagagtc ctgtccatta gaaagggact ctgtatccta tttgcacgct acaatgtggg    4200
ctgatcaccc aaggactctt cttgtgcatt gatgttcata attgtatttg tccacgatct    4260
tgtgcactaa ccccttccact ccctttgtat tccagcaggg gacccttact actcaagacc    4320
tctgtactag gacagtttat gtgcacaatc ctaattgatt agaactgagt cttttatatc   4380
aaggtccctg catcatcttt gctttacatc aagagggtgc tggttaccta atgcccctcc    4440
tccagaaatt attgatgtgc aaaatgcaat ttccctatct gctgttagtc tggggtctca     4500 tccccctcata ttccttttgt cttacagcag ggggtacttg ggactgttaa tgcgcataat   4560
tgcaattatg gtctttttcca ttaaattaag atcccaactg ctcacaccct cttagcatta   4620
cagtagaggg tgctaatcac aaggacattt ctttttgtact gttaatgtgc tacttgcatt   4680
tgtccctctt cctgtgcact aaagaccca ctcacttccc tagtgttcag cagtggatga    4740
cctctagtca agacctttgc actaggatag ttaatgtgaa ccatggcaac tgatcacaac    4800
aatgtctttc agatcagatc cattttatcc tccttgtttt acagcaaggg atattaatta   4860
cctatgttac ctttccctgg gactatgaat gtgcaaaatt ccaatgttca tggtctctcc    4920
ctttaaacct atattctacc ccttttacat tatagaaagg gatgctggaa acccagagtc    4980
cttctcttgg gactcttaat gtgtatttct aattatccat gactcttaat gtgcatattt    5040
tcaattgcct aattgatttc aattgtctaa gacatttcaa atgtctaatt gattagaact     5100
```

```
gagtctttta tatcaagcta atatctagct tttatatcaa gctaatatct tgacttctca    5160
gcatcataga aggggtact gatttcctaa agtctttctt gaatttctat tatgcaaaat     5220
tgccctgagg ccgggtgtgg tggctcacac ctgtaatccc agcactttgg gaggctgagg    5280
tgggaagatc ccttactgcc aggagtttga gaccagcctg gccaacatta aaaaaaaaaa    5340
aaaaagtaag acaattgccc tggaatccca tcccctcac acctccttgg caaagcagca     5400
ggagtgctaa ctagctagtg cttcttctct tatactgctt aaatgcgcat aattagcagt    5460
agttgatgtg cccctatgtt agagtagaat cccgcttcct tgctccattt gcattactgc    5520
aggagcttct aactagcctg aattcactct cttggactgt taatgtgcat acttatattt    5580
gctgctgtac ttttttacca tgtaaggacc ccacccactg tatttacatc ccagctggaa    5640
gtacctacta cttaagaccc ttagactagt aaagttagcg tgcataatct taggtgttat    5700
atacacattt tcagttgcat acagttgtgc cttttatcag gactcctgta cttatcaaag    5760
cagagagtgc taatcaatat taagcccttc tcttcgaact gtagatggca tgtaattgca    5820
gttgtcaatg gtccttcaat tagacttggg tttctgacct atcacaccct ctttgcttta    5880
ttgcatgggg tactattcac ttaaggcccc tttctcaaac tgttaatgtg cctaatgaca    5940
attacatcag tatccttcct tttgaaggac agcatggttg gtgacaccta aggcccatt    6000 tcttggcctc ccaatatgtg tgattgtatt tgtcgaggtt gctatgcact agagaaggaa    6060
agtgctcccc tcatccccac ttttcccttc cagcaggaag tgcccacccc ataagaccct    6120
tttatttgga gagtctaggt gcacaattgt aagtgaccac aagcatgcat cttggacatt    6180
tatgtgcgta atcgcacact gctcattcca tgtgaataag gtcctactct ccgaccctt     6240 ttgcaataca gaagggttgc tgataacgca gtccccttt cttggcatgt tgtgtgtgat     6300
tataatcgtc tgggatccta tgcactagaa aaggagggtc ctctccacat acctcagtct    6360 caccttccc ttccagcagg gagtgcccac tccataagac tctcacattt ggacagtcaa     6420
ggtgcgtaat tgttaagtga acacaaccat gcaccttaga catggatttg cataactaca    6480
cacagctcaa cctatctgaa taaaatccta ctctcagacc ccttttgcag tacagcaggg    6540
gtgctgatca ccaaggccct ttttcctggc ctggtatgcg tgtgattatg tttgtcccgg    6600
ttcctgtgta ttagacatgg aagcctcccc tgccacactc cacccccaat cttccttttcc   6660 cttccggcag gagtgccctc tccataagac gcttacgttt ggacaatcaa ggtgcacagt    6720
tgtaagtgac cacaggcata caccttggac attaatgtgc ataaccactt tgcccattcc    6780
atctgaataa ggtcctactc tcagacccct tttgcagtac agcaggggtg ctgatcacca    6840
aggccccttt tcttggcctg ttatgtgcgt gattatattt gtctgggttc ctgtgtatta    6900
gacaaggaag cctccccccc gccccacccc ccactcccag tcttcctttc ccttccagca    6960
gggagtgccc cctccataag atcattacat ttggacaatc aaggtgcaca attataagtg    7020
accacagcca tgcaccttgg acattattgg acattaatgt gcgtaactgc acatggccca    7080
tcccatctga ataaggacct actctcagat gcctttgcag tacagcaggg gtactgaatc    7140
accaaggccc ttttttcttgg cctgttatgt gtgtgattat attttatccca gtttctgtgt   7200 aatagacatg aaagcctccc ctgccacacc ccacctccaa tcttcctttc ccttccacca    7260
gggagtgtcc actccatata ccccttacatt tggacaatca aggtgcacaa ttgtaagtga    7320
gcataggcac tcaccttgga catgaatgtg cataactgca catggcccat cccatctgaa    7380
taaggtccta ctctcagacc cttttgcag tacagcaggg gtgctgatca ccaaggcccc    7440
ttttcctggc ctgttatgtg tgtgattata tttgttccag ttcctgtgta atagacatgg    7500
```

```
aagcctcccc tgccacactc caccccccaat cttcctttcc ttctggcagg aagtacccgc   7560
tccataagac ccttacattt ggacagtcaa ggtgcacaat tgtatgtgac cacaaccatg   7620
caccttggac ataaatgtgt gtaactgcac atggcccatc ccatctgaat aaggtcctac   7680
tctcagaccc cttttgcagt acagtaggtg tgctgataac caaggcccct cttcctggcc   7740
tgttaacgta tgtgattata tttgtctggg ttccagtgta taagacatgg aagcctcccc   7800
tgccccaccc caccctcaat cttcctttcc cttctggcag ggagtgccag ctccataaga   7860
accttacatt tggacagtca aggtgcacaa ttctaagtga ccgcagccat gcaccttggt   7920
caataatgtg tgtaactgca cacggcctat ctcatctgaa taaggcctta ctctcagacc   7980
ccttttgcag tacagcaggg gtgctgataa ccaaggccca ttttcctggc ctgttatgtg   8040
tgtgattata tttgtccagg tttctgtgta ctagacaagg aagcctcctc tgccccatcc   8100
catctacgca taatctttct tttcctccca gcagggagtg ctcactccat aagaccctta   8160
catttggaca atcaaggtgc acaattgtaa gtgaccacaa ccatgcatct tggaaattta   8220
tgtgcataac tgcacatggc ttatcctatt tgaataaagt cctactctca gacccccttt   8280
gcagtatagc tggggtgctg atcactgagg cctctttgct tggcttgtct atattcttgt   8340
gtactagata agggcacctt ctcatggact ccctttgctt ttcaacaagg agtacccact   8400 acttttttaag attcttatat ttgtccaaag tacatggttt taattgacca caacaatgtc   8460
ccttggacat taatgtatgt aatcaccaca tggttcatcc taattaaaca aagttctacc   8520
ttctcaccct ccatttgcag tataccaggg ttgctgaccc cctaagtccc ctttttcttgg   8580 cttgttgaca tgcataattg catttatgtt ggttcttgtg ccctagacaa ggatgcccca   8640
cctcttttca atagtgggtg cccactcctt atgatcttta catttgaaca gttaatgtga   8700
ataattgcag ttgtccacaa ccctatcact tctaggacca ttatacctct tttgcattac   8760
tgtggggtat actgtttccc tccaaggccc cttctggtgg actatcaaca tataattgaa   8820 attttcttttt gtctttgtca gtagattaag gtcatacccc atcacctttc ctttgtagta   8880
caacagggtg tcctgatcaa ccaaagtcct gttgttttgg actgttaata tgtgcaatta   8940
catttgctcc tgatctgtgc actagataag gatcctacct actttcttag tgttttttagc   9000 aggtagtgcc cactactcaa gactgtcact tggaatgttc atgtgcacaa actcaattct   9060
ctaagcatgt tcctgtacca ccttttgcttt agagcagggg gatgatattc actaagtgcc   9120
ccttcttttg gacttaatat gcattaatgc aattgtccac ctcttctttt agactaagag   9180
ttgatctcca catattcccc ttgcatcagg ggcatgttaa ttatgaatga acccttttct   9240
tttaatatta atgtcataat tgtatttgtg gacctgtgta ggagaaaaag accctatgtt   9300
cctcccatta ccctttggat tgctgctgag aagtgttaac tactcataat ctcagctctt   9360
ggacaattaa tagcattaat aacaattatc aagggcactg atcattagat aagactcctg   9420
cttcctcgtt gcttacatcg ggggtactga cccactaagg ccccttgtac tgttaatgtg   9480
aatatttgca attatatatg tctccttctg gtagagtggg atattatgcc ctagtatccc   9540
ctttgcatta ctgcagggc tgctgactac tcaaaacttc tcctgggact gttaataggc   9600
acaatggcag ttatcaatgg ttttctccct ccctgacctt gttaagcaag cgccccaccc   9660
cacccttagt ttcccatggc ataataaagt ataagcattg gagtattcca tgcacttgtc   9720
tatcaaacag tggtccatac tcccaaccct tttgcattgc gccagtgtgt aaaatcacag   9780
gtagccatgg tgtcatgctt tatatacgaa gtcttccctc tctctgcccc ttgtgtgccc   9840 ttggccccctt tttacagact attgctcaca atctcaggtg tccatatttg cagctattag   9900
```

```
gtaagattgt gctgtctccc tcttcccttc cctctgccct gcccttttg cctctttgct    9960 gggtaatgtt gaccagacaa ggccctttct cttggactta acaattctc agttgcactt   10020 tccttggtcc acccattata catgaacccc tctacttcct ttcgcattgc ttctgagtat   10080
gctgactacc caaagcccct tctgtgttat taataaacac agtactgatt gtcccatttt   10140
tcagcccatc agtccaagat ctccctacca cttggtgtg ttggtgcagt gttgactatg    10200
aaaagcaggc ctgaactagg tggataagcc ttcactcatt ttctttcatt tattaatgat   10260
cctagtttca attattgtca gattctgggg acaagaacca ttcttgccca cctgtgttac   10320
tgctttactg tgcaaaatac tgaaggcaag tcagacccag ggagctggat tgccatcctt   10380
tattttgtgt ttccagtgta cactataaaa ttgtctcccc aggaaggaag gttggcactt   10440
tctctgcatt cttcttttcca gagcagattg cctggttaag aatctcttgt tgtcccttct   10500
gtatattgtt attgtaaagt gccaaatgcc aggatacagc cagaaaaatt gcttattatt   10560
attaaaaaaa ttttttttaag aaagacatct ggattgtagg gtggactcga taacctggtc   10620
attatttttt tgaagccaaa atatccattt atactatgta cctggtgacc agtgtctctc   10680
attttaactg agggtggtgg gtctgtggat agaacactga ctcttgctat tttaatatca   10740
aagatattct agagtggaac tcttaagacc agtatctttg tgtgggcttt accagcattc   10800
acttttagaa aaactaccta aattttataa tcctttaatt tcttcatctg gagcacctgc   10860
ccctacttat ttcaagaaga ttgcagtaaa acgattaaat gagggaacat atgcagaggt   10920
gcttttaaaa agcatatgcc accttttta ttaattatta tataaaatga agcatttaat    10980
tatagtaata atttgaagta gtttgaagta ccacactgag gtgaggactt aaaaatgata   11040
agacgagttc cctattttat aagaaaaata agccaaaatt aaatattctt ttggatataa   11100
atttcaacag tgagatagct gcctagtgga aatgaataat atcccagcca ctagtgtaca   11160
gggtgttttg tggcacagga ttatgtaata tggaactgct caagcaaata actagtcatc   11220
acaacagcag ttctttgtaa taactgaaaa agaatattgt ttctcggaga aggatgtcaa   11280
aagatcggcc cagctcaggg agcagtttgc cctactagct cctcggacag ctgtaaagaa   11340
gagtctctgg ctctttagaa tactgatccc attgaagata ccacgctgca tgtgtcctta   11400
gtagtcatgt ctccttaggc tcctcttgga cattctgagc atgtgagacc tgaggactgc   11460
aaacagctat aagaggctcc aaattaatca tatctttccc tttgagaatc tggccaagct   11520
ccagctaatc tacttggatg ggttgccagc tatctggaga aaaagatctt cctcagaaga   11580
ataggcttgt tgttttacag tgttagtgat ccattccctt tgacgatccc taggtggaga   11640
tggggcatga ggatcctcca ggggaaaagc tcactaccac tgggcaacaa ccctaggtca   11700
ggaggttctg tcaagatact ttcctggtcc cagataggaa gataaagtct caaaacaac    11760 caccacacgt caagctcttc attgttccta tctgccaaat cattatactt cctacaagca   11820
gtgcagagag ctgagtcttc agcaggtcca agaaatttga acacactgaa ggaagtcagc   11880
cttcccacct gaagatcaac atgcctggca ctctagcact tgaggatagc tgaatgaatg   11940
tgtatttctt tgtctctttc tttcttgtct ttgctctttg ttctctatct aaagtgtgtc   12000
ttacccattt ccatgtttct cttgctaatt tctttcgtgt gtgcctttgc ctcatttct    12060 cttttgttc acaagagtgg tctgtgtctt gtcttagaca tatctctcat ttttcatttt    12120
gttgctattt ctctttgctc tcctagatgt ggctcttctt tcacgcttta tttcatgtct   12180 ccttttggg tcatgctg tgtgcttttt gtcttttct tgttctgtct acctctcctt       12240
tctctgccta cctctctttt ctctttgtga actgtgatta tttgttaccc cttccccttc   12300
```

```
tcgttcgttt taaatttcac cttttttctg agtctggcct cctttctgct gtttctactt    12360
tttatctcac atttctcatt tctgcatttc ctttctgcct ctcttgggct attctctctc    12420
tcctcccctg cgtgcctcag catctcttgc tgtttgtgat tttctatttc agtattaatc    12480
tctgttggct tgtatttgtt ctctgcttct tcccttccta ctcacctttg agtatttcag    12540
cctcttcatg aatctatctc cctctctttg atttcatgta atctctcctt aaatatttct    12600
ttgcatatgt gggcaagtgt acgtgtgtgt gtgtcatgtg tggcagaggg gcttcctaac    12660
ccctgcctga taggtgcaga acgtcggcta tcagagcaag cattgtggag cggttcctta    12720
tgccaggctg ccatgtgaga tgatccaaga ccaaaacaag gccctagact gcagtaaaac    12780
ccagaactca agtagggcag aaggtggaag gctcatatgg atagaaggcc caaagtataa    12840
gacagatggt ttgagacttg agacccgagg actaagatgg aaagcccatg ttccaagata    12900
gatagaagcc tcaggcctga aaccaacaaa agcctcaaga gccaagaaaa cagagggtgg    12960
cctgaattgg accgaaggcc tgagttggat ggaagtctca aggcttgagt tagaagtctt    13020
aagacctggg acaggacaca tggaaggcct aagaactgag acttgtgaca caaggccaac    13080
gacctaagat tagcccaggg ttgtagctgg aagacctaca acccaaggat ggaaggcccc    13140
tgtcacaaag cctacctaga tggatagagg acccaagcga aaaaggtatc tcaagactaa    13200
cggccggaat ctggaggccc atgacccaga acccaggaag gatagaagct tgaagacctg    13260
gggaaatccc aagatgagaa ccctaaaccc tacctctttt ctattgttta cacttcttac    13320
tcttagatat ttccagttct cctgtttatc tttaagcctg attcttttga gatgtacttt    13380
ttgatgttgc cggttacctt tagattgaca gtattatgcc tgggccagtc ttgagccagc    13440
tttaaatcac agcttttacc tatttgttag gctatagtgt tttgtaaact tctgtttcta    13500
ttcacatctt ctccacttga gagagacacc aaaatccagt cagtatctaa tctgctttt    13560 gttaacttcc ctcaggagca gacattcata taggtgatac tgtatttcag tcctttcttt    13620
tgaccccaga agccctagac tgagaagata aaatggtcag gttgttgggg aaaaaaaaag    13680
tgccaggctc tctagagaaa aatgtgaaga gatgctccag gccaatgaga agaattagac    13740
aagaaataca cagatgtgcc agacttctga gaagcacctg ccagcaacag cttccttctt    13800
tgagcttagg tgagcaggat tctggggttt gggatttcta gtgatggtta tggaaagggt    13860
gactgtgcct gggacaaagc gaggtcccaa ggggacagcc tgaactccct gctcatagta    13920
gtggccaaat aatttggtgg actgtgccaa cgctactcct gggtttaata cccatctcta    13980
ggcttaaaga tgagagaacc tgggactgtt gagcatgttt aatactttcc ttgattttt    14040 tcttcctgtt tatgtgggaa gttgatttaa atgactgata atgtgtatga aagcactgta    14100
aaacataaga gaaaaccaa ttagtgtatt ggcaatcatg cagttaacat ttgaaagtgc    14160
agtgtaaatt gtgaagcatt atgtaaatca ggggtccaca gttttctgt aagggg tcaa    14220 atcataaata cttagactg tgggccatat ggttctgtt acatatttgt tttttaaaca    14280 acgttttat aaggtcaaaa tcattcttag ttttgagcc aattggattt ggcctgctgt    14340
tcatagctta ccacccctg atgtattatt tgttattcag agaaaatttc tgaatactac    14400 tagttttcctt ttctgtgcct gtccctgtgc taggcactaa aaatgcaatg attattgata    14460
tctaggtgac ctgaaaaaaa atagtgaatg tgctttgtaa actgtaaagc acttgtattc    14520
tactgtgata agcgttgtgg atacaaagaa aggagcaagc ataaaaagt gctctttcaa    14580 aaggatatag tactatgcag acacaaggaa ttgtttgata aatgaataaa ttatatgtat    14640
atttgaggcc aatttgtgtt tgctgctctg gtaatttga gtaaaaatgc agtattccag    14700
```

-continued

```
gtatcagaaa cgaaaacaca tggaaactgc ttttaaactt taaaatatac tgaaaacata    14760
agggactaag cttgttgtgg tcacctataa tgtgccagat accatgctgg gtgctagagc    14820
taccaaaggg ggaaaagtat tctcatagca acaaaaaatt tcagaaaggt gcatattaaa    14880
gtgctttgta aactaaagca tgatacaaat gtcaatgggc tacatattta tgaatgaatg    14940
aatggatgaa tgaatattaa gtgcctctta cataccagct attttgggta ctgtaaaata    15000
caagattaat tctcctatgt aataagagga agtttatcc tctatactat tcagatgtaa    15060
ggaatgatat attgcttaat tttaaacaat caagacttta ctggtgaggt taagttaaat    15120
tattactgat acattttcc aggtaaccag gaaagagcta gtatgaggaa atgaagtaat    15180
agatgtgaga tccagaccga aagtcactta attcagcttg cgaatgtgct ttctaaatta    15240
taaagcactt gtaaatgaaa aatttgatgc tttctgtatg aataaaactt tctgtaagct    15300
aggtattgtc tctacaaaat tctcattgta tagttaaacc acagtgagaa gggttctata    15360
agtagttata caaccaagg gtttaaatac ctgttaaata gatcaatttt gattgcctac    15420
tatgtgaact cactgttaaa ggcactgaaa atttatcata tttcatttag ccacagccaa    15480
aaataaggca atacctatgt tagcattttg tgaactctaa ggcaccatat aaatgtaact    15540
gttgattttc tcacttggtg ctgggtacta ggtttataaa attgtatgat agttattata    15600
ttgtgcaaat aaagtaggaa aatttgaata acaatgatta tcttttgaat acgcatacgc    15660
aagggattgg ttgtctgaag aatgccacta tagtagttat ctattgtgtg ccaatctcat    15720
tgctaggcat tggggatgca aagataaacc atctttattg tgtcttgggt agcagaagaa    15780
aatatgtgta aaatcaattt ataatttgta aactgccacc catatataag ctatatctgc    15840
tgaatgatca ttgattactc ttatccttag agataacaac tgggggcaca aacatttatt    15900
atcattattg aacctacaac agagatctat gtgtagattt acgaagccta cagttctata    15960
cagataggaa tgaactattg gcttactgaa tggtgattac tttctgtggg gctcggaact    16020
acatgcccta ggatataaaa atgatgttat cattatagag tgctcacaga aggaaatgaa    16080
gtaatatagg tgtgagatcc agaccaaaag ttatttaaca agtttattca gtgatgaaaa    16140
catgggacaa atggactata taaggcagtg tactaagctg agtagagaga taagtcctg    16200 tccagaagat acatgctttc ctggcctgat tgaggagatg gaaatttttt gcaaaaaaca    16260
aggtgtttgt ggtcttccat ccagtttctt aagtgctgat gataaaagtg aattagaccc    16320
accttgacct ggcctacaga agtaaaggag taaaaataaa tgcctcaggc gtgcttttg    16380 attcatttga taaacaaagc atcttttatg tggaatatac cattctgggt cctgaggata    16440
agagagatga gggcattaga tcactgacag ctgaagatag a                         16481
```

<210> SEQ ID NO 2
<211> LENGTH: 32094
<212> TYPE: DNA
<213> ORGANISM: Homo sapiens

<400> SEQUENCE: 2

```
cttcagttct taaagcgctg caattcgctg ctgcagccat atttcttact ctctcggggc       60
tggaagcttc ctgactgaag atctctctgc acttggggtt cttttctagaa catttttctag    120 tcccccaaca ccctttatgg cgtatttctt taaaaaaatc acctaaattc cataaaatat      180
ttttttaaat tctatacttt ctcctagtgt cttcttgaca cgtcctccat atttttttaa      240
agaaagtatt tggaatattt tgaggcaatt tttaatattt aaggaatttt ctttggaat      300 cattttggt tgacatctct gttttttgtg gatcagtttt ttactcttcc actctctttt      360
```

```
ctatattttg cccatcgggg ctgcggatac ctggttttat tatttttctt ttgcccaacg    420
gggccgtgga tacctgcctt ttaattcttt tttattcgcc catcgggcc gcggatacct    480 gcttttatt ttttttccct tagcccatcg ggtatcgga tacctgctga ttcccttccc    540
ctctgaaccc ccaacactct ggcccatcgg ggtgacggga atctgctttt taaaaatttt    600
cttttttggg cccatcgggg cttcggatac ctgctttttt ttttttattt tttccttgcc    660
catcggggcc tcggataccct gctttaattt tgttttttct ggcccatcgg ggccgcggat    720
acctgctttg attttttttt ttcatcgccc atcggtgctt tttatggatg aaaaaatgtt    780
ggttttgtgg gttgttgcac tctctggaat atctacactt ttttttgctg ctgatcattt    840
ggtggtgtgt gagtgtacct accgctttgg cagagaatga ctctgcagtt aagctaaggg    900
cgtgttcaga ttgtggagga aaagtggccg ccattttaga cttgccgcat aactcggctt    960
agggctagtc gtttgtgcta agttaaacta gggaggcaag atggatgata gcaggtcagg    1020
cagaggaagt catgtgcatt gcatgagcta aacctatctg aatgaattga tttggggctt    1080
gttaggagct ttgcgtgatt gttgtatcgg gaggcagtaa gaatcatctt ttatcagtac    1140
aagggactag ttaaaaatgg aaggttagga aagactaagg tgcagggctt aaaatggcga    1200
ttttgacatt gcggcattgc tcagcatggc gggctgtgct ttgttaggtt gtccaaaatg    1260
gcggatccag ttctgtcgca gtgttcaagt ggcgggaagg ccacatcatg atgggcgagg    1320 cttttgttaag tggttagcat ggtggtggac atgtgcggtc acacaggaaa agatggcggc    1380
tgaaggtctt gccgcagtgt aaaacatggc gggcctcttt gtctttgctg tgtgcttttc    1440
gtgttgggtt ttgccgcagg gacaatatgg caggcgttgt catatgtata tcatggcttt    1500
tgtcacgtgg acatcatggc gggcttgccg cattgttaaa gatggcgggt tttgccgcct    1560
agtgccacgc agagcgggag aaaaggtggg atggacagtg ctggattgct gcataaccca    1620
accaattaga aatgggggtg gaattgatca cagccaatta gagcagaaga tggaattaga    1680
ctgatgacac actgtccagc tactcagcga agacctgggt gaattagcat ggcacttcgc    1740
agctgtcttt agccagtcag gagaaagaag tggagggggcc acgtgtatgt ctcccagtgg    1800
gcggtacacc aggtgttttc aaggtctttt caaggacatt tagcctttcc acctctgtcc    1860
cctcttattt gtcccctcct gtccagtgct gcctcttgca gtgctggata tctggctgtg    1920
tggtctgaac ctccctccat tcctctgtat tggtgcctca cctaaggcta agtatacctc    1980
cccccccacc ccccaacccc cccaactccc caccccacc ccccacccc cacctcccca    2040 cccccctacc ccctacccc cctacccccc tctggtctgc cctgcactgc actgttgcca    2100
tgggcagtgc tccaggcctg cttggtgtgg acatggtggt gagccgtggc aaggaccaga    2160
atggatcaca gatgatcgtt ggccaacagg tggcagaaga ggaattcctg ccttcctcaa    2220
gaggaacacc tacccttgg ctaatgctgg ggtcggattt tgatttatat ttatcttttg    2280
gatgtcagtc atacagtctg attttgtggt ttgctagtgt ttgaatttaa gtcttaagtg    2340
actattatag aaatgtatta agaggcttta tttgtagaat tcactttaat tacatttaat    2400 gagttttgt tttgagttcc ttaaaattcc ttaaagtttt tagcttctca ttacaaattc    2460
cttaaccttt ttttggcagt agatagtcaa agtcaaatca tttctaatgt tttaaaaatg    2520
tgctggtcat tttctttgaa attgacttaa ctatttccct ttgaagagtc tgtagcacag    2580
aaacagtaaa aaatttaact tcatgaccta atgtaaaaaa gagtgtttga aggtttacac    2640
aggtccaggc cttgctttgt tcccatcctt gatgctgcac taattgacta atcacctact    2700
tatcagacag gaaacttgaa ttgctgtggt ctggtgtcct ctattcagac ttattatatt    2760
```

```
ggagtatttc aattttttcgt tgtatcctgc ctgcctagca tccagttcct ccccagccct    2820
gctcccagca aaccccctagt ctagcccccag ccctactccc acccccgcccc agccctgccc    2880 cagccccagt ccctaaccc cccagcccta gccccagtcc cagtcctagt tcctcagtcc    2940
cgcccagctt ctctcgaaag tcactctaat tttcattgat tcagtgctca aaataagttg    3000
tccattgctt atcctattat actgggatat tccgtttacc cttggcattg ctgatcttca    3060
gtactgactc cttgaccatt tcagttaat gcatacaatc ccatttgtct gtgatctcag    3120
gacaaagaat tccttactc ggtacgttga agttagggaa tgtcaattga gagctttcta    3180
tcagagcatt attgcccaca atttgagtta cttatcattt tctcgatccc ctgcccttaa    3240
aggagaaacc atttctctgt cattgcttct gtagtcacag tcccaatttt gagtagtgat    3300
cttttcttgt gtactgtgtt ggccacctaa aactctttgc attgagtaaa attctaattg    3360
ccaataatcc tacccattgg attagacagc actctgaacc ccatttgcat tcagcagggg    3420
gtcgcagaca acccgtcttt tgttggacag ttaaaatgct cagtcccaat tgtcatagct    3480
ttgcctatta aacaaaggca ccctactgcg cttttttgctg tgcttctgga gaatcctgct    3540
gttcttggac aattaaagaa caaagtagta attgctaatt gtctcaccca ttaatcatga    3600
agactaccag tcgcccttgc atttgccttg aggcagcgct gactacctga gatttaagag    3660
tttcttaaat tattgagtaa aatcccaatt atccatagtt ctgttagtta cactatggcc    3720
tttgcaaaca tctttgcata acagcagtgg gactgactca ttcttagagc cccttccctt    3780
ggaatattaa tggatacaat agtaattatt catggttctg cgtaacagag aagacccact    3840
tatgtgtatg cctttatcat tgctcctaga tagtgtgaac tacctaccac cttgcattaa    3900
tatgtaaaac actaattgcc catagtccca ctcattagtc taggatgtcc tctttgccat    3960
tgctgctgag ttctgactac ccaagtttcc ttctcttaaa cagttgatat gcataattgc    4020
atatattcat ggttctgtgc aataaaaatg gattctcacc ccatcccacc ttctgtggga    4080
tgttgctaac gagtgcagat tattcaataa cagctcttga acagttaatt tgcacagttg    4140
caattgtcca gagtcctgtc cattagaaag ggactctgta tcctatttgc acgctacaat    4200
gtgggctgat cacccaagga ctcttcttgt gcattgatgt tcataattgt atttgtccac    4260
gatcttgtgc actaaccctt ccactcccctt tgtattccag caggggaccc ttactactca    4320
agacctctgt actaggacag tttatgtgca caatcctaat tgattagaac tgagtctttt    4380
atatcaaggt ccctgcatca tctttgcttt acatcaagag ggtgctggtt acctaatgcc    4440
cctcctccag aaattattga tgtgcaaaat gcaatttccc tatctgctgt tagtctgggg    4500
tctcatcccc tcatattcct tttgtcttac agcagggggt acttgggact gttaatgcgc    4560
ataattgcaa ttatggtctt ttccattaaa ttaagatccc aactgctcac accctcttag    4620
cattacagta gagggtgcta atcacaagga catttctttt gtactgttaa tgtgctactt    4680
gcatttgtcc ctcttcctgt gcactaaaga ccccactcac ttccctagtg ttcagcagtg    4740
gatgacctct agtcaagacc tttgcactag atagttaat gtgaaccatg gcaactgatc    4800
acaacaatgt ctttcagatc agatccattt tatcctcctt gttttacagc aagggatatt    4860
aattacctat gttacctttc cctgggacta tgaatgtgca aaattccaat gttcatggtc    4920 tctccctttta aacctatatt ctaccccttt tacattatag aaagggatgc tggaaaccca    4980
gagtccttct cttgggactc ttaatgtgta tttctaatta tccatgactc ttaatgtgca    5040
tattttcaat tgcctaattg atttcaattg tctaagacat ttcaaatgtc taattgatta    5100
gaactgagtc tttatatca agctaatatc tagctttat atcaagctaa tatcttgact    5160
```

```
tctcagcatc atagaagggg gtactgattt cctaaagtct ttcttgaatt tctattatgc    5220
aaaattgccc tgaggccggg tgtggtggct cacacctgta atcccagcac tttgggaggc    5280
tgaggtggga agatccctta ctgccaggag tttgagacca gcctggccaa cattaaaaaa    5340
aaaaaaaagt aagacaattg ccctggaatc catcccccct cacacctcct tggcaaagca    5400
gcaggagtgc taactagcta gtgcttcttc tcttatactg cttaaatgcg cataattagc    5460
agtagttgat gtgccctat gttagagtag aatcccgctt ccttgctcca tttgcattac    5520
tgcaggagct tctaactagc ctgaattcac tctcttggac tgttaatgtg catacttata    5580
tttgctgctg tacttttta ccatgtaagg accccaccca ctgtatttac atcccagctg    5640
gaagtaccta ctacttaaga cccttagact agtaaagtta gcgtgcataa tcttaggtgt    5700
tatatacaca ttttcagttg catacagttg tgccttttat caggactcct gtacttatca    5760
aagcagagag tgctaatcaa tattaagccc ttctcttcga actgtagatg gcatgtaatt    5820
gcagttgtca atggtccttc aattagactt gggtttctga cctatcacac cctctttgct    5880
ttattgcatg gggtactatt cacttaaggc ccctttctca aactgttaat gtgcctaatg    5940
acaattacat cagtatcctt cctttgaag gacagcatgg ttggtgacac ctaaggcccc    6000
atttcttggc ctcccaatat gtgtgattgt atttgtcgag gttgctatgc actagagaag    6060
gaaagtgctc ccctcatccc cacttttccc ttccagcagg aagtgcccac cccataagac    6120
ccttttattt ggagagtcta ggtgcacaat tgtaagtgac cacaagcatg catcttggac    6180
atttatgtgc gtaatcgcac actgctcatt ccatgtgaat aaggtcctac tctccgaccc    6240
cttttgcaat acagaagggt tgctgataac gcagtcccct tttcttggca tgttgtgtgt    6300
gattataatc gtctgggatc ctatgcacta gaaaggagg gtcctctcca catacctcag    6360
tctcaccttt cccttccagc agggagtgcc cactccataa gactctcaca tttggacagt    6420
caaggtgcgt aattgttaag tgaacacaac catgcacctt agacatggat ttgcataact    6480
acacacagct caacctatct gaataaaatc ctactctcag ccccttttg cagtacagca    6540 ggggtgctga tcaccaaggc cttttttcct ggcctggtat gcgtgtgatt atgtttgtcc    6600
cggttcctgt gtattagaca tggaagcctc ccctgccaca ctccaccccc aatcttcctt    6660
tcccttccgg cagggagtgc cctctccata agacgcttac gtttggacaa tcaaggtgca    6720
cagttgtaag tgaccacagg catacacctt ggacattaat gtgcataacc actttgccca    6780
ttccatctga ataaggtcct actctcagac cccttttgca gtacagcagg ggtgctgatc    6840
accaaggccc cttttcttgg cctgttatgt gcgtgattat atttgtctgg ttcctgtgt    6900 attagacaag gaagccttcc ccccgccccc accccactc ccagtcttcc tttcccttcc    6960
agcagggagt gcccctcca taagatcatt acatttggac aatcaaggtg cacaattata    7020
agtgaccaca gccatgcacc ttggacatta ttggacatta atgtgcgtaa ctgcacatgg    7080
cccatcccat ctgaataagg tcctactctc agatgcccct tgcagtacag cagggggtact    7140 gaatcaccaa ggccctttt cttggcctgt tatgtgtgtg attatattta cccagtttc    7200 tgtgtaatag acatgaaagc ctcccctgcc acacccacc tccaatcttc ctttcccttc    7260
caccagggag tgtccactcc atatacccctt acatttggac aatcaaggtg cacaattgta    7320
agtgagcata ggcactcacc ttggacatga atgtgcataa ctgcacatgg cccatcccat    7380
ctgaataagg tcctactctc agaccctttt tgcagtacag caggggtgct gatcaccaag    7440 gcccctttc ctggcctgtt atgtgtgtga ttatatttgt tccagttcct gtgtaataga    7500
catggaagcc tcccctgcca cactccaccc ccaatcttcc tttcccttct ggcaggaagt    7560
```

```
acccgctcca taagacccct acatttggac agtcaaggtg cacaattgta tgtgaccaca    7620
accatgcacc ttggacataa atgtgtgtaa ctgcacatgg cccatcccat ctgaataagg    7680
tcctactctc agacccsttt tgcagtacag taggtgtgct gataaccaag gcccctcttc    7740
ctggcctgtt aacgtatgtg attatatttg tctgggttcc agtgtataag acatggaagc    7800
ctcccctgcc ccaccccacc ctcaatcttc ctttcccttc tggcagggag tgccagctcc    7860
ataagaacct tacatttgga cagtcaaggt gcacaattct aagtgaccgc agccatgcac    7920
cttggtcaat aatgtgtgta actgcacacg gcctatctca tctgaataag gccttactct    7980
cagacccctt ttgcagtaca gcaggggtgc tgataaccaa ggcccatttt cctggcctgt    8040
tatgtgtgtg attatatttg tccaggtttc tgtgtactag acaaggaagc ctcctctgcc    8100
ccatcccatc tacgcataat ctttcttttc ctcccagcag ggagtgctca ctccataaga    8160
cccttacatt tggacaatca aggtgcacaa ttgtaagtga ccacaaccat gcatcttgga    8220
aatttatgtg cataactgca catggcttat cctatttgaa taaagtccta ctctcagacc    8280
cccttttgcag tatagctggg gtgctgatca ctgaggcctc tttgcttggc ttgtctatat    8340
tcttgtgtac tagataaggg caccttctca tggactccct ttgcttttca acaaggagta    8400
cccactactt tttaagattc ttatatttgt ccaaagtaca tggttttaat tgaccacaac    8460
aatgtccctt ggacattaat gtatgtaatc accacatggt tcatcctaat taaacaaagt    8520
tctaccttct caccctccat ttgcagtata ccaggggttgc tgacccccta agtcccsttt    8580
tcttggcttg ttgacatgca taattgcatt tatgttggtt cttgtgccct agacaaggat    8640
gccccacctc ttttcaatag tgggtgccca ctccttatga tctttacatt tgaacagtta    8700
atgtgaataa ttgcagttgt ccacaaccct atcacttcta ggaccattat acctcttttg    8760
cattactgtg gggtatactg tttcccctcca aggccccttc tggtggacta tcaacatata    8820
attgaaattt tcttttgtct ttgtcagtag attaaggtca tacccsatca cctttccttt    8880
gtagtacaac agggtgtcct gatcaaccaa agtcctgttg ttttggactg ttaatatgtg    8940
caattacatt tgctcctgat ctgtgcacta gataaggatc ctacctactt tcttagtgtt    9000
tttagcaggt agtgcccact actcaagact gtcacttgga atgttcatgt gcacaaactc    9060
aattctctaa gcatgttcct gtaccacctt tgctttagag cagggggatg atattcacta    9120
agtgcccctt cttttggact taatatgcat taatgcaatt gtccacctct tcttttagac    9180
taagagttga tctccacata ttccccttgc atcaggggca tgttaattat gaatgaaccc    9240
tttctcttta atattaatgt cataattgta tttgtggacc tgtgtaggag aaaaagaccc    9300
tatgttcctc ccattaccct ttggattgct gctgagaagt gttaactact cataatctca    9360
gctcttggac aattaatagc attaataaca attatcaagg gcactgatca ttagataaga    9420
ctcctgcttc ctcgttgctt acatcggggg tactgaccca ctaaggcccc ttgtactgtt    9480
aatgtgaata tttgcaatta tatatgtctc cttctggtag agtgggatat tatgccctag    9540
tatccccttt gcattactgc aggggctgct gactactcaa aacttctcct gggactgtta    9600
ataggcacaa tggcagttat caatggtttt ctccctccct gaccttgtta agcaagcgcc    9660
ccaccccacc cttagtttcc catggcataa taaagtataa gcattggagt attccatgca    9720
cttgtctatc aaacagtggt ccatactccc aacccttttg cattgcgcca gtgtgtaaaa    9780
tcacaggtag ccatggtgtc atgctttata tacgaagtct tccctctctc tgccccttgt    9840
gtgcccttgg cccctttta cagactattg ctcacaatct caggtgtcca tatttgcagc    9900
tattaggtaa gattgtgctg tctccctctt cccttccctc tgccctgccc cttttgcctc    9960
```

```
tttgctgggt aatgttgacc agacaaggcc ctttctcttg gacttaaaca attctcagtt    10020
gcactttcct tggtcccacc cattatacat gaacccctct acttcctttc gcattgcttc    10080
tgagtatgct gactacccaa agccccttct gtgttattaa taaacacagt actgattgtc    10140 ccattttca gcccatcagt ccaagatctc cctaccactt tggtgtgttg gtgcagtgtt    10200
gactatgaaa agcaggcctg aactaggtgg ataagccttc actcattttc tttcatttat    10260
taatgatcct agtttcaatt attgtcagat tctggggaca agaaccattc ttgcccacct    10320
gtgttactgc tttactgtgc aaaatactga aggcaagtca gacccaggga gctggattgc    10380
catcctttat tttgtgtttc cagtgtacac tataaaattg tctccccagg aaggaaggtt    10440
ggcactttct ctgcattctt ctttccagag cagattgcct ggttaagaat ctcttgttgt    10500
cccctttgta tattgttatt gtaaagtgcc aaatgccagg atacagccag aaaaattgct    10560
tattattatt aaaaaaattt ttttaagaaa gacatctgga ttgtagggtg gactcgataa    10620
cctggtcatt attttttga agccaaaata tccatttata ctatgtacct ggtgaccagt    10680
gtctctcatt ttaactgagg gtggtgggtc tgtggataga acactgactc ttgctatttt    10740
aatatcaaag atattctaga gtggaactct taagaccagt atctttgtgt gggctttacc    10800
agcattcact tttagaaaaa ctacctaaat tttataatcc tttaatttct tcatctggag    10860
cacctgcccc tacttatttc aagaagattg cagtaaaacg attaaatgag ggaacatatg    10920
cagaggtgct tttaaaaagc atatgccacc ttttttatta attattatat aaaatgaagc    10980
atttaattat agtaataatt tgaagtagtt tgaagtacca cactgagtg aggacttaaa    11040 aatgataaga cgagttccct atttataag aaaaataagc caaaattaaa tattcttttg    11100
gatataaatt tcaacagtga gatagctgcc tagtggaaat gaataatatc ccagccacta    11160
gtgtacaggg tgttttgtgg cacaggatta tgtaatatgg aactgctcaa gcaaataact    11220
agtcatcaca acagcagttc tttgtaataa ctgaaaaaga atattgtttc tcggagaagg    11280
atgtcaaaag atcggcccag ctcagggagc agtttgccct actagctcct cggacagctg    11340
taaagaagag tctctggctc tttagaatac tgtaagtact acttcgtagc tattaagtaa    11400 tcttttcct attctatttt ctttctctta gatgccacct atagaaaagt cagagggtcc    11460
agtaagtttc tttccttctt cccacctcat ctgcaatata tatatataga gagagaaata    11520
gatacataca tacatgcata aatacacata tgtgagttaa ccagcagaac tgtagaatta    11580
atattgtgga cccagctcta tgctaggtta cactgataac ctgggtagga atgatatcat    11640
cctatataat ttcattcctg agatgatttt atcgttgagg agctaatgtg agcacatttg    11700
aaataacttt agaaaataat aagtgctgtt ttgtgtgaat cataagtagt agttttagga    11760
agggaaccca caaggatttg aagttgatag aataaactta aggaagtggg tttgcttttt    11820
ctctttaagc caagatagga ttaatattgc agccatctgg atagtccagt tggtttattt    11880
taatttcatt tgttttttac ctcttttgga gccatggaaa gagatgaaag ggatagagca    11940
tagccattgt gtttggctat ttgcgaaggt tggcaaatta gtgattgcta aatctcataa    12000
gcttgagtat tttaaagttc agagattgag ggcataaatc taatacttcg gctccttcca    12060
caattttact acatttctgc ccaagaacag atgaccatgg ataatgcata tcgtagatac    12120
tttttaagtt tggaaccttt ttgccaagag ggtagtggag aagtgaagtc aaaaccttga    12180
ccttccttgc ctactttatg ctgtagttta tataccttct ttcctcccac ctttcgtaaa    12240
gctaaaagaa gcttagcctc cttaatgttt tccagctgac aaaatattgt ttaacataac    12300
attcgaaact ttttttctgg tgcacattca tgcatcacag caggagcaac aagaaccata    12360
```

```
taagtgaact ggcttcactt atagcccgtt ttaattcata tccatatttc ctcagggctt    12420
gtttccatgc ctcccagccc cactccatat gcttaacaac attgtctggc tgactgaggg    12480
ttatatacat catggtcttg aaccttcttg gaaacatggt ctgtgccatt gtttctcaaa    12540
cccaagtaat gcttcatgat gaaacacctt ctaaaggaac aaaattttct gagatcctaa    12600
aaaaatgtgt tttgaggaac actgacttaa caaagatatt tgaaatgtaa atatgttttc    12660
caatttcacg ttgtctttgt caaagatgtg ttttatataa cttatgtaga acttggggat    12720
ccattagaat atattcacaa atccccaggg ttatcacccc aatttgagaa accctggtct    12780
atgcttatga aatcttctat tggtaattaa attgtcattc attgtcaaca tacaattata    12840
attattattg gaatttgttt taaatgaatg aatttggagg tgattctgta ccttaagtca    12900
agaggaagga tggcttgatt ttaggtggat tgattatact agatagcatc caaaggtgaa    12960
tcttgaagct gtatttaaat tcattgcttg aaataatttc cacccttaag aaaaatctct    13020
agcaattgta aaaagggatg ctctggaaat gtgggcatct tcaaaataga gataattctt    13080
gtgttagttc aacaaatatt attgtaccag gtgctggaat aaatagcaaa accaaagaca    13140
ggatttatat caaggaattt gcttcttat ggaggatgca gaaggaaatc attatggttt    13200
tgggcagaaa tgcttagact ttagtcctgg ctctgagttt ggttcagatc accatcaatc    13260
tgaccatctc gagactgcta gtgaaataag atagggggctt atatcaaata cctaaatccc    13320
tgaaaatgac attttgtgat ttggaaaatt ttcaaaagtc taatgaagga aactttttg     13380 gcatttcttt aaatgattat tgtcatttct tttctgactt ttccctttat aaaaccttaa    13440
catgtaggat tggaggaagt tttctgacca ttttctcata tcctctttca gctttatctt    13500
tctgtaactt ccatttctct agccacctcc ctaaattaca gaagactgtg agacccaggg    13560
ctgctgtgat taggcattca taatttcttt tcagggtgtt tgtgccctga ttatcaaatg    13620
tacagcttga agggagttca tgtcttaaag taatgaatta agagttgacc tttgttgact    13680
gctaaaatat tcttatatgt gaaagcatcc tggaaaaata cgttaccagc ttaaagagaa    13740
agaaactaat gattatatct gaactgagct aatgcctctt ctcttccccc aaaccttatc    13800
agtttggatg gcaaagagta atgatgtgtc agttaaacag agctaatgcc ttcctctgcc    13860
ttgtcttaaa gactggattg ggagaaaatt gatattctca ctaccatatt tgggctgta    13920 ggcaagtagc attttacaca ggtttccttc aaaaatccaa ctcaagttgg agctcatgta    13980
tttaagacat agctggcctg ctgaattaa caagttaaac ttcagtggcc atgtacagtt    14040
atatatcact atatatatgt gtattaggct gtcgagttgg tcatgttttt gttggtgact    14100
taggctttac ttgatagctc ttccttgacc tttccaaatt gagtactgat acatggagct    14160
tgggcttctt ctgcatctta tacaaatgag tttggtaaag aagcctctcc tttactgttt    14220
tgatgtttat attagaaata acttttgatt attttttttc atgttaggat gagaaactga    14280
aacaaaatgt aaatttgacc ggtgctagac ttcttaaatt atgggtagac ttaaagtatt    14340
attttcctta accaattaga atgctagtct tctagtgttc ccggaaacat gagaggttat    14400
gcagtagacc caagcaatac cctcttatta cataatcaag tgcgtataag aatttaaaaa    14460
tagggatatg actggaacat cactgtactt taccaggtcc cattataaaa ttatctatgt    14520
tactttaccc atagctttga aaactagtgg catagtatat tttatagtat gctgttagtg    14580
tgattggcat tgaacagtga tgggatataa tcactctaca atctatatgt tattaaagtt    14640
ttccagcctt atagatctcc cttgactgaa aattagctac taacttacga cttattttt    14700 acagcagatt gactaggtct ttccaggaaa tctgttgatg tacaaaaaca aagtttaatt    14760
```

```
gctaatgttt ttttaaaaaa taacttttg atattacgga tacctggtta tttgggcctt    14820
gtatatttta acatcaaaat tacctattat aaatccatat aaacagaaaa gaaagagagt    14880
aagtctttag atcagatctg caaacaatga tggtacgtac tgtagaaaaa tctggaacat    14940
agacttacca gttcttaggt tccatttgc ttgcttttta aaaactgtgt cttataagtc    15000
ttcagcaact ggttgggaga tttttagaaa aataaccttt ttaatgttag aacagtgtag    15060
agatttacag aatgattctg aagatagagt ttctgtgtac ttcacaccca gttttttccca    15120
gtgttaacat tttacattag tttggtacat ttgtcacaac aaaccaatat tgatacatta    15180
ttattaacta gagtccatat tttattcaga tttccttagt ttttcttaa tgttcttttt    15240
gtgttccagg atcccattga agataccacg ctgcatgtgt ccttagtagt catgtctcct    15300
taggctcctc ttggtaatga cagtttctca gactctttgt ttttgatgaa cttcacagtt    15360
ttgaggacta atggtccagt attctataga atgtctctct attggaattt gtctgatgtt    15420
cttctcatga ctagattggg tttatgagtg tttaggagga agaccacaaa ggtagagtgc    15480
cattcttatc acttatcaag agtacatact atcaacatga cttatcactg tttatgttat    15540
ccttaatcac ctgtctgagg tactatttgt caggtttctc cagcgtaaaa ttagtctttta    15600
tttctccatt tccctactat actgttcaca taggaagtca ctatgtgcag ccagcactta    15660
aggaatggga aattccttc cacctcattg agggcagagt atttacataa attatttgga    15720
attcttttgc acaggatgtc ttttctccac aatgtattgt gtttattcag tcatttatat    15780
cagtatgatc tcagggatat tttatactct gggttataat acagtattac tttattctgt    15840
tgttcaaatt gttccagctt tggccattgg gaggtctttc atttggcttt gatataaccc    15900
catgaatgtg ggttttttgt ttgagcactt tcttatttt ggaactacaa catgcttcag    15960
actcatttgc atatctcctg cctggaccta aaatgatgta tttctgcaag gagccttgat    16020
acttttatt ggagagtaat attagaaatc aagaagtgaa tgctaggtgc gctcattact    16080
actggagtgt cattccttca agacctttc agttgacaag agcaaggaga tatatatttg    16140
cattctaacg tgtgtatatg cacatagcta taaatatata taaccatctg tatctatatt    16200
aaactaaatg tgtttatacc tacgtctcca actctaatca ttgccacatg gatcattata    16260
gtctcacctc cttgcttatc tgttacctcc catttctaca gtgagaaacc tggcttggtt    16320
gggaaattt tctgttaata ttacggtagt gagtgtttga catttgcttc tatggttaag    16380
tttagggaga gtttagctgt agggtattct tgaaactaga aatgacccctt ctgccctaaa    16440
tgtttctgcc agttttgaaa cgtaaaatag gttgcagaaa caaactttat cttaagaacc    16500
agaatttact tcaatccaca ttttgacatt gattttcaga ttaaattatt ctgatatcgc    16560
caggtaagct gttccttggg tatgcatttc ttctttccgt ttttttctaa gagctaaagg    16620
accctgagaa cactggaggt gggaaaggaa gggaaaggca tgttcacacg tgggatagga    16680
aaggttcatt tactgacctc cagctagcct tccaaagtgc ctatttaaga cccaaggagt    16740
agatgtcttc cttggcaatt gtaacccaaa tataattttt aacctttcaa ttttagtcaa    16800
gaaagttggt gtgctgttac aaaaagtgcc ctgattaaca gcattgtcat gtgcattgca    16860
tattaatcag caatttaaaa taacatgaaa ttatgttgag tataatttta atattttata    16920
ttagatatta gttgagaca gtgtttctca agtctgtata ataagtttga tagtagggag    16980
gttttctctc aagaaaagaa ttattcagtg tgcacctaca taatcactgc ttagattcta    17040
caattaatat tttgctatat ttgattaaac gttttctgta aaagaaaaat attattatgt    17100
actatttagg tttatgggaa taattgttaa gttaaagtgt atgaacaaac ctggaatgaa    17160
```

```
atctgtttgc ctacatctat aatacaacta taaaacatag cagatgtaca aattagtagt   17220
taatagataa ctaaaatgca aatatggcac tactattata gtattatagt ttcttttgag   17280
tggcgtgtct gtaatatcac atgctgtgtt gatgcacttc accaaactgc tgttttcaaa   17340
ctgctttaaa tcctgccatt atagcacata gcaatgctat ttcactttca tttggcacaa   17400
aacacattta tatattgttt gcttctcttc ttttctgtaa tccccaggca acaaaactag   17460
aacatttgcc actaatctgg caacgtggtc ctatattatg aagtagtcat atagctgatc   17520
taaactatcc ttacagtgaa atgagagtat tgtgaaagtt ttgtagaaag ctccccatat   17580
gtcctgagaa tctatgcaca gaccccacag ttaaaagacc tttgaattgt gggaagacat   17640
gggtttaagt atcacttggt taccttctat ttgtgtaaca ttgaggtagt ttcatcttct   17700
gggttcccag tttccttaga gaatgaaaat gttgaattat gtgattttt tttttttttg   17760 agacggagtt ttgctctttc gcccaggctg gagtgaagta gcacgatctc gactcactgc   17820
aacctccttc ccccatgatc aagcaattct cctgcctcag cctcccaagt agctgggatt   17880
acaggcaccc gcccccacc cccgccccc agctaatgtt tgtatttta gtacagatgg   17940 agttttgccg tgttggccag gctggtctcg aacttctgac ctcaggtgat ccactcgcct   18000
tggcctccca aagtgctagg attacaggca tgagccactg cgcctggcct atgtgattat   18060
taatatcacg tctagctgtg acaattctgt ctgatgctgg agtatttgaa ccagatggct   18120
ggctgtgcca ctcagttatt ctctccataa gactttgata ttttgttggt ctgcaagatg   18180
acggattctc aaaattcttg tcagtgaata ttgaaccta gtgaaatgta tggttctgta   18240
tcagttccaa aatgtaacca ctttctctag ccttagattc ccagttccaa aatgtaacca   18300
ttttctctag ccttagattc ccgttaaggg aaagggaatg ctctttgagt atgtcatcac   18360
catagtaaca ggcaaaacta gagggctttg atgctaaagc aagatactcc ataaatatgc   18420
ttaagaagac ttggggagac tggaatagtt gttccctttt agatgccagt gtataaatga   18480
atttgagcta ggatccgttt atttaaaatt tctttaggtg tatttgcttg catatggagt   18540
gcacatttac tctcattaat ggagttttag gaagcagtag agtaaatgca taaacatgta   18600
tgaaccgcca tgtttaactg gaagcctgca tttggaagtc aagtatctaa tcttagatta   18660
aattaggatg gggaaggatg ttggcaagag attttgaagc ttgttctgct tatattgaga   18720
acatcataga acagtttggc cttttttaaag ctagagaata gtgttgaata agtgatgttc   18780
catatattcc tgtttgacat tgacataaag gtttcctcat gatacagtaa tccctgatca   18840
gggatctgga agcctgtatt catttaaggt actcaggttt aacatactgg gtgcttttca   18900
caccatacta tacagtacca tgcaaagtgc tttcaagact gcaaatttgg cttagatccc   18960
ctttagtgag ctcctatgct atagtaaagg tagatagcca attattaaaa acagtcaaga   19020
caattgcacc tctaagcagt agtagcagtt gccacaccac cttgaatctt gaagtatttt   19080
cagcaacagg atgaccatta gccacaaatt tagtgtcagc ccttaaggtc ggtattggtt   19140
tgacccatat tttcatgtag ttcttttttct tcacttgtct aatcttcccg tgtactgcca   19200
gggcttgtca ttagaggact ttagggagac caagcaggct agaaagtaga gacaggagat   19260
acctatgtct aatgcttcag tttatacttc ctaggttttt ttcattgggg tttttgtaac   19320
tcttttggta tcctaccggt gctttggtag cctactgaac cctgtctttc ttcttaagga   19380
cattctgagc atgtgagacc tgaggactgc aaacagctat aagaggctcc aaattaatca   19440
tatctttccc tttgagaatc tggccaagct ccagctaatc tacttggatg ggttgccagc   19500
tatctggaga aaaaggtagt ttggggaatt tattgttgta gtgcttctgt ctttggattg   19560
```

```
aacttcccac aactctcctt tttaaagcag aacacagctg ggcatggtgg ctcctgcttg   19620
taattccagg gctttgggag gttgaggtgg ggggatcact tgaggccagg agttgaagac   19680
ccatgtctct acaataaaat aaaattagtt gggcatggtg gtacgtgcct gtagtcctac   19740
ctactctgga ggctgaggca gcaggattgc ttgagcccag gagttcaagg ctgcagtgag   19800
ccatcattag ccactgcact ccagcctagg tggcagagcg ggacccagtc tcttaaaaag   19860
aaagaaaagc agaacgtgag ccagttttca tcaattccta tacttttcct tttgcatgta   19920
cacatacatt ttaactttac ataatgagtt cggcctgttt catttatccc tcagagctgg   19980
gctccagtga ggtctgtaag ggcaagcata cttgatcccc aatgaagaat gagagatgca   20040
aagcactaaa ttatttcttt tctcaccaca cagcaagata gatttaatga acttaacacc   20100
ttttgattag tggccttta aattattccc actttccttt ggcagatggg tattaagttc   20160
tcaggatttg tttacaaata agactaactt catctgtatt agctcagttt tggtaggcct   20220
aattccatta tcactgccat ttccttgttt taagaaatca aaatttctta gcttgaaaaa   20280
caattgaaat tgttaaaaag tggaatagga gagccccggg ggcctgtata aggaatttac   20340
tgaatccctg gttttctgta ccttgttttt ccttctgcat agatttgctt aactgttttt   20400
gtggcgtgta tttttttttt ttcgcagttt cgctcttgtt gcccaggctg gagtgcaatg   20460
gcgcaatctc agctcactgc aacctctgtc tcctgggttc aagttattct cctgcctcag   20520
cctctcgagt agctgagatt acaggcatgc gcgaccacgc caggctaatt ttgtattttt   20580
agtagagacg ggtttctcc atgttggtca ggctggtctc aaactcctga cctcaggtga   20640
ttcacccgcc tcgacctccc aaactgctgg gattacaggc gtgagccacc acgcctggcc   20700
agctgttgtt ataactggag ttctatgtgc ttgtgaccat tcttggtttc tccgaatatc   20760
ctagaacttt ggtggcgccc tattatacag gttgttgaag aaatgttacc atgtggattg   20820
agtaggaaac aattctcttt atcttggcaa tattatggca tggcactact taaagtacaa   20880
attaaaagag ggggatgcta cagaactagc tgacaggcac tttgatagag gtggatttct   20940
cagttcttaa aatagctctt tataaaggaa gccagaggca ttgtggagga gaattcttac   21000
ataactcata gggttagacc acatccgacc ttttctgtgt ggcttcatgg ctctcttggt   21060
tgagaaagca ttagttttctc cttccattag tttcaacctc ttgatttctt gacccccta   21120 ctatattttg tgctgagaac acaagggtat aacaaccca cattgtagag gatcgctcag   21180
taataaagac tggagaataa aatgcagcat gggaatattg gcaattactc agttctaaat   21240
ttctcttgga aatgagggaa agcatacaga atagagctgg aatgaatagg ataatttttt   21300
ttttttttgc taagttggta gccagaatat aacagctccg cacaactgta aatgtccact   21360
cttcaatcca catgaagaaa agggtaaaaa tatggttgaa ctcaaccact agttgcccat   21420
tagaacagac tttcccagtg tactgcattt caatactttt tcttttatct cttttcagat   21480
cttcctcaga agaataggct tgttgtttta cagtgttagt gatccattcc ctttgacgat   21540
ccctaggtgg agatggggca tgaggatcct ccaggggaaa agctcactac cactgggcaa   21600 caacccagg tcaggaggtt ctgtcaagat actttcctgg tcccagatag gaagataaag   21660
tctcaaaaac aaccaccaca cgtcaaggtg cgtaagctgt ccctaaaagc ataataagta   21720
gtcttaattt tgattttgtt ttccagtata cattgcactt agtgtttcac tgaggtcgta   21780
ttcatcatta ttctgcatat gatttggtaa aaacagcttc ctaactaacc tgggaagcaa   21840
ctgggtgtga gattaactgg ttaaagtgat gatgtaaaga gggtagcggg ttgcatgtgt   21900
tcgggtgttt ggagtgggac tatagcacgt ggcagaggct tacagctaag ttgttctttt   21960
```

-continued

```
aggagaacat ggacaactgt cacatcagtg acattgatca catgggcaaa tcattctgtt    22020
ccatgtggtc cccaaagtct ctcttaaagc cttacagaag aactttgcca atcatttaca    22080
tacttcagga tggcttggga tgccatggtg tataatacaa caagtgagag gtgtgtcttt    22140
ttatgctatg gttgctgatt gatggaagcc gcataaatac aaatggaaac ctgactaaaa    22200
atggcacaaa gttatctgtc atcaggcagg agctaaagaa ccaggaccct acattctcta    22260
ggtcagtgtt gggagaggct gattagcgag tgagaattgg cagataaagg tgaccattcg    22320
gtgcaataaa tcctgaacgt ataggctttg cccagcattc ttcgtaaata gtgggtagct    22380
ataaatttca tgaaatattt tcatgggtaa gaactcttga aatgttataa ttgactagaa    22440
atctctgtag atttagaaat agagagttac taacaaattg ttagaaagtc taggaactag    22500
aaagctaagt tgagagttat ctaggaagat ctatctattg tactcataat ctttagataa    22560
attctcctag ggccagtagt ctatgtgaat tttcttttc ttcttcttct tcttctttt     22620 ttttgtattt tagctgcaat gttaaacaac ctatgtgaat tttcttattg tgagaatatt    22680
tgccttccag agtgactcac ctttatctca aagagcaata ttgtgagttt tgaaaatgct    22740
gctctaaggc tgtgttttgt tagtcctgag ccaggagact taaagcaaac ttgaggggtc    22800
ttaaaacatc gaagtgagcc ttaaacattg ggaagacctt atgttttcc ctctcatatc     22860 tattatttt gtgatctcag ttattaatca tttaaaggga ctctttccta gctgattggc     22920
acttaaaaca ggatggaagt ctttttttt ttttttttt ttgagatgga gttttgctct     22980
tgttgcccag gctggagtgc aatggtgcaa tctcagctca ctgcaacctc tgcctcccgg    23040
gttcaagcga ttctcctgcc tcagcctccc aagtagctgg gattacagtc atgcaccacc    23100
acgcccggct aattttgtat ttttaataga cggtgtttt ctccatgttg gtcaggctgg     23160
tctcaaactc ctgacctcag gtgatccgcc cacctcaacc tcccaaagtg ctgggattat    23220
gggcgtgagc caccgcgccc ggcagttctg gtctttaact aaggtataag gctatgactg    23280
gtagtggtgt ctcagtgac tcatcaagtg atatttggca agacattttc ccatttatgc     23340
cagtttccta ttctgttgaa tgaggaaatt ttctctctaa agacctaaaa gttttgactt    23400
tataggtttc aaagttctgt ggaaacattt tctattgctt attaatttga atcttatgta    23460
actctagcac agtactcaat atttatggca tttacatggt ttatctcatg ttttttata    23520 gctcttcatt gttcctatct gccaaatcat tatacttcct acaagcagtg cagagagctg    23580
agtcttcagc aggtccaaga aatttgaaca cactgaagga agtcagcctt cccacctgaa    23640
gatcaacatg cctggcactc tagcacttga ggatagctga atgaagtaag ttgttgatgt    23700
tgcagtcctg tgaggatcac ttcagaactg ttataacagc tgttttttgg gagctggtgt    23760
tggatggggt gtgttggtct aatgtgaagt ggggctaaat gtgagatgga aagatgacca    23820
gtcttccata ttactgactg ggttcactga agcaactcaa agacattatg gtcttcttac    23880
cagttgtatc acagaagaat ttagccttttg cttgtgtgtt ctatgtcttc actgtatagg    23940
ccctctgtca ttcttagagc cttaaacgtt gagaagctta aaacaccatt tctgctttct    24000
gctgaaaggg taacccttc tcatctccgt ttgtgagaga ctctgtcgtc agttaagatt     24060
agtgtaaaaa gaaaactaaa ctctgaagta gccattataa aagtgtgaga atgaagtcag    24120
ttttctaaag agttggggaa aggtgatgct aaaggagggg attgagcaag tcctatcaaa    24180 gagccttta tgaaaatact tagtcatctg tgacatccca tttggctctt ccagaaatcc     24240 tagtaaaatag ttgtaacagg atgttaagag gcatacattg tgtgttttaa atcctctgct    24300
actcattagg tatatgacct ttgacaactt aaagtctcta gacttctctg tttgtgaggg    24360
```

```
ttaaatgaaa tcatgtatgt aaagtgctca cctattgcag tgcctggcac atgtcaagta   24420
aaaggtaacc caagaagact cataagttca tttcccacaa tataagtgac cactagcact   24480
atcaggtagc aggcagagtt ggcatgcttt ggttctatgt aagaaatccc taaggtaaaa   24540
gtttataaat agaagagcat ctgtgttggt attggtggtt gttattattg tagtactata   24600
agtagtattc gtagtaacaa tagtttatta taattactaa tgacacttttt tgattttttt   24660 tatctttctg tgatgctttt catgcctctt gtgcccctca ctgtatcttg cctcttctac   24720
tacttacttc ctctgaatgt ctgcctttgc ttatctcttg cactcaagtg tgtatttctt   24780
tgtctctttc tttcttgtct ttgctctttg ttctctatct aaagtgtgtc ttacccattt   24840
ccatgtttct cttgctaatt tctttcgtgt gtgcctttgc ctcatttcct cttttgttc   24900 acaagagtgg tctgtgtctt gtcttagaca tatctctcat ttttcattt gttgctattt    24960 ctctttgctc tcctagatgt ggctcttctt tcacgcttta tttcatgtct ccttttggg    25020 tcacatgctg tgtgcttttt gtccttttct tgttctgtct acctctcctt tctctgccta   25080
cctctctttt ctctttgtga actgtgatta tttgttaccc cttcccttc tcgttcgttt    25140 taaatttcac cttttttctg agtctggcct ccttttctgct gtttctactt tttatctcac   25200
atttctcatt tctgcatttc ctttctgcct ctcttgggct attctctctc tcctcccctg   25260
cgtgcctcag catctcttgc tgtttgtgat tttctatttc agtattaatc tctgttggct   25320
tgtatttgtt ctctgcttct tcccttcta ctcacctttg agtatttcag cctcttcatg    25380
aatctatctc cctctctttg atttcatgta atctctcctt aaatatttct ttgcatatgt   25440
gggcaagtgt acgtgtgtgt gtgtcatgtg tggcagaggg gcttcctaac ccctgcctga   25500
taggtgcaga acgtcggcta tcagagcaag cattgtggag cggttcctta tgccaggctg   25560
ccatgtgaga tgatccaaga ccaaaacaag gccctagact gcagtaaaac ccagaactca   25620
agtagggcag aagtggaag gctcatatgg atagaaggcc caaagtataa gacagatggt     25680
ttgagacttg agacccgagg actaagatgg aaagcccatg ttccaagata gatagaagcc   25740
tcaggcctga aaccaacaaa agcctcaaga gccaagaaaa cagagggtgg cctgaattgg   25800
accgaaggcc tgagttggat ggaagtctca aggcttgagt tagaagtctt aagacctggg   25860
acaggacaca tggaaggcct aagaactgag acttgtgaca caaggccaac gacctaagat   25920
tagcccaggg ttgtagctgg aagacctaca acccaaggat ggaaggcccc tgtcacaaag   25980
cctacctaga tggatagagg acccaagcga aaaaggtatc tcaagactaa cggccggaat   26040
ctggaggccc atgacccaga acccaggaag gatagaagct tgaagacctg ggaaatccc    26100 aagatgagaa ccctaaaccc tacctctttt ctattgttta cacttcttac tcttagatat   26160
ttccagttct cctgtttatc tttaagcctg attcttttga gatgtacttt ttgatgttgc   26220
cggttacctt tagattgaca gtattatgcc tgggccagtc ttgagccagc tttaaatcac   26280
agcttttacc tatttgttag gctatagtgt tttgtaaact tctgtttcta ttcacatctt   26340
ctccacttga gagagacacc aaaatccagt cagtatctaa tctggctttt gttaacttcc   26400
ctcaggagca gacattcata taggtgatac tgtatttcag tccttttcttt tgaccccaga   26460 agccctagac tgagaagata aaatggtcag gttgttgggg aaaaaaagt gccaggctct    26520 ctagagaaaa atgtgaagag atgctccagg ccaatgagaa gaattagaca agaaatacac   26580
agatgtgcca gacttctgag aagcacctgc cagcaacagc ttccttcttt gagcttaggt   26640
gagcaggatt ctggggttttg ggatttctag tgatggttat ggaaagggtg actgtgcctg   26700
ggacaaagcg aggtcccaag gggacagcct gaactccctg ctcatagtag tggccaaata  26760
```

```
atttggtgga ctgtgccaac gctactcctg ggtttaatac ccatctctag gcttaaagat  26820
gagagaacct gggactgttg agcatgttta atactttcct tgatttttttt cttcctgttt  26880
atgtgggaag ttgatttaaa tgactgataa tgtgtatgaa agcactgtaa aacataagag  26940
aaaaaccaat tagtgtattg gcaatcatgc agttaacatt tgaaagtgca gtgtaaattg  27000
tgaagcatta tgtaaatcag gggtccacag ttttctgta agggtcaaa tcataaatac  27060
tttagactgt gggccatatg gtttctgtta catatttgtt ttttaaacaa cgttttata  27120
aggtcaaaat cattcttagt ttttgagcca attggatttg gcctgctgtt catagcttac  27180
caccccctga tgtattattt gttattcaga gaaaatttct gaatactact agtttccttt  27240
tctgtgcctg tccctgtgct aggcactaaa aatgcaatga ttattgatat ctaggtgacc  27300
tgaaaaaaaa tagtgaatgt gcttttgtaaa ctgtaaagca cttgtattct actgtgataa  27360
gcgttgtgga tacaaagaaa ggagcaagca taaaaaagtg ctctttcaaa aggatatagt  27420
actatgcaga cacaaggaat tgtttgataa atgaataaat tatatgtata tttgaggcca  27480
atttgtgttt gctgctctgg taattttgag taaaaatgca gtattccagg tatcagaaac  27540
gaaaacacat ggaaactgct tttaaacttt aaaatatact gaaaacataa gggactaagc  27600
ttgttgtggt cacctataat gtgccagata ccatgctggg tgctagagct accaaggggg  27660
gaaaagtatt ctcatagaac aaaaaatttc agaaaggtgc atattaaagt gctttgtaaa  27720
ctaaagcatg atacaaatgt caatgggcta catatttatg aatgaatgaa tggatgaatg  27780
aatattaagt gcctcttaca taccagctat tttgggtact gtaaaataca agattaattc  27840
tcctatgtaa taagaggaaa gtttatcctc tatactattc agatgtaagg aatgatatat  27900
tgcttaattt taaacaatca agactttact ggtgaggtta agttaaatta ttactgatac  27960
atttttccag gtaaccagga aagagctagt atgaggaaat gaagtaatag atgtgagatc  28020
cagaccgaaa gtcacttaat tcagcttgcg aatgtgcttt ctaaattata aagcacttgt  28080
aaatgaaaaa tttgatgctt tctgtatgaa taaaactttc tgtaagctag gtattgtctc  28140
tacaaaattc tcattgtata gttaaaccac agtgagaagg gttctataag tagttataca  28200
aaccaagggt ttaaatacct gttaaataga tcaattttga ttgcctacta tgtgaactca  28260
ctgttaaagg cactgaaaat ttatcatatt tcatttagcc acagccaaaa ataaggcaat  28320
acctatgtta gcattttgtg aactctaagg caccatataa atgtaactgt tgattttctc  28380
acttggtgct gggtactagg tttataaaat tgtatgatag ttattatatt gtgcaaataa  28440
agtaggaaaa tttgaataac aatgattatc ttttgaatac gcatacgcaa gggattggtt  28500
gtctgaagaa tgccactata gtagttatct attgtgtgcc aatctcattg ctaggcattg  28560
gggatgcaaa gataaaccat ctttattgtg tcttgggtag cagaagaaaa tatgtgtaaa  28620
atcaatttat aatttgtaaa ctgccaccca tatataagct atatctgctg aatgatcatt  28680
gattactctt atccttagag ataacaactg ggggcacaaa catttattat cattattgaa  28740
cctacaacag agatctatgt gtagatttac aaagcctaca gttctataca gataggaatg  28800
aactattggc ttactgaatg gtgattactt tctgtggggc tcggaactac atgccctagg  28860
atataaaaat gatgttatca ttatagagtg ctcacagaag gaaatgaagt aatataggtg  28920
tgagatccag accaaaagtc atttaacaag tttattcagt gatgaaaaca tgggacaaat  28980
ggactaatat aaggcagtgt actaagctga gtagagagat aaagtcctgt ccagaagata  29040
catgcttcct ggcctgattg aggagatgga aaatttttgc aaaaaacaag gtgttgtggt  29100
cttccatcca gtttcttaag tgctgatgat aaaagtgaat tagacccacc ttgacctggc  29160
```

```
ctacagaagt aaaggagtaa aaataaatgc ctcaggcgtg cttttttgatt catttgataa   29220 acaaagcatc ttttatgtgg aatataccat tctgggtcct gaggataaga gagatgaggg   29280
cattagatca ctgacagctg aagatagaag aacatctttg gtttgattgt ttaaataata   29340
tttcaatgcc tattctctgc aaggtactat gtttcgtaaa ttaaataggt ctggcccaga   29400
agacccactc aattgccttt gagattaaaa aaaaaaaaa aagaaagaa aaatgcaagt    29460 ttctttcaaa ataaagagac attttttccta gtttcaggaa tcccccaaat cacttcctca   29520
ttggcttagt ttaaagccag gagactgata aagggctca gggtttgttc tttaattcat     29580
taactaaaca ttctgctttt attacagtta aatggttcaa gatgtaacaa ctagttttaa   29640
aggtatttgc tcattggtct ggcttagaga caggaagaca tatgagcaat aaaaaaaga   29700 ttcttttgca tttaccaatt tagtaaaaat ttattaaaac tgaataaagt gctgttctta   29760
agtgcttgaa agacgtaaac caaagtgcac tttatctcat ttatcttatg gtggaaacac  29820
aggaacaaat tctctaagag actgtgtttc tttagttgag aagaaacttc attgagtagc  29880
tgtgatatgt tcgatactaa ggaaaaacta aacagatcac ctttgacatg cgttgtagag  29940
tgggaataag agagggcttt ttatttttttc gttcatacga gtattgatga agatgatact  30000
aaatgctaaa tgaaatatat ctgctccaaa aggcatttat tctgacttgg agatgcaaca  30060
aaaacacaaa aatggaatga agtgatactc ttcatcaaac agaagtgact gttatctcaa  30120
ccattttgtt aaatcctaaa cagaaaacaa aaaaaatcat gacgaaaaga cacttgctta   30180
ttaattggct tggaaagtag aatataggag aaaggttact gttttatttttt tttcatgtat  30240 tcattcattc tacaaatata ttcgggtgcc aataggtact tggtataagg ttttttggccc  30300 cagagacatg ggaaaaaaat gcatgccttc ccagagaatg cctaatactt tcctttttggc  30360 ttgttttctt gttaggggca tggcttagtc cctaaataac attgtgtggt ttaattccta   30420
ctccgtatct cttctaccac tctgccact acgataagca ggtagctggg ttttgtagtg    30480
agcttgctcc ttaagttaca ggaactctcc ttataataga cacttcattt tcctagtcca    30540
tccctcatga aaaatgactg accactgctg ggcagcagga gggatgatga ccaactaatt   30600
cccaaacccc agtctcattg gtaccagcct tggggaacca cctacacttg agccacaatt   30660
ggttttgaag tgcatttaca aggtttgtct attttcagtt cttttacttttt tacatgctga    30720 cacatacata cactgcctaa atagatctct ttcagaaaca atcctcagat aacgcatagc   30780
aaaatggaga tggagacatg atttctcatg caacagcttc tctaattata ccttagaaat   30840
gttctccttt ttatcatcaa atctgctcaa gaagggcttt ttatagtaga ataatatcag  30900
tggatgaaaa cagcttaaca ttttaccatg cttaagtttt aagaataaaa taaaaattgg   30960
aaataattgg ccaaaattga aaggaaaaat ttttttaaaa tttctctaaa tgtaggcctg   31020
gctgggcttt gaccttttcc gttttttaaat cactcacaga gggtgggaca ggaggaagag  31080
tgaaggaaaa ggtcaaacct gttttaaggg caacctgcct ttgttctgaa ttggtcttaa    31140
gaacattacc agctccaggt ttaaattgtt cagtttcatg cagttccaat agctgatcat    31200
tgttgagatg aggacaaaat cctttgtcct cactagtttg ctttacattt ttgaaaagta   31260 ttattttttgt ccaagtgctt atcaactaaa ccttgtgtta ggtaagaatg gaatttatta   31320
agtgaatcag tgtgacccctt cttgtcataa gattatctta aagctgaagc caaaatatgc   31380
ttcaaaagaa gaggacttta ttgttcattg tagttcatac attcaaagca tctgaactgt   31440
agtttctata gcaagccaat tacatccata agtggagaag gaaatagata aatgtcaaag   31500
tatgattggt ggaggggagca aggttgaaga taatctgggg ttgaaatttt ctagttttca   31560
```

```
ttctgtacat ttttagttag acatcagatt tgaaatatta atgtttacct ttcaatgtgt   31620
ggtatcagct ggactcagta acacccctttt cttcagctgg ggatggggaa tggattattg  31680
gaaaatggaa agaagaaagt aactaaaagc cttcctttca cagtttctgg catcactacc   31740
actactgatt aaacaagaat aagagaacat tttatcatca tctgctttat tcacataaat   31800
gaagttgtga tgaataaatc tgcttttatg cagacacaag gaattaagtg gcttcgtcat   31860
tgtccttcta cctcaaagat aatttattcc aaaagctaag ataaatggaa gactcttgaa   31920
cttgtgaact gatgtgaaat gcagaatctc ttttgagtct ttgctgtttg gaagattgaa   31980
aaatattgtt cagcatgggt gaccaccaga aagtaatctt aagccatcta gatgtcacaa   32040
ttgaaacaaa ctggggagtt ggttgctatt gtaaaataaa atatactgtt ttga         32094
```

NUCLEIC ACID SILENCING SEQUENCES

CROSS-REFERENCE TO RELATED APPLICATIONS

This application is a continuation of U.S. application Ser. No. 12/512,964, filed on Jul. 30, 2009, now U.S. Pat. No. 8,212,019, which claims the benefit of the filing date of U.S. Application No. 61/084,918, filed on Jul. 30, 2008, each of which is incorporated herein by reference in its entirety.

STATEMENT REGARDING FEDERALLY SPONSORED RESEARCH OR DEVELOPMENT

This invention was made with government support awarded by the National Institutes of Health under Grant Nos. GM053234, GM068138 and HD007439. The U.S. Government has certain rights in this invention.

TECHNICAL FIELD

This invention relates to compositions and methods for silencing gene expression from a whole chromosome or chromosome segment, and more particularly to the use of an Xist gene or other chromosomal silencing RNA to silence expression from trisomic, translocated, duplicated, or partially duplicated genomic sequences.

BACKGROUND

Naturally occurring chromosomal imbalances are an exceptionally important clinical problem, in part because they are extremely common. Almost 1% of all live births and a much higher percentage of conceptions are affected. Many of the abnormalities involve "extra" chromosomal material, and many of these are so deleterious that they cause spontaneous abortion. Trisomies, in which the fetus carries three of a given chromosome rather than a pair, are usually lethal. Some are not; trisomy 13 (Patau syndrome), trisomy 18 (Edward syndrome), trisomy 21 (Down syndrome), triple-X syndrome, as well as duplications of the X and Y chromosomes (e.g., XXY and XYY) are seen in live births, although babies born with Patau syndrome or Edward syndrome usually do not live more than a year or two.

Down syndrome is extremely common relative to other severe genetic disorders. In the United States alone, over 350,000 people are living with the severe handicaps typical of Down syndrome, and there are millions of affected people around the world. Although Down syndrome children are often happy and highly loved, their disorder greatly impacts them, their entire families, and society. Mental retardation, with poor verbal functioning, is the most debilitating outcome, but there are also other medical issues, including much greater risks of early onset Alzheimer's disease, leukemia, and cardiac defects. Because Down syndrome individuals often are at or just below the threshold of independent functioning, even small increases in function could have significant positive consequences for them and their families.

Although the incidence of Down syndrome increases with the mother's age, 80% of Down syndrome babies are born to women under 35 who are not currently subject to prenatal screening. Upon birth of the Down syndrome baby, the whole family is faced with the enormous challenges associated with caring for and nurturing such a child. For older mothers who do have pre-natal screening, the parents are faced with the heart-wrenching decision of birthing a mentally retarded child or terminating the pregnancy, with no hope of systemic therapy. We believe that whole chromosome therapy would result in a paradigm shift in the minds of many scientists, families, and clinicians, who currently presume that gene therapy for this multi-gene disorder, with such pleiotropic effects, is just not possible.

SUMMARY

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker. Below, we may refer to the first and second sequences that direct insertion of the silencing sequence into a targeted chromosome as "first and second targeting elements." These sequences or elements can be readily selected and inserted into the nucleic acid constructs using methods well known in the art.

In the present application, we use the term "Xist" to refer to an Xist gene or the encoded Xist RNA regardless of the origin of the sequence. For example, the present compositions can include, and the present methods can be carried out with, an Xist gene encoding an Xist RNA from humans or another mammal (e.g., a rodent such as a mouse, dog, cat, cow, horse, sheep, goat, or another mammalian or non-mammalian animal). We mention this as the scientific literature has adopted a loose convention whereby the term is fully capitalized (XIST) when referring to a human sequence but not fully capitalized (Xist) when referring to the murine sequence. That convention is not used here, and we wish to make clear that human and non-human sequences may be used as described herein.

The "silencing sequence" is a nucleotide sequence that encodes an RNA that silences a chromosome or a segment or region thereof. While the invention is not limited to the use of silencing sequences that work by any particular molecular mechanism, silencing sequences are believed to encode RNA that binds across the chromosome or chromosome segment and induces repressive changes to chromatin that silence gene expression at the level of transcription. The silencing sequence can include, but is not limited to, a naturally occurring DNA sequence, and "silencing" is a term of art that is understood to refer to a significant reduction in the level of transcription of a gene within the silenced or targeted region of a chromosome.

The silencing sequence can be a full-length Xist gene sequence, a sequence encoding another full-length silencing RNA (examples of which are provided below), or any biologically active fragment or other biologically active variant thereof. The sequence is "biologically active" where its activity is sufficient to effect a therapeutically beneficial outcome. The level of activity of a biologically active fragment or other variant may vary so long as a useful chromosomal silencing RNA is produced. Xist RNA is referred to as a chromosomal silencing RNA because it silences by binding across the chromosome or chromosome segment, and therefore silences at the level of transcription, by inducing repressive changes to chromatin. While Xist RNA is a well studied example of a chromosomal silencing RNA, other non-coding RNAs can silence specific clusters of imprinted genes or segments of a chromosome. These other chromosomal silencing RNAs include Air RNA, HOTAIR RNA, and Kcnq1ot1 RNA (see Goodrich and Kugel, *Crit. Rev. Biochem. and Mol. Biol.* 44:3-15, 2009), any of which can be formulated and used as described herein for Xist. Other intergenic noncoding RNAs, which may be useful in the present nucleic acid constructs and the silencing methods described herein are described by Khalil et al. (*Proc. Natl. Acad. Sci. USA* 106:11675-11680, 2009).

The silencing sequence can exclude one or more introns (wholly or partially) or one or more exons (wholly or partially). However, the silencing sequence cannot exclude all exons. For example, the silencing sequence can be an Xist gene sequence exclusive of one or more introns or one or more exons (but not all exons). For example, the silencing sequence can include about 6 kb to about 10 kb of exon 1 of an Xist gene sequence (e.g., about 6-7 kb, 7-8 kb, 8-9 kb, 6.5-8.5 kb, or about 7.5 kb). More specifically, the silencing sequence can be or can include the Xist cDNA sequence having accession number M97168 or a biologically active fragment or other variant thereof (SEQ ID NO:1).

The silencing sequence can be a mammalian sequence (e.g., a human sequence) and can further include a regulatory sequence (e.g., a regulatory sequence that promotes expression of the Xist RNA). More specifically, the regulatory sequence can include a promoter, which may be constitutively active, inducible, tissue-specific, or a developmental stage-specific promoter. Enhancers and polyadenylation sequences can also be included.

The targeted chromosome can be any autosome or an X or Y chromosome. For example, the targeted chromosome can be chromosome 13, chromosome 18, or chromosome 21. The targeted chromosome can be the third chromosome within a trisomic cell or any region of a chromosome that is aberrant (e.g., a gene or genetic sequence that is duplicated, partially duplicated and/or translocated).

Numerous selectable markers can be incorporated in the nucleic acid constructs. These markers are discussed further below and many such markers will be known to one of ordinary skill in the art. Sequences including a selectable marker can, for example, upon transcription and translation, confer resistance to a toxin or encode proteins that produce an observable characteristic. Thus, expression of the selectable marker sequence allows one to distinguish or "select" genetically modified cells from non-modified cells.

Numerous vectors are also known in the art, and any vector (including viral and non-viral vectors) can be used to deliver the present nucleic acids to a patient or a cell in culture. Accordingly, the invention features vectors and isolated or cultured cells that include any of the nucleic acid constructs described herein.

In another embodiment, the invention features compositions (e.g., pharmaceutically acceptable compositions) that include the nucleic acid constructs or vectors described above (and elsewhere herein) and, alternatively or in addition, a vector that facilitates delivery of the transgene to a cell and/or incorporation of the transgene into the targeted chromosome. Thus, the invention encompasses pharmaceutically acceptable compositions that include nucleic acid constructs carrying a transgene (e.g., a silencing sequence), first and second sequences that direct insertion of the silencing sequence into a targeted chromosome and, optionally, a selectable marker. The targeted integration may be facilitated by inclusion in the construct of sequences homologous to the site of desired chromosomal integration (i.e., the first and second sequences or targeting elements), coupled with the transgene (e.g., sequence encoding Xist RNA or other chromatin-associated silencing RNA).

As noted, the invention features compositions that also include vectors that facilitate delivery of the transgene. Well established targeting methods that rely on homologous recombination can be made more efficient by use of zinc finger nucleases to direct integration at specific sites. Thus, the present compositions can include a cleavage vector comprising a sequence encoding a first chimeric zinc finger nuclease (ZFN) or an adeno associated virus, which can specifically integrate the transgene and deliver it to cells. We describe the ZFNs as "chimeric" as they include at least one zinc finger DNA binding domain effectively linked to at least one nuclease capable of cleaving DNA. Ordinarily, cleavage by a ZFN at a target locus results in a double stranded break (DSB) at that locus.

Various combinations of the constructs and vectors described herein can also be formulated as pharmaceutical compositions. For example, the present compositions can include an adeno associated virus into which a silencing sequence has been inserted or a combination of (a) a nucleic acid construct or vector that silences a targeted chromosomal region or induces cell death following targeted chromosomal integration and (b) a cleavage vector encoding a chimeric ZFN.

The cleavage vector can include more than one chimeric ZFN, any of which can include a DNA binding domain and a cleavage domain. The DNA binding domain binds a genomic sequence that is present in each of the two strands of the targeted chromosome such that the cleavage domain generates a double stranded break in the targeted chromosome at a site into which the first and second sequences will direct insertion of the silencing sequence.

The same cleavage vector that encodes a first chimeric ZFN can include one or more additional sequences encoding one or more additional chimeric ZFNs (e.g., two, three, four, or more ZFNs). Alternatively, additional chimeric ZFNs can be carried on a separate vector. The second and any subsequent chimeric ZFNs can include a DNA binding domain and a cleavage domain. The first chimeric ZFN and the second chimeric ZFN bind, respectively, to distinct sequences in each of the two strands of the targeted chromosome such that the respective cleavage domains generate a double stranded break in the targeted chromosome at a site into which the first and second sequences within the nucleic acid construct will direct insertion of the silencing sequence (or other sequence (e.g., a sequence that causes cell death)). As when the nucleic acid constructs or vectors, including adeno associated vectors, are used alone, the ZFNs can target an autosome. For example, ZFNs can target chromosome 13, chromosome 18, or chromosome 21.

Also within the scope of the invention are RNAs and proteins encoded by the cleavage vector and compositions that include them (e.g., lyophilized preparations or solutions, including pharmaceutically acceptable solutions or other pharmaceutical formulations).

In another embodiment, the invention features cells that include the nucleic acid constructs, vectors (e.g., an adeno associated vector), and compositions described herein. The cell can be isolated in the sense that it can be a cell within an environment other than that in which it normally resides (e.g., the cell can be one that is removed from the organism in which it originated). The cell can be a germ cell, a stem cell (e.g., an embryonic stem cell, an adult stem cell, or an induced pluripotent stem cell (iPS cell or IPSC)), or a precursor cell. Where adult stem cells are used, the cell can be a hematopoietic stem cell, a cardiac muscle stem cell, a mesenchymal stem cell, or a neural stem cell. The cell can also be a differentiated cell (e.g., a fibroblast or neuron).

The methods of the invention can be used to treat patients who have a birth defect, genetic disease, or cancer associated with a genetic aberration (e.g., a trisomy, partial duplication of a chromosomal region, translocation, or ring X-chromosome). Any of the methods can include the step of identifying a patient in need of treatment; any of the patients can be human; and any of the methods can be carried out by either administering the present compositions to the patient or removing cells from the patient, treating the cells, and "readministering" those cells. For example, the invention features methods of treating a genetic disorder associated with a trisomic chromosome by identifying a patient in need of treatment; and administering to the patient a nucleic acid construct, vector, and/or cleavage vector as described herein. The targeted chromosome can be the trisomic chromosome, and the amount of the construct or vector administered will be an amount sufficient to improve a condition associated with the disorder. Where cells are harvested from a patient to treat a condition or disorder described herein (or an associated symptom), the methods can include the steps of identifying a patient in need of treatment; harvesting cells from the patient; transfecting the cells with one or more of the types of constructs and/or vectors described herein; and administering to the patient a sufficient number of the transfected cells to treat the condition or improve a condition or symptom associated with the disorder. The symptoms associated with many birth defects and other conditions are well known. For example, individuals having Down Syndrome often experience mental retardation, hypotonia, cardiac defects, Alzheimer's Disease, hematological abnormalities and leukemia (see Antonarakis and Epstein, *Trends Mol. Med.* 12:473-479, 2006). As noted above, treatment can also be carried out in vivo by administering present compositions to the patient via pharmaceutically acceptable compositions.

The cells can include differentiated cells (e.g., white blood cells or fibroblasts) and/or undifferentiated cells (e.g., stem cells or precursor cells). The cells can also be differentiated cells that are induced, ex vivo, into iPS cells, or multi-potent stem cells or stem cells of particular lineage, such as neural stem cells. The condition can be a neurological or blood disorder such as Alzheimer's Disease and leukemia, respectively, or a muscular defect, including defects of the heart. Where the condition is myelodysplastic disease which leads to leukemia, it can be an acute lymphocytic leukemia, an acute myelogenous leukemia, or an acute megakaryoblastic leukemia.

In any of the present methods, cells can be transfected with a cleavage vector that includes a sequence encoding a first chimeric zinc finger nuclease (ZFN) having a DNA binding domain and a cleavage domain. As in other embodiments, the DNA binding domain binds a genomic sequence that is present in each of the two strands of the targeted chromosome such that the cleavage domain generates a double stranded break in the targeted chromosome at a site into which the first and second sequences will direct insertion of the silencing sequence or other therapeutically useful sequence (e.g., a toxin or pro-apoptotic protein). Where desirable, the transgene (e.g., a silencing sequence encoding an Xist RNA) can be targeted to a polymorphic sequence that is present in just one chromosome (e.g., one of a set of trisomic chromosomes). Additionally, integration of the Xist transgene can be targeted so as to directly disrupt a particularly deleterious gene, such as the APP gene, over-expression of which leads to the exceptionally high rate and early onset of Alzheimer's Disease among Down Syndrome individuals.

The invention also includes compositions and methods for the silencing of a duplicated genomic region or trisomic chromosome using an approach of random transgene integration followed by cell selection, where the silencing of the trisomic chromosomal material provides a significant selective advantage as compared to silencing of other disomic chromosomes. As a result, patient cells in which the deleterious extra chromosomal material has been silenced by a large non-coding RNA may have a selective advantage; thus, even where Xist transgenes have been inserted at random into the genome of patient cells, cells in which the trisomic chromosome has been silenced may be selected for over those cells in which a disomic chromosome has been silenced (since the latter would generate a functional monosomy that is likely lethal to the cell). In the case of translocated chromosomes, targeting of the transgene can be directed to the unique site generated at the translocation junction, to selectively silence that abnormal chromosome, or to introduce a sequence encoding a toxin, pro-apoptotic protein, or other factor that results in cell death of deleterious cells. For example, using the present methods, one can introduce a sequence encoding a toxin, pro-apoptotic protein, or other factor that results in cell death into a translocated chromosome associated with cancer. This approach can be extended to silencing of duplicated regions of specific chromosomes that are associated with genetic conditions, such as duplication of segments of Chromosome 15q11-13 in Autism. This duplication, which is thought to be the most frequent cytogenetic abnormality in autism, can be targeted by the present methods and is described further in Nakatani et al. (*Cell* 137:1236-1246, 2009). This approach can also be extended to silencing the inappropriate expression of imprinted regions in genetic disease, as in Prader-Willi/Angelman syndrome, also on Chr 15 and associated with autism.

To illustrate a particular application, Xist mediated chromosomal therapy could be used to ameliorate transient myeloproliferative disorder (TMD) in Down Syndrome children and possibly prevent the later development of acute leukemia. Successful bone marrow transplants for diseases like leukemia depend upon immune compatibility, to avoid Graft versus Host Disease (GVHD). To avoid graft rejection, the patient's own cells can be used and transgenically modified prior to transplant. There are two scenarios to acquire and modify stem cells for bone marrow transplant. In the first, the patient's own bone marrow stem cells can be obtained and an Xist transgene can be introduced and targeted to chromosome 21. When Xist expression silences the trisomic chromosome, these cells can then be transplanted back into the patient following standard bone transplant procedures following the destruction of the patient's bone marrow using irritation. Alternatively modified patient bone marrow cells can be transplanted without first irradiating the patient to destroy the unmodified bone marrow. This would produce a situation where the patient's bone marrow would be mosaic for trisomy 21 (a mixture of modified and unmodified cells). We expect that the modified cells would have a growth advantage over the non-modified fully trisomic cells, and the modified cells would eventually out grow the "diseased" cells (see Douillard-Guilloux et al., *J. Gene Med.* 11:279-287, 2009). In the second approach, the patient's fibroblast (skin) cells can be used to produce iPS cells, into which a transgenic Xist gene is inserted and targeted to chromosome 21. IPS cells that silence one of the three trisomic chromosomes will then be differentiated into adult hemopoietic stem cells and introduced back into the patient as stated above.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Figure 6A:
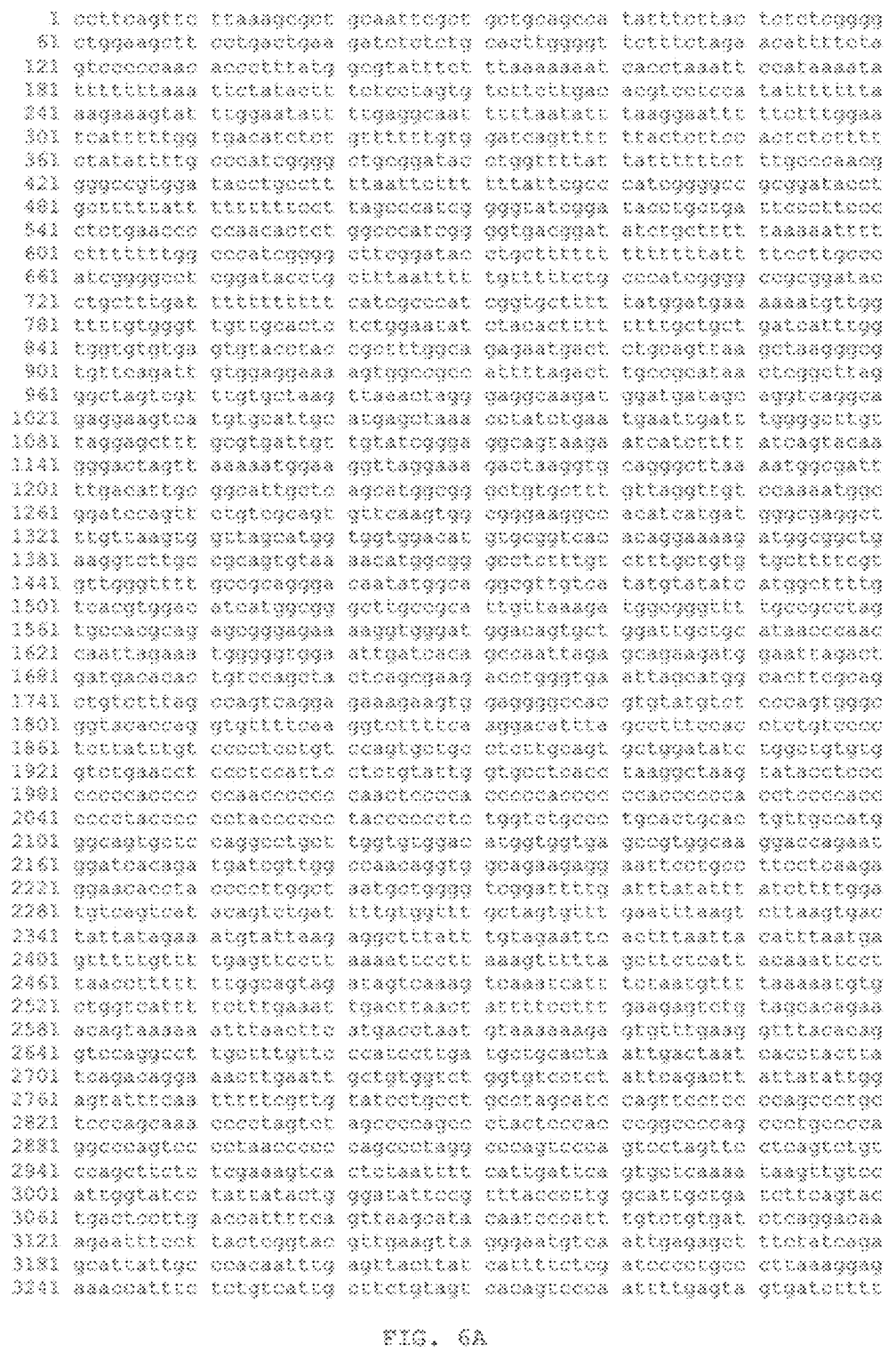

FIGS. 6A-E are a series of five contiguous panels showing the complete exon sequence of the *Homo sapiens* X (inactive)-specific transcript (Xist), GenBank Accenssion No. M97168.1, SEQ ID NO:1.

FIGS. 7A-J are a series of 10 contiguous panels showing the *Homo sapiens* DNA sequence from clone RP13-216E22 on chromosome Xq13.1-21.1 with the X (inactive)-specific transcript (non-protein coding) (Xist), non-coding RNA, GenBank Accenssion No. AL353804.22, SEQ ID NO:2.

DETAILED DESCRIPTION

Down Syndrome, caused by trisomy of chromosome 21, is the leading cause of mental retardation in newborns, impacting one in every 600-700 live births in the U.S. and across the world. Many families with Down Syndrome children find them loving, happy children, but they are challenged with mild to moderate mental retardation and frequently have a number of medical conditions requiring treatment or surgery. Despite the enormous clinical importance of Down Syndrome and related chromosomal imbalances, there has been little hope or effort for gene therapy in Down Syndrome. Historically, devising therapeutic strategies for trisomies has been particularly challenging because more is involved than a single defective gene or even several defective genes. Down syndrome, for example, involves a quantitative imbalance in tens or hundreds of genes across a 50 Mb chromosome, the most important of which are still not yet well understood (Antonarakis and Epstein, *Trends Mol. Med.* 12:473-479, 2006). Thus, unlike other genetic diseases in which silencing of an individual gene might produce an effective therapy, genetic therapy for trisomies such as Down syndrome is much more challenging. This is because chromosomal trisomies (and segmental duplications or translocations) involve the over-expression of potentially hundreds of genes across a ~50 Mb or larger chromosome, rendering ineffective standard approaches to gene therapy which treat single gene defects.

This invention makes possible an approach to "chromosome therapy" for trisomies or segmental duplications by reducing the challenge of individually correcting over-expression of tens or hundreds of genes, to the much more tractable approach of introducing just one gene, for example Xist, which then silences the whole chromosome.

Figure 1:
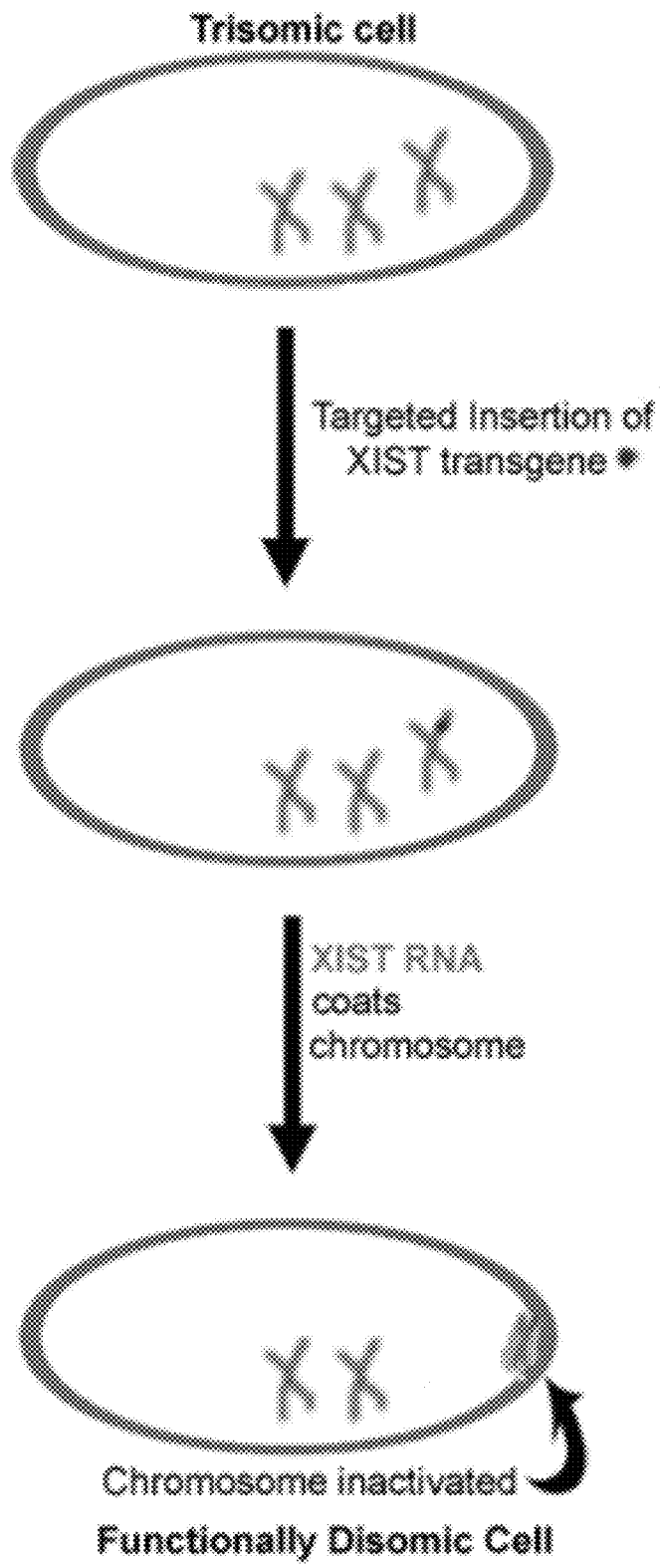
FIG. 1 is a schematic diagram illustrating the process of chromosomal inactivation. Three chromosomes are shown in the cell initially. Following targeted insertion of an Xist transgene, Xist RNA exerts its effect on chromosomal sequences that are cis to the Xist transgene, resulting in inactivation of one chromosome and a functionally disomic cell.
Figure 2:
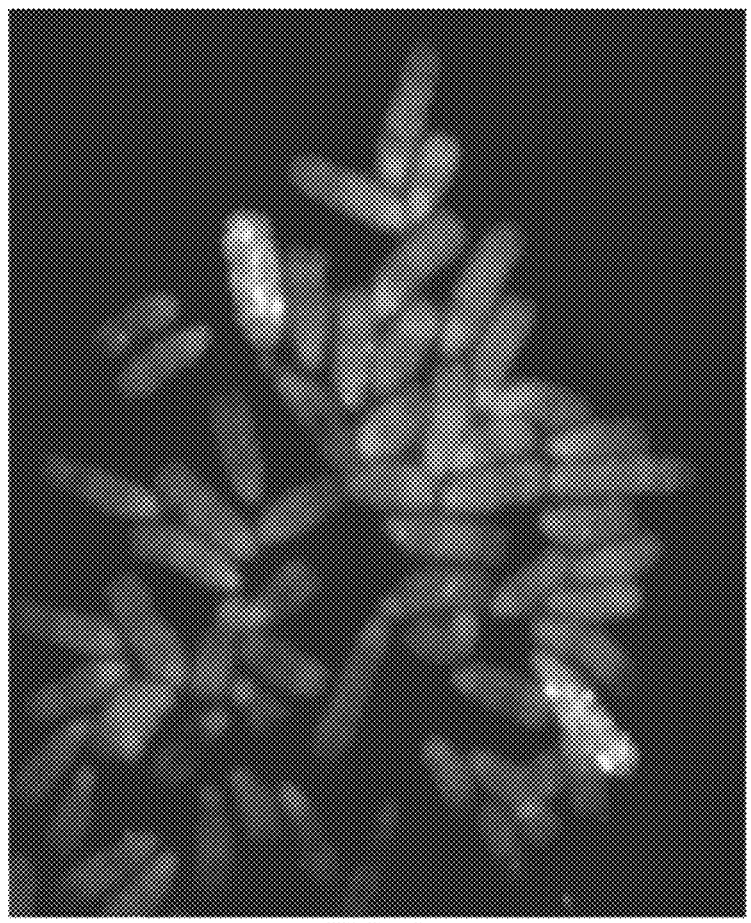
FIG. 2 is an image of chromosomes from an XXX mouse cell showing that Xist RNA (green in color and brighter in black-and-white) coats two X-chromosomes and inactivates both.
Figure 3:
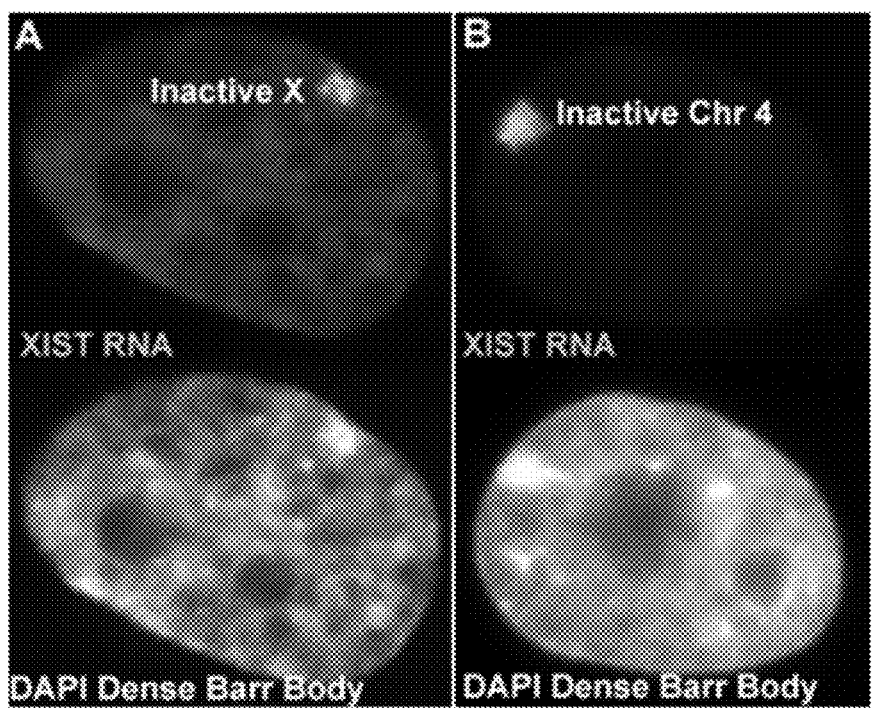
FIG. 3A is a photograph showing Xist RNA localized to an inactive X chromosome in a cell (upper photograph) and the corresponding DAPI dense Barr Body in the same cell (lower photograph).
FIG. 3B is a photograph showing Xist RNA localized to an inactive human Chr 4 carrying a transgenic Xist gene (upper photograph) and the lower panel shows the corresponding DAPI dense Barr Body in the same cell (lower photograph). Inactivation of the autosome occurred in an adult somatic cell (derived from a fibrosarcoma).

We set out to develop an innovative approach to chromosome therapy that would translate the system nature devised to dosage compensate the X chromosome in females. Nature assures proper "gene dosage" of X-linked genes between females (XX) and males (XY) via the Xist gene, which produces a large, non-coding RNA (Brown et al., *Cell,* 71:527-542, 1992; Clemson et al., *J. Cell Biol.* 132:259-275, 1996) that is expressed from and accumulates exclusively on the inactive X chromosome (Xi), "painting" the whole structure of the interphase chromosome territory (reviewed in Hall and Lawrence, *Semin. Cell Dev. Biol.* 14:369-378, 2003). Brown et al. discloses the cDNA sequence of Xist, which can be used in the design and construction of the nucleic acid constructs described herein. FIG. 2 shows mouse Xist RNA on two mitotic X chromosomes in a cell with X trisomy. Nature has also devised a counting mechanism such that all but one X chromosome is silenced (thus trisomy X has essentially normal gene dosage and is viable). Once Xist RNA coats the chromosome, a series of chromatin modifications occurs which are key hallmarks of the inactive X, including histone H3K27 methylation, H2A ubiquitination, macroH2A, and hypoacetylation of histone H4 (e.g., FIG. 5). Importantly, although Xist RNA is essential to initially enact this silencing process, once formed, the heterochromatic chromosome remains largely inactivated, even if Xist expression is later experimentally silenced (reviewed in Hall and Lawrence, *Semin. Cell Dev. Biol.* 14:369-378, 2003).

The new system would result in the silencing of additional or duplicated material (e.g., trisomies or segmental duplications) or translocated genomic material (e.g., the translocation of chromosomal arms that sometimes gives rise to birth defects or the translocations seen in certain cancers). The silencing would not be targeted to an intact X chromosome but could be targeted to an abnormal X chromosome lacking the Xist gene.

Where the intention is to "turn off" an extra chromosome, one can incorporate a silencing sequence using the compositions and methods described herein. The silencing sequence (e.g., an Xist gene of a human or other mammal such as a mouse or another silencing sequence described herein) is targeted to the region to be silenced (e.g., to the trisomic chromosome).

In another embodiment, where the intention is to kill a genetically aberrant cell (e.g., a cell in which a cancer-related translocation has occurred), one can incorporate a silencing sequence at the unique site of the translocation using the compositions and methods described herein. Silencing of the translocation would create a functional monosomy for the involved autosomal material which, depending on the chromosomal region silenced and the extent of the chromosomal region silenced would induce cell death or impede cell proliferation. In addition to incorporating a silencing sequence or as an alternative to incorporating a silencing sequence, one can use the present nucleic acid constructs and methods to target a "cell death" gene to the site of the translocation. For example, the nucleic acid construct can include an Xist gene and/or a gene encoding a toxin or pro-apoptotic factor. The toxins that can be expressed may include Shiga toxins 1 and 2 (Stx1 and Stx2); botulinum toxin from *Clostridium botulinum*; a virulence factor produced by *Bacillus anthracis* (e.g., a tripartite exotoxin referred to as anthrax toxin); a *Vibrio cholerae* multifunctional-autoprocessing RTX toxin; pertussis toxin from *Bordetella pertussis*; VacA from *Helicobacter pylori*: diphtheria exotoxin from *Corynebacterium diphtheriae; ricinus communis; pasteurella multocida* toxin (PMT); β-toxin-like peptide (named BmKBT) and two MkTx I homologues (named MkTx II and MkTx III), from a venom gland cDNA library of the Chinese scorpion *Buthus martensii* Karsch; haemorrhagic toxin acutolysin A from *Agkistrodon acutus: Bacillus thuringiensis* (Bt) toxin Cry1A and Cry1A (b); and Type A *Clostridium perfringens* cpb2. The pro-apoptotic proteins that can be expressed include, for example, Bcl-2-associated X protein (BAX), BH3 interacting domain death agonist (BID), Bcl-2 homologous antagonist killer (BAK), and Bcl-2-associated death promoter (BAD).

As noted, the translocation or duplication may be associated with a birth defect or may be a translocation associated with a cancer. The targeted chromosomal regions are then regions at or near the site of the translocation or duplication. These sites can be determined through genetic and sequence analysis, and several examples are known in the art. For example, one can target the following known sites of translocations: t(2;5)(p23;q35), which is associated with anaplastic large cell lymphoma; t(8;14), which is associated with Burkitt's lymphoma (c-myc); t(9;22)(q34;q11)/Philadelphia chromosome, which is associated with CML and ALL; t(11;14), which is associated with Mantle cell lymphoma (Bcl-1); t(11;22)(q24;q11.2-12), which is associated with Ewing's sarcoma; t(14;18)(q32;q21), which is associated with follicular lymphoma (Bcl-2); t(17;22), which is associated with dermatofibrosarcoma protuberans; t(15;17), which is associated with acute promyelocytic leukemia; t(1;12)(q21;p13), which is associated with acute myelogenous leukemia; t(9;12)(p24;p13), which is associated with CML and ALL (TEL-JAK2); t(X;18)(p11.2;q11.2), which is associated with synovial sarcomas; t(12;15)(p13;q25)-(TEL-TrkC), which is associated with acute myeloid leukemia, congenital fibrosarcoma, and secretory breast carcinoma.

Where the transgene is delivered to the patient, it will be useful to use a delivery system such as adeno associated virus, which also has the potential for site-specific integration.

Thus, the strategies described herein are applicable to trisomies, translocations, or any partial duplication of genomic DNA or aberration. For example, the present compositions and methods can be used to silence fragment or ring X-chromosomes associated with severe mental retardation.

Our strategies are based on our belief that trisomies can be treated by silencing essentially the whole trisomic chromosome, which would obviate the need to decipher the complex pathologies of the resulting syndromes and determining which specific genes are most "important" (if that is even possible at any practical level) (Antonarakis et al., *Trends Mol. Med.* 12:473-479, 2006). The silencing can be carried out in a variety of cell types which naturally represent or are induced to represent a variety of developmental stages (e.g., in early embryonic stem cells or induced pluripotent stem cells, fetal cells, neonatal cells, and other types of stem cells including hematopoietic cells, neural stem cells, mesenchymal stem cells, and other types of stem cells). In preparation for human therapies, the silencing can be carried out in a mouse model of Down syndrome. Several such models are available and known in the art. One could use any of the nucleic acid constructs described herein to determine if either the abnormal phenotype (or any aspect thereof) or embryonic lethality of a Down Syndrome mouse model could be rescued or ameliorated.

Although the potential therapeutic use of Xist transgenes for chromosomal trisomies has not been envisioned in the art, we believe that the mechanism whereby nature silences one X-chromosome in females can be extended to autosomal material, based on analysis of patients that carry naturally occurring X:autosome translocations. Two patients carrying X-autosome translocations in the context of trisomy for that autosome avoided otherwise devastating clinical consequences due to silencing of autosomal regions by endogenous Xic regions (Hall et al., *Proc. Natl. Acad. Sci. USA,* 99:8677-8682, 2002) (FIG. 4). In addition, we have shown that it is possible for an Xist transgene randomly integrated into a human autosome to induce silencing in somatic cells, when it had previously been believed that it could do so only in mouse embryonic stem cells (Hall et al., *Hum. Mol. Genet.,* 11:3157-3165, 2002) (e.g., see "Chr. 4 Barr Body in FIG. 3). We have cultured and used the transgenic cells described herein, and we have observed highly stable Xist expression and autosome silencing. We have also found evidence that two cultured (neoplastic) cell lines support chromosome silencing to a large degree at most of the random integration sites tested (Chow et al., *Proc. Natl. Acad. Sci. USA* 104:10104-10109, 2007). A caveat to these studies is that they were done in transformed cell lines, leaving open the possibility that the neoplastic changes somehow allow formation of Xi heterochromatin. However, several recent studies from our lab and others demonstrate that cancer cells most commonly lose heterochromatin, including the inactive X (Pageau et al., 2007), thus we believe this is unlikely to be the explanation. No prior studies have described the use of a transgenic construct that is integrated into an autosome in a site-specific manner. The present nucleic acid constructs include targeting elements (e.g., first and second targeting elements) that drive integration of a silencing sequence (e.g., an Xist transgene) into a selected or targeted region of the genome (e.g., into a trisomic chromosome). The first and second sequences and/or the first and second targeting elements are nucleic acid sequences that share sequence homology (including sequence identity) with a chromosomal site and, due to base pairing between the first and second sequences (and/or the first and second targeting elements) and sequences present at the chromosomal site, promote site-specific integration of all or part of a nucleic acid construct of which they are a part into the chromosomal site.

Integrated Mouse Xist or human Xist transgenes can silence an autosome, as shown by studies in mouse embryonic stem cells (Wutz and Jaenisch, *Mol. Cell,* 5:695-705, 2000; Savarese et al., *Mol. Cell. Biol.* 26:7167-7177, 2006) and in human somatic (fibrosarcoma) cells (FIG. 3; Hall et al., *Hum. Mol. Genet.* 11:3157-3165, 2002; Chow et al., *Proc. Natl. Acad. Sci. USA* 104:10104-10109, 2007). Natural autosomal silencing by Xist was also shown in patient cells, with an autosomal trisomy due to X;autosome translocations (Hall et al., *Proc. Natl. Acad. Sci. USA* 99:8677-8682, 2002; (FIG. 4)). Although the silencing of autosomal material may not be quite as complete or may vary somewhat between autosomal regions, autosomes studied to date are largely if not entirely silenced in response to Xist RNA. While Chr. 21 has not been directly tested, its small (~50 Mb) acrocentric (essentially no short arm) structure is favorable, since Xist RNA would not need to spread far or across a centromere.

The fact that, to our knowledge, targeted inactivation of autosomes has never been discussed in the literature, possibly due to the belief that an Xist transgene cannot silence a chromosome outside a very narrow and early embryonic window and/or because the use of Xist transgenes for chromosomal therapeutic purposes was not envisioned. However, our studies of human Xist transgenes in adult cells and in differentiated embryonic cells (induced to express Xist post-differentiation) lead us to believe that the potential for Xist-mediated chromosome therapy in somatic cells is significant.

Figure 4:
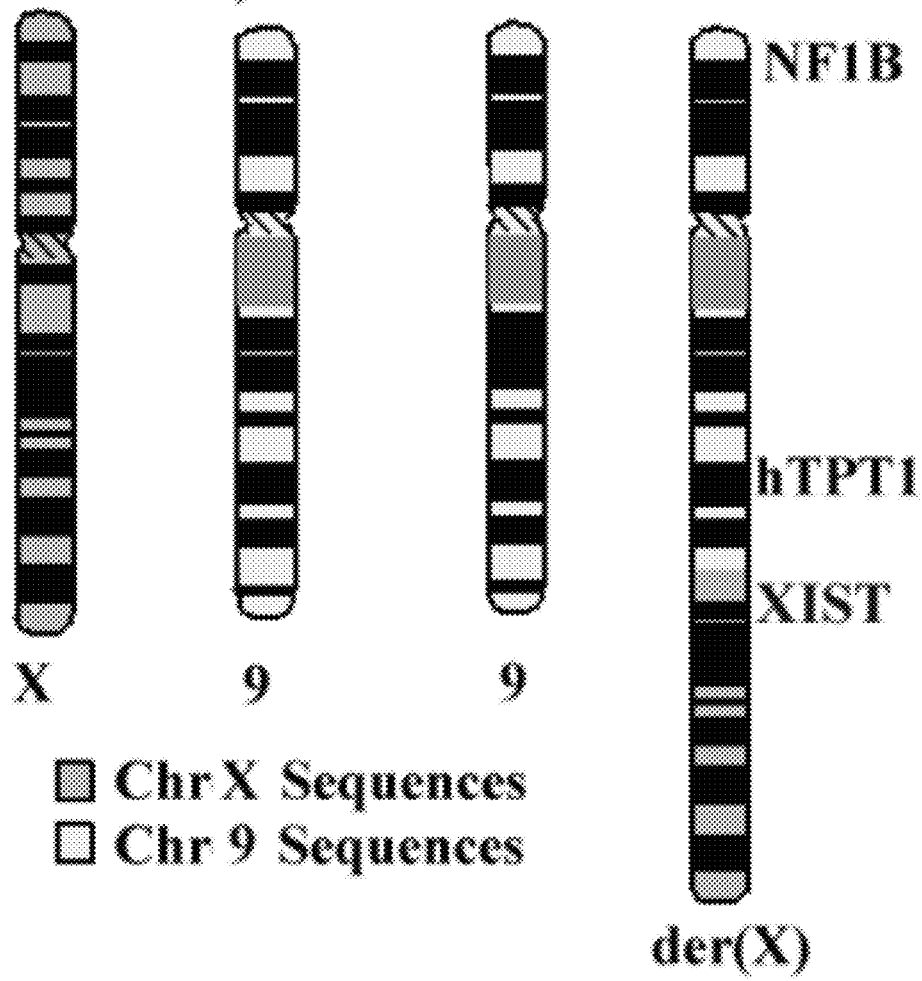
FIG. 4 is a schematic diagram of a karyotype of chromosomes involved in X; 9 translocation, in which Xist RNA was shown to silence the duplicated Chromosome 9 material in the transgene, thereby avoiding the deleterious effects of partial Chr. 9 trisomy.

The present compositions and methods are applicable to abnormalities involving duplication of chromosomal material. Duplication of even a small chromosome fragment has severe clinical consequences. For example, Turner's syndrome (45, X) females have only one X-chromosome but typically have a quite mild phenotype, with normal intelligence but primary amenorrhea and sterility. However, Turner syndrome fetuses often have a fragment of the second X chromosome, which can result in either a very severe phenotype or the Turner-like mild one. A key to whether this fragment will be deleterious is whether or not it contains the Xist gene (Nussbaum et al., *Thompson and Thompson Genetics in Medicine*, Philadelphia, Pa., Saunders/Elsevier, 2007). If the Xist gene is present, the chromosome fragment is silenced and the deleterious effects are avoided. Thus, Xist could be inserted into an abnormal chromosome that lacks Xist sequences. Another category of duplication events arises via imbalanced translocations, and we have previously characterized two examples in which the imbalance was rescued by the Xist gene on the translocated chromosome. FIG. 4 shows the karyotype of an individual with a normal phenotype, even though they carried a Chr. 9 trisomy which would otherwise be lethal. Instead, the extra chr. 9 material was silenced by the Xist gene on the translocated chromosome. We showed that Xist RNA coated much of the Chr. 9 material, as it did Chr. 14 material in an analogous example, and in both cases Xist nullified what would have been a devastating trisomy (reviewed in Hall and Lawrence, *Semin. Cell Dev. Biol.* 14:369-378, 2003). Similarly, Xist transgenes could potentially silence any rearrangement which creates duplication (partial trisomy) for part of a chromosome.

Nucleic Acid Constructs:

Accordingly, the present invention features nucleic acid constructs that include a silencing sequence and one or more targeting sequences (e.g., first and second sequences that flank the silencing sequence and direct insertion of the silencing sequence into a targeted chromosome). The silencing sequence can be or can include the sequence of an XIC (X inactivation complex) locus or any portion thereof that encodes an RNA capable of silencing the chromosome into which it has been inserted. For example, the constructs can include an XIC locus lacking the sequences 3' to Xist that trigger the "counting" mechanism. Other constructs can include the Xist gene, with or without some or all of the intronic sequences, or a biologically active variant of the Xist gene (e.g., a fragment or other mutant). For information regarding the structure of XIC, one can consult Wutz and Gribnau (*Curr. Opin. Genetics Dev.* 17:387-393, 2007).

The silencing sequence (e.g., an Xist transgene) can silence the expression of one or more genes located within a trisomic and/or translocated chromosomal region located in cis to the integrated Xist transgene. In certain embodiments, the targeting elements are sequences homologous to those that occur naturally in the trisomic and/or translocated chromosomal region and will promote integration of the silencing sequence (e.g., an Xist transgene) to the corresponding trisomic and/or translocated chromosomal region. The targeted region may be a polymorphic region (i.e., a region where corresponding sequences differ between paired chromosomes in an individual). Whether the present nucleic acid constructs are used alone or in combination with a second moiety that enhances or facilitates homologous recombination (e.g., a zinc finger nuclease), the targeted region can be one having only one or more polymorphic sites, such as single nucleotide polymorphisms (SNPs). Zinc finger domains can recognize and target highly specific chromosomal sequences, including SNPs, which can be used to facilitate targeted integration of the transgene to particular alleles in just one of the homologous chromosomes. As noted, a vector that may facilitate both insertion of a transgene and delivery to a cell is an adeno associated virus, but delivery of the transgene to cells in vitro may be done by commonly used transfection methods, without the use of any adeno-associated, lenti or other virus.

In certain other embodiments, the targeting elements are homologous to non-naturally occurring sequences that have been introduced into a trisomic and/or translocated region by recombinant methods. In these embodiments, the targeting elements will promote integration of the transgene at a site defined by the non-naturally occurring sequences, such as FRT sequences, which can promote integration into that site.

Regardless of whether the silencing sequence is inserted with the assistance of a polymorphism on the targeted chromosome or whether the nucleic acid constructs are used in combination with a second moiety that enhances or facilitates homologous recombination, the present compositions and methods can be designed to target just one copy of a chromosome if desired. These methods can also be used to target one or more than one site on a targeted chromosome (e.g., two, three, or four sites), which may or may not be in close proximity to one another. While it is our expectation that the RNA encoded by the silencing sequence or transgene will silence most if not all of the genes residing on the targeted chromosome, one can nevertheless target specific genes (e.g., genes associated with Alzheimer's Disease (e.g., APP), leukemias (e.g., RUNX1) or other conditions that occur with increased frequency in patients with trisomies or translocation).

As would be understood in the art, the term "recombination" is used to indicate the process by which genetic material at a given locus is modified as a consequence of an interaction with other genetic material. Homologous recombination indicates that recombination has occurred as a consequence of interaction between segments of genetic material that are homologous or identical. In contrast, "non-homologous" recombination indicates a recombination occurring as a consequence of the interaction between segments of genetic material that are not homologous (and therefore not identical). Non-homologous end joining (NHEJ) is an example of non-homologous recombination.

As used herein, an Xist transgene refers to a nucleic acid sequence having the sequence of all or part of a naturally occurring Xic region so long as it (a) includes an Xist RNA coding sequence or a biologically active variant thereof and (b) is functional (e.g., the Xist transgene is capable of silencing the expression of one or more genes in cis when integrated into a chromosome). The Xist transgene may carry one or more regulatory elements found in the Xic region that are not a part of the Xist coding sequence. For example, deletion of the DXPas34 locus found 3' to the Xist coding sequence eliminates Xist expression in mammalian embryonic stem cells as described in Debrand et al. (*Mol. Cell. Bio.*, 19:8513-8525, 1999) herein incorporated by reference. As a further example, silencing by mouse Xist transgenes have been shown to require a conserved repeat sequence located at the 5' end of Xist (Wutz et al., *Nat. Genetics,* 30:167-174, 2002).

The Xist transgene need not include the whole of the Xist gene sequence, although it may. For example, the Xist transgene may be derived from an Xist cDNA cloned from one of multiple naturally occurring splice variants. This cDNA may lack sequences corresponding to one or more introns or exons or portions thereof. Additionally, the Xist transgene may include non-naturally occurring Xist coding sequences. For example, the Xist coding sequence may be mutated (e.g., truncated) or otherwise variant with respect to naturally occurring Xist coding sequences so long as it includes sequences that are required for transgene function. For example, deletion analysis demonstrates that the first exon of human Xist is sufficient for both transcript localization and the induction of silencing (Chow et al., *Proc. Natl. Acad. Sci. USA* 104:10104-10109, 2007). Thus, smaller Xist constructs can be generated that are more easily manipulated but still biologically active.

Non-limiting examples of Xist transgenes (derived from mouse and human sequences) that are useful in this invention are described in the following references which are herein incorporated by reference: Chow et al. (*Proc. Natl. Acad. Sci. USA* 104:10104-10109, 2007); Hall et al. (*Proc. Natl. Acad. Sci. USA* 99:8677-8682, 2002); Chow et al. (*Genomics*, 82:309-322, 2003); and Wutz et al. (*Nat. Genet.*, 2002, 30:167-174, 2002).

The nucleic acid constructs of this invention include targeting sequences or elements that promote sequence specific integration of an Xist transgene into a chromosomal site (e.g., by homologous recombination). Methods for achieving site-specific integration by ends-in or ends-out targeting are known in the art and in the nucleic acid constructs of this invention, the targeting elements are selected and oriented with respect to the Xist transgene according to whether ends-in or ends-out targeting is desired. In certain embodiments, two targeting elements flank the Xist transgene.

As described previously, the targeting element may be identical in sequence to a naturally occurring sequence found in a trisomic and/or translocated chromosomal region. For example, a targeting element may be identical in sequence to a sequence found in any one of human chromosomes 9, 13, 14, 18, or 21 (as described in Hattori et al., *Nature*, 405:311-319, 2000) or in any other chromosome. In another example, a targeting element may be identical in sequence to a sequence found in any one of mouse chromosomes 16, 17, or T($17^{16}$)65Dn.

A targeting sequence or element may vary in size. In certain embodiments, a targeting element may be at least or about 100, 200, 300, 400, 500, 600, 700, 800, 900, 1000, 2000, 3000, 4000, 5000, 6000, 7000, 8000, 9000, 10000 bp in length (or any integer value in between). In certain embodiments, a targeting element is homologous to a sequence that occurs naturally in a trisomic and/or translocated chromosomal region, including a polymorphic sequence which may be present on just one of the homologous chromosomes.

Accordingly, in one aspect, the invention provides an isolated or purified nucleic acid construct that includes a silencing sequence (e.g., an Xist transgene) and one or more targeting sequences that are oriented with respect to each other in such a way that the Xist transgene can be integrated in a site-specific fashion into a chromosomal site when the nucleic acid construct is introduced into a cell.

The construct elements as described here may be variants of naturally occurring sequences. Preferably, any construct element (e.g., an Xist transgene, other non-coding, silencing RNA, or a targeting element) includes a nucleotide sequence that is at least 60% identical to its corresponding naturally occurring sequence (its reference sequence, e.g., an Xist coding region, a human Chr 21 sequence, or any duplicated or translocated genomic sequence). More preferably, the silencing sequence or the sequence of a targeting element is at least 65%, 70%, 75%, 80%, 85%, 90%, 91%, 92%, 93%, 94%, 95%, 96%, 97%, 98%, 99% identical to its reference sequence (e.g., SEQ ID NO:1 or SEQ ID NO:2).

As used herein, "% identity" of two nucleic acid sequences is determined using the algorithm of Karlin and Altschul (*Proc. Natl. Acad. Sci. USA*, 87:2264-2268, 1990), modified as in Karlin and Altschul, *Proc. Natl. Acad. Sci. USA*, 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (*Nucl. Acids Res.*, 25:3389-3402, 1997). When utilizing BLAST and Gapped-BLAST programs the default parameters of the respective programs (e.g., XBLAST and NBLAST) are used to obtain nucleotide sequences homologous to a nucleic acid molecule of the invention.

The nucleic acid constructs of the invention can be prepared by recombinant methods that are known in the art.

Moreover, the present invention provides a vector containing one or more of the nucleic acid constructs described herein. The vector may be useful for propagating the nucleic acid construct or may contain elements useful for integrating the Xist transgene into a chromosome once the vector has been introduced into a mammalian cell. For example, the vector may be an expression vector designed to express a recombinase, such as Fok1 recombinase, coupled with a zinc finger nuclease, designed to aid in the integration of the silencing sequence (e.g., an Xist transgene) into a chromosome at a specific site.

For expression in animal cells, such as embryonic stem cells, adult bone marrow stem cells, CHO, COS, and NIH3T3 cells, the expression vector must have a promoter such as an SV40 promoter (Mulligan et al., *Nature* 277:108, 1979), MMLV-LTR promoter, EF1α promoter (Mizushima et al., *Nucl. Acids Res.* 18:5322, 1990), and CMV promoter. The vector may also carry an inducible promoter, for example, a doxycycline inducible promoter, or a promoter that may be activated to express Xist RNA by excision of intervening sequences, using a Cre-lox system. More generally, the nucleic acid construct that includes a silencing sequence can also include one or more control elements that facilitate expression of the silencing sequences. These control elements include promoter, enhancer, and termination sequences, and the promoter may be a constitutively active, inducible, tissue-specific or developmental stage-specific promoter.

Our findings further support the conclusion that chromosome inactivation also occurs in mature cells (e.g., in differentiated cells), but at a slower rate than in embryonic cells. Regarding developmental competence, we note that, in addition to the requirement for expression of an integrated Xist transgene, the cells must respond to Xist to support initiation of chromosome inactivation, which normally occurs during the earliest transition of pluripotent embryonic stem cells to more committed/differentiated cells. While all somatic cells in adult females are competent to maintain the silenced state, it has been believed that only early embryonic stem cells can initiate chromosome silencing in response to Xist. A study in mouse ES cells reported that if expression of Xist was delayed just two days after differentiation, the cells had lost the competence to initiate chromosome inactivation (Wutz et al. 2000, Molecular Cell). However, our study in human somatic cells (Hall et al., 2002, PNAS) first showed that a randomly integrated Xist transgene was able to initiate chromosome inactivation of the autosome (carrying the ectopic Xist gene) in human HT1080 cells, derived from an adult male fibrosarcoma. Our studies in Chow et al. (PNAS 2007) confirmed this for HT1080 cells and human 293 cells; however, because both of these somatic cell lines have neoplastic origins, it has been thought that their capacity to initially form the heterochromatic chromosome may not reflect the capacity of fully normal cells. However, in other work, we and others have shown that cancer cells tend to lose heterochromatin, including Xi (Pageau et al., 2007, Nature Reviews Cancer).

To further investigate whether normal, non-neoplastic somatic cells are competent to initiate chromosome inactivation post-differentiation, we differentiated mouse ES cells carrying an inducible-Xist transgene, essentially the same experimental system used in Wutz et al. Our findings demonstrate that these normal murine ES cells are able to support chromosome silencing post-differentiation. ES cells were differentiated for several (4-9) days prior to induction of Xist expression with doxycycline, and then cells were evaluated at various intervals up to two weeks following Xist expression. Whereas Wutz et al. waited just 2 days after Xist expression to evaluate whether chromosome silencing had taken place, we surmised that the multi-step inactivation process may occur more slowly in somatic cells. Indeed, our findings demonstrate that the vast majority of cells in these differentiated cultures had supported chromosome silencing, between 7-14 days after Xist expression. Thus, these findings indicate that the successful chromosome silencing in Hall et al. (2002) was likely not due to the neoplastic nature of the cells used, but to the long, ten-day time-frame over which the cells were evaluated.

While naturally occurring stem cells may have an enhanced competence to respond to Xist to initiate chromosome silencing, differentiated somatic cells, such as fibroblasts, can also be induced to form induced pluripotent stem cells (iPS cells) by introduction of specific genes that control developmental programs. The iPS cells have properties essentially like those of ES cells, and thus would be competent to not only initiate X-inactivation in response to Xist, but to form a variety of stem cells committed to specific cell types, such as neural, hematopoeitic, cardiac myoblasts, etc., which may enhance their therapeutic utility.

The present nucleic acid constructs can be used to integrate a silencing sequence (e.g., the Xist transgene) into a chromosome in murine or human embryonic, iPS, or adult stem cells (for example, see Zhang, *J. Hematotherapy & Stem Cell Research* 12:625-634, 2003, herein incorporated by reference). For example, bone marrow stem cells and induced pluripotent stem cells may be used. Pluripotency can be induced as described above by the methods of Wernig et al. (*Nature* 448:318-325, 2007); Shi et al. (*Cell Stem Cell.* 2:525-528, 2008); and Nakagawa et al. (*Nature Biotechnol.*, 26:101-106, 2008), all of which are incorporated by reference herein. In addition, neural precursor cells as described in Zhang et al. (*Nature Biotechnology*, 19:1129-1133, 2001) may be used. For example, the following steps could be used to generate a population of corrected patient stem cells of a particular type that will not be subject to immune rejection (because they are isogenic to the patient's DNA), but which can provide therapeutic value. 1) providing fibroblasts or lymphocytes or other cells from a patient with trisomy 21 (Down Syndrome); 2) treating these cells with reprogramming factors shown to generate induced pluripotent stem cells or early developmental cells; 3) introducing into these cells a zinc finger nuclease (with Fok1 recombinase) specifically designed to promote efficient integration of exogenous DNA at a specific location; 4) introducing an Xist transgene flanked by sequences homologous to the desired site of integration under the control of a promoter designed to be expressed as desired, and verifying that Xist is expressed and silences the chromosome; and 6) culturing the Xist-transgenic iPS cells under conditions that promote the generation of neural, hematological, cardiac or other desired stem cells. The corrected stem cells (in which the deleterious chromosome or region has been silenced) can then be reintroduced into the patient's body so as to achieve therapeutic benefit, by introducing the appropriate type of stem cells into the appropriate tissue or organ. For example, in Down Syndrome there is thought to be loss of neurons or neural function that appears to be progressive with age that contributes to mental retardation. Similarly, Alzheimer's Disease is associated with loss of proper neuron function. As has been shown in mouse models of another neurological disease, intracranial injection of normal neural stem cells can provide therapeutic benefit (Lee et al., *Nature Med.* 13:439-447, 2007) and, more generally, cell implantation methods, including via intracranial surgery, are known in the art. Similarly, Down Syndrome is associated with hematological abnormalities that could be treated by correcting patient cells that are natural bone marrow stem cells or induced bone marrow stem cells (from iPS cells or other mesenchymal stem cells). In a patient with TMD (transient myeloproliferative disorder, which often precedes leukemia) or leukemia, the corrected bone marrow stem cells could be introduced into the patient's blood, to repopulate the bone marrow with more normal stem cells. Similarly, babies with Down Syndrome have a high rate of congenital heart defects, which in some cases could be treated by the use of cardiac stem cell therapy, where the stem cells used would be isogenic with the patient's DNA but would be corrected by silencing the trisomic chromosome.

In addition, the vector may contain a marker for the selection of transfected cells (for instance, a drug resistance gene for selection by a drug such as neomycin, hygromycin, and G418). Such vectors include pMAM, pDR2, pBK-RSV, pBK-CMV, pOPRSV, pOP13, and so on. More generally, the term "marker" refers to a gene or sequence whose presence or absence conveys a detectable phenotype to the host cell or organism. Various types of markers include, but are not limited to, selection markers, screening markers, and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as green fluorescent protein (GFP), GUS or β-galactosidase. Molecular markers are, for example, sequence features that can be uniquely identified by oligonucleotide probing, for example RFLP (restriction fragment length polymorphism), or SSR markers (simple sequence repeat). To amplify the gene copies in host cell lines, the expression vector may include an aminoglycoside transferase (APH) gene, thymidine kinase (TK) gene, *E. coli* xanthine guanine phosphoribosyl transferase (Ecogpt) gene, dihydrofolate reductase (dhfr) gene, and such as a selective marker.

In vivo expression of the DNA of the invention may be performed by constructing the DNA into an appropriate vector and transfecting the construct into the body using retrovirus, liposome, cationic liposome, adeno-associated virus (particularly where chromosome 19 is targeted), lentivirus, electroporation and so on. It is possible to use such a construct to perform gene therapy for diseases resulting from chromosomal trisomies and/or translocations or duplications.

Examples of vectors used for this purpose include retrovirus vector (such as pZIPneo), but are not limited thereto. General manipulations, such as insertion of the DNA into the vector, may be performed by using standard methods (Molecular Cloning, 5.61-5.63). The vector may be administered to the patient through in vivo administration or by way of methods that are carried out, at least partially, ex vivo. For example, the vector may be administered to cells harvested from a patient and maintained in culture. The construct-carrying or vector-carrying cells can then be introduced to the patient. For example, stem cells or hematopoietic cells can be harvested from a patient or obtained from another source, modified in culture as described here to include insertion of a silencing sequence into a targeted site, and administered to the patient. To facilitate the method, the recipient patient may be subjected to bone marrow ablation.

Facilitating Targeting with Zinc Finger Nucleases:

Targeting the present "silencing" constructs to particular chromosomes or regions of chromosomes can be facilitated by introducing chimeric zinc finger nucleases (ZFNs) into a cell. These nucleases exploit endogenous cellular mechanisms for homologous recombination and repair of double stranded breaks in genetic material. ZFNs can be used to target a wide variety of endogenous nucleic acid sequences in a cell or organism. The present compositions include cleavage vectors that target a ZFN to a region within a trisomic chromosome or within a translocated sequence, and the methods include transfection or transformation of a host cell or organism by introducing a cleavage vector encoding a ZFN (e.g., a chimeric ZFN), or by introducing directly into the cell the mRNA that encodes the recombinant zinc finger nuclease, or the protein for the ZFN itself. One can then identify a resulting cell or organism in which a selected endogenous DNA sequence is cleaved and exhibits a mutation or DNA break at a specific site, into which the transgene will become integrated.

To help clarify the nucleic acid to which we are referring, we tend to use the term "nucleic acid construct" to describe a nucleic acid that includes the silencing sequence and the term "cleavage vector" to describe a nucleic acid that encodes the ZFN. It is to be understood, however, that both are, or include, nucleic acid sequences (e.g., DNA); both can be properly referred to as constructs; and both can be properly referred to as vectors, particularly when they include nucleic acid sequences that facilitate entry into a host cell.

The methods can include construction of a vector or isolation of an mRNA encoding a chimeric ZFN by, for example, selecting a zinc finger DNA binding domain capable of preferentially binding to a specific host DNA locus to be mutated; further selecting a non-specific DNA cleavage domain capable of cleaving double-stranded DNA when operatively linked to the binding domain and introduced into the host cell; further selecting a promoter region capable of inducing expression in the host cell; and further operatively linking DNA encoding the binding domain and the cleavage domain and the promoter region to produce a DNA construct. Elements are operatively linked when they work in concert. For example, a control element and a transgene are operatively linked when the control element alters the expression of the transgene. To bring a transgene under the control of a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA.

The nucleic acid (e.g., DNA) construct is then introduced into a target host cell and at least one host cell exhibiting recombination at the target locus in the host DNA is identified.

The ZFN can be a chimeric protein molecule that directs targeted genetic recombination or targeted mutation in a host cell by causing a double stranded break at the target locus. For example, a ZFN can include a DNA-binding domain that includes at least one zinc finger, and that binding domain can be operatively linked to a DNA-cleavage domain. The DNA-binding domain is at the N-terminus of the chimeric protein molecule, and the DNA-cleavage domain is located at the C-terminus of the molecule.

The ZFN can include multiple (e.g., at least three (e.g., 3, 4, or 5)) zinc fingers in order to improve its target specificity. The zinc finger domain can be derived from any class or type of zinc finger. For example, the zinc finger domain can include the $Cys_2His_2$ type of zinc finger that is very generally represented, for example, by the zinc finger transcription factors TFIIIA or Sp1. In a preferred embodiment, the zinc finger domain comprises three $Cys_2His_2$ type zinc fingers.

The DNA recognition and/or the binding specificity of a ZFN can be altered in order to accomplish targeted genetic recombination at any chosen site in cellular DNA. Such modification can be accomplished using known molecular biology and/or chemical synthesis techniques. ZFNs comprising zinc fingers having a wide variety of DNA recognition and/or binding specificities are within the scope of the present invention.

The ZFN DNA-cleavage domain can be derived from a class of non-specific DNA cleavage domains, for example the DNA-cleavage domain of a Type II restriction enzyme such as FokI. Thus, a chimeric ZFN useful in the present methods can include three $Cys_2His_2$ type zinc fingers and a DNA-cleavage domain derived from the Type II restriction enzyme FokI. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer."

A linker, if present, between the cleavage and recognition domains of the ZFN can be a sequence of amino acid residues that result in a flexible linker is flexible, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

A silencing sequence flanked by sequences (typically 400 bp-5 kb in length) homologous to the desired site of integration can be inserted (e.g., by homologous recombination) into the site cleaved by the endonuclease, thereby achieving a targeted insertion. When used in combination with a ZFN construct, the silencing sequence may be referred to as "donor" nucleic acid or DNA.

The various active sequences, including the silencing sequence and the sequence encoding a chimeric ZFN can be introduced into a host cell on the same vector or separately (e.g., on separate vectors or separate types of vectors at the same time or sequentially). Methods for introducing the various nucleic acids, constructs, and vectors are discussed further below and are well known in the art.

The nucleic acid constructs including a silencing sequence, whether used alone or in combination with a ZFN can either introduce a therapeutic sequence or disrupt a targeted sequence, gene, or chromosome in a somatic cell or in a germ cell. In some cases, a therapeutic Xist transgene may be inserted in such a way as to simultaneously disrupt a deleterious gene, such as the APP gene that leads to high incidence of Alzheimer's Disease. Cells with such disruption in the targeted gene can be "selected for" in order to create an organism without a functioning target sequence or for administration to a patient. Accordingly, the constructs, other compositions, and methods of the present invention are applicable to a wide range of cell types and organisms. While our own intention is to develop therapies for human patients, the silencing methods we have discovered can be carried out with a single celled or multicellular organism; an oocyte; a gamete; a germline cell in culture or in a host organism; a somatic cell in culture or in a host organism; an insect cell, including an insect selected from the group consisting of Coleoptera, Diptera, Hemiptera, Homoptera, Hymenoptera, Lepidoptera, or Orthoptera, including a fruit fly, a mosquito and a medfly; a plant cell, including a monocotyledon cell and a dicotyledon cell; a mammalian cell, including but not limited to a cell of a mouse, rat, pig, sheep, cow, dog, cat, or human; an avian cell, including, but not limited to a cell of a chicken, turkey, duck or goose; or a fish cell, including, but not limited to zebrafish, trout and salmon.

DNA encoding an identifiable marker can also be included with either the nucleic acid construct including the silencing sequence or the vector carrying the ZFN-encoding sequence. Such markers may include a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), beta-glucuronidase (GUS) or beta-galactosidase. Markers may also be negative (e.g., codA) or positive selectable markers. Molecular markers are, for example, sequence features that can be uniquely identified by oligonucleotide probing, for example RFLP (restriction fragment length polymorphism), or SSR markers (simple sequence repeat).

The compositions and methods described herein can be used to accomplish germline gene therapy in mammals.

The frequency of homologous recombination in any given cell is influenced by a number of factors. Different cells or organisms vary with respect to the amount of homologous recombination that occurs in their cells and the relative proportion of homologous recombination that occurs is also species-variable. The length of the region of homology between donor and target affects the frequency of homologous recombination events, the longer the region of homology, the greater the frequency. The length of the region of homology needed to observe homologous recombination is also species specific. However, differences in the frequency of homologous recombination events can be offset by the sensitivity of selection for the recombinations that do occur. It will be appreciated that absolute limits for the length of the donor-target homology or for the degree of donor-target homology cannot be fixed but depend on the number of potential events that can be scored and the sensitivity of the selection for homologous recombination events. Where it is possible to screen $10^9$ events, for example, in cultured cells, a selection that can identify 1 recombination in $10^9$ cells will yield useful results. Where the organism is larger, or has a longer generation time, such that only 100 individuals can be scored in a single test, the recombination frequency must be higher and selection sensitivity is less critical. Random integration is discussed elsewhere herein. We note here, however, that random integration can be used in combination with selection for cells that have targeted the desired gene or chromosome.

Transformation can be carried out by a variety of known techniques which depend on the particular requirements of each cell or organism. Such techniques have been worked out for a number of organisms and cells and are readily adaptable. Stable transformation involves DNA entry into cells and into the cell nucleus. For single-celled organisms and organisms that can be regenerated from single-cells (which includes all plants and some mammals), transformation can be carried out in culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors. Other techniques are well known in the art.

Where silencing is limited to less than an entire chromosome, boundary elements or sequences associated with escape from inactivation can be used to help impede the spread of the silencing RNA. For a description of a unique sequence feature of the X-chromosome that always escapes inactivation, see McNeil et al. (*Genome Res.* 16:477-484, 2006). This sequence is among those that can be used to confer "escape" from silencing. See also Filippova et al. (*Dev. Cell.* 8:31-42, 2005).

In the following paragraphs, we describe some delivery systems useful in practicing the present invention.

Liposomal formulations: In certain embodiments of the invention, the oligo- or polynucleotides and/or expression vectors containing silencing sequences and/or ZFNs may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids and liposomes suitable for use in delivering the present constructs and vectors can be obtained from commercial sources or made by methods known in the art.

Microinjection: Direct microinjection of DNA into various cells, including egg or embryo cells, has also been employed effectively for transforming many species. In the mouse, the existence of pluripotent embryonic stem (ES) cells that can be cultured in vitro has been exploited to generate transformed mice. The ES cells can be transformed in culture, then microinjected into mouse blastocysts, where they integrate into the developing embryo and ultimately generate germline chimeras. By interbreeding heterozygous siblings, homozygous animals carrying the desired gene can be obtained.

Viral Vectors as Expression Constructs:

Other viral vectors may be employed as expression constructs in the present invention. Vectors derived from, for example, vaccinia virus, adeno-associated virus (MV), and herpes viruses may be employed. Extensive literature is available regarding the construction and use of viral vectors. For example, see Miller et al. (*Nature Biotechnol.* 24:1022-1026, 2006) for information regarding adeno associated viruses. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was subsequently detected.

Non-Viral Methods:

Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression constructs may simply consist of naked recombinant DNA, or in some cases mRNA for the recombinant ZFN. Transfer of the construct may be performed by any of the nuclei acid transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

EXAMPLES

Silencing a Trisomic Chromosome in Human Somatic Cells and in a Trisomic Mouse Model of DS We will introduce an Xist transgene into human and mouse trisomic cells, and demonstrate silencing of the trisomic chromosome in culture. We believe that human Xist transgenes can: (1) initiate silencing outside of the normal very early development window in normal (non-neoplastic) human somatic cells and/or stem cells; (2) be targeted to and effectively silence an autosome (e.g., trisomic human chromosome 21) in human cultured cells; and with higher efficiency techniques, (3) stably silence the trisomic chromosome in mouse ES cells and mice in an established mouse model of Down Syndrome, thereby ameliorating the deleterious phenotype. Trisomic mouse models of Down Syndrome are available and can be used to test both chromosome silencing and amelioration of the phenotype of DS mice (see below).

Experiments in Mouse ES or iPS Cells and a Mouse Model of Down Syndrome:

The goal of these studies is to first target an Xist transgene into ES, iPS or bone marrow cells derived from one or more mouse models of Down Syndrome and verify that the trisomic chromosome is effectively silenced. Two available mouse DS models carry trisomy chr. 16 (syntenic to human 21) and one carries an actual human Chr 21 as the third chromosome (further detailed below).

Trisomic Mouse Models of DS:

Mouse chromosome 16 is largely syntenic to human chromosome 21, and mouse models of DS have been developed that are either trisomic for mouse chr. 16, or carry as the third chromosome an actual human chromosome 21 (reviewed in Reeves *Trends Mol. Med.* 12:237-240, 2006). There are mouse strains with segmental trisomies, such as Ts65Dn, which carries a segment (15.6-Mb) of mouse chromosome 16 on a marker chromosome (Reeves et al., *Nat. Genet.* 11:177-184, 1995). The extra $T(17^{16})65Dn$ marker chromosome produces a trisomy for the mouse orthologs of about half of the human genes on chr. 21. Mice display a number of DS-like phenotypes, including an overall reduction in size and growth rate, altered noradrenergic transmission in the hippocampus and cerebral cortex and degeneration of basal forebrain cholinergic neurons, and defects in cranial bone development (Hill et al., *J. Anat.* 210:394-405, 2007; Olson et al., *Hum. Mol. Genet.* 16:774-782, 2007). In addition, trisomic females have smaller and fewer litters and trisomic males display hypospermia. Another mouse model, Ts16, carries an essentially complete third copy of mouse chr. 16, involving a Robertsonian translocation of chr 16 (Epstein et al., *Ann. NY Acad. Sci.* 450:157-168, 1985). As with other mouse full trisomies, these mice die during fetal development, so all studies are done on the fetal mice or cells derived from fetuses. However, for our purposes the severity of the phenotype would potentially make the therapeutic benefits clearer, if we should see an increase in viability upon inactivation of one copy of chromosome 16. The $Rb(6.16)24Lub/Rb(16.17)_7BnrF_1$ Robertsonian translocation mouse strain (used to generate Ts16) and the Ts65Dn mouse strain are available from the Jackson Laboratory.

Another interesting mouse DS model (Tc1) carries an almost complete human chromosome 21, and exhibits several characteristics that are reminiscent of Down Syndrome (O'Doherty et al., *Science* 309:2033-2037, 2005). However, this model is less attractive as it is not clear how well human Xist would silence a human chromosome in an otherwise mouse nucleus; our prior study of mouse/human hybrids showed that human Xist RNA may not localize properly. Thus, we have decided to begin with the Ts65n model which carries a partial chr 16 trisomy and is more straightforward. We summarize the approach for this system, but other models can be tested similarly.

Generation of Mouse Down's Syndrome ES Cells and iPS Cells:

The Ts65Dn mouse model (B6EiC3Sn a/A-Ts($17^{16}$) 65Dn) has been obtained from the Jackson Laboratory (stock number 001924) (Roper et al., *Genetics* 172:437-443, 2006). Female T($17^{16}$)65Dn mice have been mated to 129SV/EV males, and a number of litters produced. DS pups have been identified by karyotyping cytogenetic preps, and using FISH on interphase cells from tail tip Fibroblasts and whole blood.

Generation of Trisomic ES Cells:

Blastocysts will be harvested from the mating of Ts65Dn females with 129SV/EV males, to derive ES cells, using standard procedures, DS embryos can also be generated by somatic cell nuclear transfer of a fibroblast from a Ts65Dn mouse into an enucleated normal mouse egg.

Generation of Trisomic iPS Cells:

Fibroblasts from DS pups have been isolated and iPS cells generated using lentivirus expression of 4 pluripotency genes (mOct4, mSox2, mKlf4, mc-Myc). Twenty hours post-transduction, the virally transduced cells were resuspended in ES cell growth medium and re-seeded. The following day the pluripotency genes were induced with doxycycline. Colonies that appear (ours started showing up by day 3), are replated onto inactivated feeder MEFs. Doxycycline is removed once colonies are verified to express the other pluripotency markers (SSEA-1, Nanog, etc), between 14 and 22 days. Resulting colonies are then cultured on feeders in the absence of dox, similar to normal mouse ES cells. These iPS cells can now be used to target Xist to chromosome 16.

Targeting the Xist Transgene to a Trisomic Chromosome in Mouse Cells and Assessing Silencing of Chr 16:

The Xist transgene will be targeted into a specific region of chromosome 16 in the trisomic iPS cells. We will target the region critical for Down's syndrome on chromosome 16, using as preferred targeting sites some of the genes important to the pathology of Down's syndrome (e.g., Runx-1, APP, Dyrk1A, etc). The transgene can have a constitutive or inducible promoter. We have begun to construct a targeting transgene which incorporates Xist cDNA sequences from an Xist cDNA that we have obtained by Anton Wutz (Research Institute of Molecular Pathology, Vienna) (Savarese et al., *Mol. Cell. Biol.* 26:7167-7177, 2006). This Xist transgene contains an inducible promoter and Xist cDNA, but lacks the 3' sequence necessary for counting. Thus, it will not be susceptible to random inactivation in the female ES cells. We are modifying this transgene with appropriate promoters, homologous targeting sequences, and inducible system to make it appropriate for targeting the Xist transgene to the specific chromosome in iPS cells. It will be expressed during cell differentiation, for optimal silencing.

We will be using established mouse gene targeting protocols on our iPS cells. We are currently designing an Xist targeting construct using a vector previously validated to efficiently target the Runx1 gene. Runx1 is located in the critical region of chr16, has been linked to leukemia, and likely plays a role in the hematological abnormalities seen in DS individuals (mouse and human). The targeting vector can also include a GFP mini-gene to facilitate identification of transgenic cells and to confirm silencing of this gene. Selectable markers will facilitate identification of properly targeted clones, using known procedures. Similarly, targeting can be to the APP gene which is known to be important to Alzheimer's Disease or other gene important in other diseases.

In mouse models of DS, we can not only manipulate mouse ES or iPS cells, which are known to support chromosome silencing, but also test two critical points in the proof-of-principle: that stable silencing of the third chromosome (carrying an Xist transgene) can be achieved, and that this can have ameliorating effects on the disorder, at the whole organism level. Our plan is to initially target the Xist transgene into a trisomic chromosome of "Down Syndrome" mouse ES/iPS cells, induce silencing and confirm that it silences, and then generate mice (or chimeric mice) from these engineered ES/iPS cells. If this procedure successfully silences and mitigates the phenotype, we can use an inducible promoter to induce Xist expression at later stages of development, to determine how late effective silencing and mitigation of the disorder can be achieved. Also, the original TS64DN non-modified mice may also be used to examine the effects of reintroducing bone marrow, after chromosome modification, on the hematological abnormalities in DS mice (these studies are further detailed below).

Figure 5:
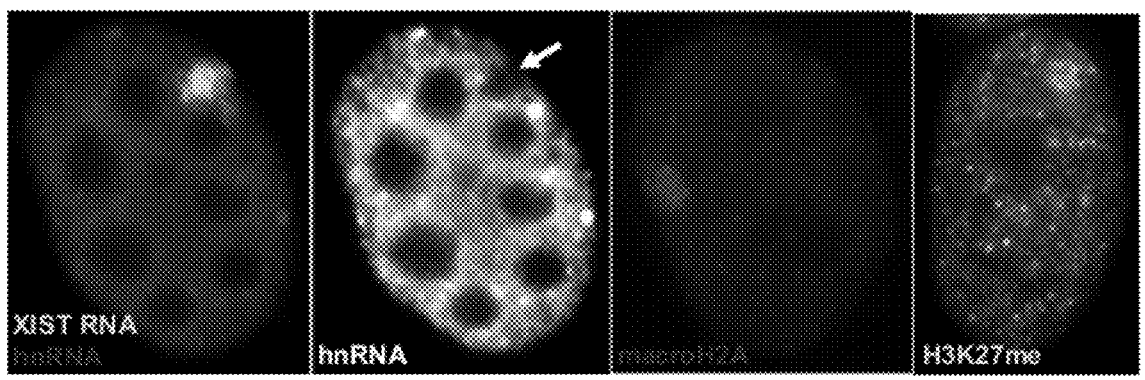
FIG. 5 is a panel of four images of the same cell showing, from left to right, Xist RNA localization, hnRNA, macroH2A localization, and H3K27me localization.

Validation of Targeting and Silencing:

As we have previously published, single cell analysis by molecular cytological methods (immunofluorescence and FISH), will be used to validate targeting and the extent of chromosomal silencing in differentiated iPS cell cultures (FIG. 5). RNA FISH for single genes or real-time PCR or microarrays will be used to examine gene expression levels in targeted versus non-targeted iPS cells. We will initially determine by fluorescence in situ hybridization whether the Xist gene is expressing and producing a localized accumulation that "paints" the chromosome. This is a very distinctive relationship of RNA to the chromosome that is almost always correlated with silencing, which our lab first discovered and established (Clemson et al., *J. Cell Biol.* 132:259-275, 1996). If Xist RNA coated chromosomes are observed, we will then use other Xi hallmarks (e.g., hybridization to hnRNA, immunofluorescence to H3K27 methylation or macroH2A) to further validate the silencing, as shown in FIG. 5 and in our published papers.

In addition, as stated above, we will generate mice from the modified mouse iPS (or ES) cells to test the prediction that the trisomic chromosome can be silenced and the deleterious phenotype will be substantially ameliorated (this is further detailed below).

Experiments in Human Primary or iPS Down Syndrome Cells:

Several DS human cell types are available to generate DS iPS lines from, including DS patient fibroblasts and bone marrow. We have acquired three primary DS fibroblast lines and two bone marrow cell lines, and have TERT immortalized one female DS fibroblast line. We plan to generate iPS cells from both primary as well a TERT immortalized DS lines, using lentivirus expression of 4 pluripotency genes similar to the methodology used in developing the mouse DS iPS cell lines. We have also acquired a DS iPS line from Harvard Stem Cell Institute.

Studies in Human Primary Cells:

Although iPS cells can now be made from primary lines, we can also test the developmental competence of terminally differentiated primary human cells to support silencing in response to an inducible Xist transgene integrated into an autosome. This may help define whether more differentiated cell types may also be available for chromosome therapy in the future. Some of our studies have been aimed at determining whether somatic or only stem cells can support chromosome silencing of an autosome. A prior study of transgenic mouse ES cells concluded that Xist did not induce silencing just a few days after the earliest embryonic differentiation (Wutz et al.), however this study examined silencing just two days after Xist expression. We have shown that adult human somatic cells can initiate silencing of an autosome carrying an Xist transgene (Hall et al., *Proc. Natl. Acad. Sci. USA*

99:8677-8682). However, the study indicated this took at least 10 days to occur in somatic cells. Thus, we will examine chromosome silencing after two or more weeks and are hopeful that somatic cells will largely retain the ability to induce chromosome silencing, albeit more slowly than in ES cells. Our recent findings indicate that human ES cells (hESCs) also support silencing of the normal X chromosome in culture similar to that seen for the mouse. We have also derived a sub-line of neural stem cells (from hESCs), and we will test their competence to support silencing, which may be particularly relevant to future DS therapeutic applications. It may also be possible to partially reprogram somatic cells, such that they more closely resemble adult stem cells instead of ES/iPS cells, and assess the competence of these partially reprogrammed cells to inactivate.

Wutz lab (Savarese et al., *Mol. Cell. Biol.* 26:7167-7177, 2006) suggests that bone marrow stem cells may retain capacity to support chromosome silencing post-embryonic differentiation, but our close reading of this data suggests to us that some or many more cell-types in fetal or adult mice still retain the capacity for X-inactivation. For reasons summarized below, we are particularly interested in testing this strategy in DS bone marrow cells. Thus, for these experiments, rather than use transformed cell lines, we will test several different primary somatic cell types, including DS patient fibroblasts and bone marrow cells, primary diploid myoblasts, epithelial cells, and trisomic amniocytes (available from Coriell Cell Repositories, Camden, N.J.). The developmental competence of these cells will be compared to TERT immortalized primary DS lines, and embryonic and neural stem cells, including those derived from induced pluripotent stem (iPS) cells generated from patient somatic cells.

These questions regarding the developmental competence of cells to enact chromosome silencing do not require targeted integration (we will use the methodology that provides the highest efficiency of integration), and is similar to work we have done successfully with transformed cell lines.

Incorporation of the ZFN Technology to Target the Xist Transgene to a Trisomic Chromosome in Human Cells and Assess Silencing of Chr 21 (or Chr 13):

We will test the best strategies to target human Chr 21 (or Chr 13) and to confirm the effectiveness of silencing. Conventional targeting strategies as well as a new zinc-finger based methodology will be used for targeting the Xist transgene to Chr 21. This will be assessed both with and without the use of selection, and by using the endogenous or an inducible promoter (as in our papers). Selection might be utilized with future ES/iPS methodologies, but would not be an option in vivo; see Moehle et al. (*Proc. Natl. Acad. Sci. USA,* 104:3055-3060, 2007). The constructs lack the sequences 3' to Xist that trigger the "counting" mechanism, so this will not complicate results.

We will use site-specific targeting, using zinc finger nucleases (ZFNs). This approach provides much higher integration efficiency, without a requirement for selection. More specifically, this method uses the cells own machinery for double strand break repair to improve the efficiency of gene targeting. The zinc finger motifs can be engineered to recognize almost any sequence, and we will engineer ZFN transgenes that target two or more sites of Chr. 21. The transgene encoding the ZFN can be introduced along with a vector carrying the gene to be inserted flanked by a few hundred by of DNA homologous to the target site. Recent studies have achieved targeted integration rates of about 5 to 20% without selection with integration of up to 8 kb of DNA (Urnov et al., *Nature* 435:646-651, 2005; Moehle et al., *Proc. Natl. Acad. Sci. USA* 104U; 3055-3060, 2007). If very high efficiency is obtained, it is possible that we could get integration into two copies of the chromosome in some cells. If this occurs, we will target polymorphic sites. In addition, these methods have shown particular promise for use in human ES cells.

We will begin these studies in 293 cancer cells that transfect at very high efficiency, and then move on to TERT immortalized trisomy 21 fibroblasts, and iPS cells generated from these DS lines. We anticipate that most autosomal material is competent to be inactivated in response to Xist RNA. However, because there is some sequence specificity to this process, we will determine the effectiveness of chromosome 21 silencing specifically using molecular cytological assays. Presuming this shows silencing, we will use microarray analysis to determine the profile of gene expression for Chr. 21 genes, in comparison to the trisomic cells (without the transgene) and normal cells. In addition to the trisomy 21 cells, one of the human ES cell lines approved by the NIH carries a trisomy for chr. 13. We will study Chr. 13 inactivation in these cells, both as undifferentiated ES cells and as cells differentiated along a neuronal pathway.

Utilizing Random Integration of Xist:

In some studies, we will use the ZFN technology described above, but analyses can also be done using our protocol for random integration with the same constructs and transfection approach that we have successfully used before (Hall et al. 2002b; Chow et al. 2007). In these experiments, transgenes can be designed to select against cells in which the trangene has not integrated. If integration is into a disomic chromosome which is then silenced, this would create a functional monosomy, which would reduce or severely reduce cell viability. In contrast, if the random integration involved the trisomic chromosome in a DS cell line, there is likely to be a growth advantage to these "corrected" cells within the population, and this, coupled with selection against cells where integration generated a functional monosomy, may generate a strong selection for the desired cells in which the random integration was into the trisomic chromosome even without targeting methodologies. This same natural selective disadvantage of functionally monosomic cells may provide a natural protection against the less frequent occurrence that two of the trisomic chromosomes are silenced, as such cells would be selected against as they are in human development. (In individuals mosaic for Down Syndrome where a non-disjunction even generates a trisomic cell-line and a monsomic cell line, the monosomic cell line is not see; these cells die.). However, we have also shown that transfectants can be selected for drug expression (prior to chromosome inactivation), and the integration site and impact on chromosome silencing can be determined in several different clones or in pooled populations of random integrants.

Further Studies Using the Down's Syndrome Mouse Models

Use Trisomic Mouse ES/iPS Cells Carrying the Xist-Transgene to Generate Mice and Assess Phenotype:

The targeted ES/iPS cells can be injected into blastocysts of albino C57B1/6 E3.5 to generate mice in which coat color changes can be used to assess the degree of chimerism or into the blastocysts of trisomic Ts65n blastocysts. The latter mice would be "mosaic" for the Xist-transgenic trisomic cells and uncorrected trisomic cells, providing a good model of partial correction. In addition, routine methods using blastocysts that have undergone tetraploid fusion can generate mice completely derived from the modified ES cells.

To assess the corrective effects of Xist-mediated silencing of the T($17^{16}$)65Dn chromosome in this model for DS, we will measure birth weight and growth throughout the postnatal period, as well as correction of defects in craniofacial skeletal formation. Bone defects have been analyzed in mice using X-rays and microCT analysis (Lengner et al., *J. Cell Biol.* 172:909-921, 2006), and we will also examine hematopoietic properties and make appropriate crosses to determine whether the Xist transgene corrects the deficiency in male fertility. In addition, maintenance of gene silencing will be assayed in a variety of organs by both qPCR for genes present of the T($17^{16}$)65Dn chromosome as well as by analysis of GFP expression, and by standard molecular cytological methods.

Relevance of Trisomy 21 to Hematological Abnormalities and Bone Marrow Stem Cells:

We will test this strategy to silence the trisomic chromosome in bone marrow cells. There is a direct and measurable clinical impact of trisomy on bone marrow function. DS children develop hematological abnormalities, ranging from mild to severe. For example, neonates with DS commonly develop a transient myeloproliferative disorder (TMD; also termed transient leukemia). Although TMD often is self-resolving, it is highly predictive of later development of acute leukemia, can result directly in significant morbidity, and may be fatal in 10-20% of affected infants. Most importantly, it is well established that DS children have a greatly increased risk of progressing to leukemia, such that 2% of childhood leukemia patients have DS. The incidence of ALL and AML is 20 fold higher than normal, and the normally very rare AMKL (acute megakaryoblastic leukemia) is increased a remarkable 500 fold (Lange, *Br. J. Haematol.* 110:512-524, 2000). Finally, most DS children have MCV (mean corpuscular volume) above the $97^{th}$ percentile. While not a significant clinical concern, this is indicative of disordered hematopoiesis and provides a prevalent "marker" of the syndrome (also in the mouse DS model), that could be readily evaluated in "corrected" cells.

Regarding the Ts65Dn model (above), an important report just appeared which demonstrates that it also provides a good model for many of the hematological abnormalities seen in human DS (Kirsammer et al., *Blood* 111(2), 2008). The DS mice exhibit a highly penetrant myeloproliferative disease, as well as macrocytosis, dysplastic megakaryocyte morphology, and myelofibrosis. Therefore, we will test the chromosome silencing strategy in bone marrow stem cells from the Ts65Dn mouse. In addition to the clinical impact of trisomy on hematological abnormalities, the study of bone marrow is advantageous because it is an accessible source of cells that can be genetically manipulated, and then replaced. Furthermore, a study of the Xist mechanism, using random integration of inducible Xist transgenes, provided evidence that hematopoeitic precursor cells of adult mice are most readily competent to support chromosome silencing (Savarese et al., *Mol. Cell. Biol.* 26:7167-7177, 2006). (This study was unrelated to any concept regarding therapeutic use of Xist transgenes.) We will use inducible mouse Xist transgene constructs as described in Savarese (supra), and we can include in these constructs GFP, which will facilitate sorting and enrichment of cells carrying the Xist transgene. Ultimately, the silencing of the transgenic chromosome would be verified using procedures described above and the modified cells will be reintroduced, after bone marrow ablation by radiation. At various intervals after "chromosome correction", hematological analysis will be carried out to determine whether or to what extent the aforementioned anomalies of the DS mouse, particularly the myeloproliferative disease and the prevalent macrocytosis, have been ameliorated.

Use of Inducible Xist Transgene to Test Phenotypic Benefits Later in Development:

To determine the extent of the therapeutic benefit achieved when the trisomic chromosome is silenced later in development, we will generate ES/iPS cells that contain the doxycyclin inducible Xist transgene, or another indicible Xist construct (e.g., Cre/Lox mediated removal of drug resistance gene generating a new construct where Xist is transcribed using the drug resistance promoter). The inducible Xist transgene can then be turned on in both undifferentiated ES/iPS cells as well as at different times during differentiation and in terminally differentiated cells to assess the developmental competence of inactivation.

The same inducible transgenic iPS/ES cells can be used to induce the "rescue" later in fetal development, allowing the evaluation of phenotypic benefits in more differentiated cells. Addition of doxycyclin to the drinking water of the pregnant dams bearing the chimeric mice for 14 days should result in activation of the tet promoter controlling Xist expression, and Xist-mediated silencing of the T($17^{16}$)65Dn chromosome. A similar strategy has been used previously in mice to regulate Xist expression in hematopoietic precursor cells (Savarese et al., *Mol. Cell. Biol.* 26:7167-7177, 2006).

A number of embodiments of the invention have been described. Nevertheless, it will be understood that various modifications may be made without departing from the spirit and scope of the invention. Accordingly, other embodiments are within the scope of the following claims.

What is claimed is:

1. A method of reducing gene expression from a trisomic human chromosome 13, 18, or 21 or mouse chromosome 16 in a cell, the method comprising:
   providing a cell comprising a trisomic human chromosome 13, 18, or 21 or mouse chromosome 16; and introducing into the cell a vector comprising a nucleic acid construct comprising:
   a silencing sequence encoding an Xist RNA; and
   first and second sequences homologous to a site of desired integration in human chromosome 13, 18, or 21 or mouse chromosome 16 that specifically direct insertion of the silencing sequence into human chromosome 13, 18, or 21 or mouse chromosome 16 by homologous recombination.

2. The method of claim 1, wherein the silencing sequence is a full-length Xist gene sequence.

3. The method of claim 1, wherein the silencing sequence is an Xist gene sequence exclusive of one or more introns.

4. The method of claim 1, wherein the silencing sequence comprises about 6 kb to about 10 kb of exon 1 of an Xist gene sequence.

5. The method of claim 4, wherein the silencing sequence comprises the Xist cDNA sequence having accession number M97168 or a biologically active fragment or other variant thereof.

6. The method of claim 1, wherein the silencing sequence comprises a biologically active fragment or other biologically active variant of a naturally occurring Xist gene sequence.

7. The method of claim 1, further comprising a regulatory sequence.

8. The method of claim 7, wherein the regulatory sequence is a constitutively active, inducible, tissue-specific, or developmental stage-specific promoter.

9. The method of claim 1, wherein the first and second sequences direct insertion of the silencing sequence into a polymorphic region of the targeted chromosome.

10. The method of claim 1, wherein the first and second sequences direct insertion of the silencing sequence into an APP gene.

11. The method of claim 1, wherein the vector comprising the nucleic acid construct further comprises a selectable marker.

12. The method of claim 1, wherein the cell is a somatic cell, a germ cell, a stem cell, or a precursor cell.

13. The method of claim 12, wherein the stem cell is an embryonic stem cell, an adult stem cell, or an induced pluripotent stem cell.

14. The method of claim 13, wherein the adult stem cell is a hematopoietic stem cell or a neural stem cell.

15. The method of claim 1, wherein the cell is a differentiated cell.

16. The method of claim 1, wherein the differentiated cell is a fibroblast or neuron.

\* \* \* \* \*

UNITED STATES PATENT AND TRADEMARK OFFICE
CERTIFICATE OF CORRECTION

PATENT NO. : 8,574,900 B2  
APPLICATION NO. : 13/483240  
DATED : November 5, 2013  
INVENTOR(S) : Jeanne B. Lawrence and Lisa L. Hall Page 1 of 1

It is certified that error appears in the above-identified patent and that said Letters Patent is hereby corrected as shown below:

On the Title page, Item (56) References Cited, column 2, line 2, delete "o fan" and replace with -- of an --.

In the Specification

Column 1, line 17, delete "and HD007439" and replace with -- HD007439, and GM096400 --.

Signed and Sealed this  
First Day of April, 2014

Michelle K. Lee  
*Deputy Director of the United States Patent and Trademark Office*